US011703506B2

(12) United States Patent
Kasdan et al.

(10) Patent No.: US 11,703,506 B2
(45) Date of Patent: Jul. 18, 2023

(54) SYSTEMS AND METHODS FOR DETERMINING A CHEMICAL STATE

(71) Applicant: ACCELLIX LTD., Jerusalem (IL)

(72) Inventors: Harvey Lee Kasdan, Jerusalem (IL); Julien Meissonnier, Jerusalem (IL); Yoav Zuta, Jerusalem (IL); Micha Rosen, Jerusalem (IL); Yael Himmel, Jerusalem (IL); Yehoshua Broder, Jerusalem (IL); Bruce Davis, Clifton, ME (US); Bruce Goldman, Jerusalem (IL); Boaz Giron, Jerusalem (IL); Zion Botesazan, Jerusalem (IL); Eliezer Blasberg, Jerusalem (IL); Ilan Semmel, Jerusalem (IL); Jacques Aschkenasy, Jerusalem (IL)

(73) Assignee: Accellix Ltd., Jerusalem (IL)

( * ) Notice: Subject to any disclaimer, the term of this patent is extended or adjusted under 35 U.S.C. 154(b) by 494 days.

(21) Appl. No.: 17/000,322

(22) Filed: Aug. 23, 2020

(65) Prior Publication Data
US 2020/0386756 A1 Dec. 10, 2020

Related U.S. Application Data

(63) Continuation of application No. 16/010,520, filed on Jun. 18, 2018, now Pat. No. 10,761,094, which is a
(Continued)

(51) Int. Cl.
B01L 3/00 (2006.01)
G01N 33/569 (2006.01)
(Continued)

(52) U.S. Cl.
CPC ........ G01N 33/56972 (2013.01); B01L 3/502 (2013.01); B01L 3/5027 (2013.01);
(Continued)

(58) Field of Classification Search
CPC .......... B01L 3/502715; B01L 3/50273; B01L 3/502761; B01L 2200/10;
(Continued)

(56) References Cited

U.S. PATENT DOCUMENTS 3,241,432 A 3/1966 Skeggs et al.
4,233,029 A 11/1980 Columbus
(Continued)

FOREIGN PATENT DOCUMENTS

CN 1717280 A 1/2006
CN 101082621 A 12/2007
(Continued)

OTHER PUBLICATIONS

Adams, L. R., & Kamentsky, L. A. (1971). Machine characterization of human leukocytes by acridine orange fluorescence. Acta cytologica, 15(3), 289.
(Continued)

Primary Examiner — Melanie Brown
(74) Attorney, Agent, or Firm — Mark S. Cohen; Pearl Cohen Zedek, Latzer Baratz LLP

(57) ABSTRACT

The present invention provides self-contained systems for performing an assay for determining a chemical state, the system including a stationary cartridge for performing the assay therein, at least one reagent adapted to react with a sample; and at least one reporter functionality adapted to report a reaction of the at least one reagent with said sample to report a result of the assay, wherein the at least one reagent, the sample and the at least one reporter functionality are contained within the cartridge.

21 Claims, 38 Drawing Sheets

Related U.S. Application Data continuation of application No. 15/670,560, filed on Aug. 7, 2017, now Pat. No. 10,024,855, which is a continuation of application No. 14/646,395, filed as application No. PCT/IL2013/000092 on Dec. 17, 2013, now Pat. No. 9,759,722, which is a continuation-in-part of application No. 13/716,246, filed on Dec. 17, 2012, now abandoned.

(60) Provisional application No. 61/737,854, filed on Dec. 17, 2012, provisional application No. 61/737,856, filed on Dec. 17, 2012.

(51) Int. Cl.

| | | |
|---|---|---|
| *G01N 21/75* | (2006.01) | |
| *G01N 21/64* | (2006.01) | |
| *G01N 21/03* | (2006.01) | |
| *G01N 15/14* | (2006.01) | |
| *G01N 33/50* | (2006.01) | |
| *G01N 33/53* | (2006.01) | |
| *G01N 33/543* | (2006.01) | |
| *G01N 33/58* | (2006.01) | |
| *G01N 33/68* | (2006.01) | |
| *G01N 15/10* | (2006.01) | |
| *G01N 35/00* | (2006.01) | |

(52) U.S. Cl.
CPC ..... *B01L 3/50273* (2013.01); *B01L 3/502715* (2013.01); *B01L 3/502761* (2013.01); *G01N 15/1459* (2013.01); *G01N 15/1484* (2013.01); *G01N 21/03* (2013.01); *G01N 21/6428* (2013.01); *G01N 21/75* (2013.01); *G01N 33/5091* (2013.01); *G01N 33/5302* (2013.01); *G01N 33/54386* (2013.01); *G01N 33/569* (2013.01); *G01N 33/582* (2013.01); *G01N 33/68* (2013.01); *G01N 33/6872* (2013.01); *B01L 2200/025* (2013.01); *B01L 2200/10* (2013.01); *B01L 2300/041* (2013.01); *B01L 2300/0654* (2013.01); *B01L 2300/0816* (2013.01); *B01L 2300/0867* (2013.01); *B01L 2300/0877* (2013.01); *B01L 2300/0883* (2013.01); *B01L 2300/123* (2013.01); *B01L 2300/18* (2013.01); *B01L 2400/0406* (2013.01); *B01L 2400/0481* (2013.01); *B01L 2400/0487* (2013.01); *G01N 2015/1006* (2013.01); *G01N 2021/0328* (2013.01); *G01N 2021/6439* (2013.01); *G01N 2021/6482* (2013.01); *G01N 2035/00158* (2013.01); *G01N 2333/70535* (2013.01); *G01N 2333/70596* (2013.01); *G01N 2800/26* (2013.01)

(58) Field of Classification Search
CPC ........ B01L 2300/0816; G01N 21/6428; G01N 33/5091; G01N 33/582; G01N 2021/6439
See application file for complete search history.

(56) References Cited

U.S. PATENT DOCUMENTS

| | | |
|---|---|---|
| 4,376,820 A | 3/1983 | Giannini et al. |
| 4,400,370 A | 8/1983 | Kass |
| 4,444,879 A | 4/1984 | Foster et al. |
| 4,554,257 A | 11/1985 | Aladjem et al. |
| 4,660,971 A | 4/1987 | Sage et al. |
| 4,684,252 A | 8/1987 | Makiguchi et al. |
| 4,730,899 A | 3/1988 | Kime et al. |
| 4,745,285 A | 5/1988 | Recktenwald et al. |
| 4,882,284 A | 11/1989 | Kirchanski et al. |
| 5,126,276 A | 6/1992 | Fish et al. |
| 5,304,487 A | 4/1994 | Wilding et al. |
| 5,311,426 A | 5/1994 | Donohue et al. |
| 5,408,314 A | 4/1995 | Perry et al. |
| 5,627,040 A | 5/1997 | Bierre et al. |
| 5,627,041 A | 5/1997 | Shartle et al. |
| 5,631,734 A | 5/1997 | Stern |
| 5,716,852 A | 2/1998 | Yager et al. |
| 5,726,404 A | 3/1998 | Brody |
| 5,747,349 A | 5/1998 | van den Engh et al. |
| 5,837,115 A | 11/1998 | Austin et al. |
| 5,932,100 A | 8/1999 | Yager et al. |
| 5,972,710 A | 10/1999 | Weigl et al. |
| 5,981,956 A | 11/1999 | Stern |
| 6,136,610 A | 10/2000 | Polito et al. |
| 6,168,948 B1 | 1/2001 | Anderson et al. |
| 6,274,323 B1 | 8/2001 | Bruchez et al. |
| 6,280,148 B1 | 8/2001 | Zengerle et al. |
| 6,372,516 B1 | 4/2002 | Sun |
| 6,382,228 B1 | 5/2002 | Cabuz et al. |
| 6,399,952 B1 | 6/2002 | Maher et al. |
| 6,426,230 B1 | 7/2002 | Feistel |
| 6,540,895 B1 | 4/2003 | Spence et al. |
| 6,541,213 B1 | 4/2003 | Weigl et al. |
| 6,551,841 B1 | 4/2003 | Wilding et al. |
| 6,635,163 B1 | 10/2003 | Han et al. |
| 6,636,623 B2 | 10/2003 | Nelson et al. |
| 6,637,463 B1 | 10/2003 | Lei et al. |
| 6,674,058 B1 | 1/2004 | Miller |
| 6,674,525 B2 | 1/2004 | Bardell et al. |
| 6,852,284 B1 | 2/2005 | Holl et al. |
| 6,897,954 B2 | 5/2005 | Bishop et al. |
| 7,024,316 B1 | 4/2006 | Ellison et al. |
| 7,105,355 B2 | 9/2006 | Kurabayashi et al. |
| 7,109,459 B2 | 9/2006 | Kam et al. |
| 7,192,560 B2 | 3/2007 | Parthasarathy |
| 7,217,573 B1 | 5/2007 | Oshida et al. |
| 7,247,274 B1 | 7/2007 | Chow |
| 7,277,166 B2 | 10/2007 | Padmanabhan et al. |
| 7,347,976 B2 | 3/2008 | Parthasarathy et al. |
| 7,473,529 B1 | 1/2009 | Porter et al. |
| 7,553,453 B2 | 6/2009 | Gu et al. |
| 7,569,373 B2 | 8/2009 | Mori et al. |
| 7,718,421 B2 | 5/2010 | Chen et al. |
| 7,763,453 B2 | 7/2010 | Clemmens et al. |
| 7,995,202 B2 | 8/2011 | Lundquist et al. |
| 8,007,999 B2 | 8/2011 | Holmes et al. |
| 8,097,225 B2 | 1/2012 | Padmanabhan et al. |
| 8,116,984 B2 | 2/2012 | Davis et al. |
| 8,273,294 B2 | 9/2012 | Padmanabhan et al. |
| D669,191 S | 10/2012 | Handique |
| 8,318,109 B2 | 11/2012 | Saltsman et al. |
| 8,364,418 B2 | 1/2013 | Davis et al. |
| 8,518,705 B2 | 8/2013 | Chan et al. |
| 8,945,913 B2 | 2/2015 | Kasdan et al. |
| 9,029,158 B2 | 5/2015 | Tai et al. |
| 9,121,850 B2 | 9/2015 | Kang et al. |
| 9,163,279 B2 | 10/2015 | Wakeley et al. |
| 9,207,239 B2 | 12/2015 | Kasdan et al. |
| 9,234,884 B2 | 1/2016 | Tai et al. |
| 9,354,176 B2 | 5/2016 | Nishikawa |
| 9,535,059 B2 | 1/2017 | Tai et al. |
| 9,731,297 B2 | 8/2017 | Glezer et al. |
| 9,757,729 B2 | 9/2017 | Tai et al. |
| 9,939,909 B2 | 4/2018 | Yamagishi et al. |
| 9,989,523 B2 | 6/2018 | Kasdan et al. |
| 10,184,884 B2 | 1/2019 | Anderson et al. |
| 2001/0008760 A1 | 7/2001 | King et al. |
| 2001/0027745 A1 | 10/2001 | Weigl et al. |
| 2001/0030290 A1 | 10/2001 | Stern |
| 2001/0049689 A1 | 12/2001 | Mentzer |
| 2002/0028519 A1 | 3/2002 | Yguerabide et al. |
| 2002/0031255 A1 | 3/2002 | Kasdan et al. |
| 2002/0037520 A1 | 3/2002 | Nikiforov et al. |
| 2002/0090644 A1 | 7/2002 | Weigl et al. |
| 2002/0113961 A1 | 8/2002 | Gamble et al. |
| 2002/0164636 A1 | 11/2002 | Pruitt et al. |
| 2002/0168784 A1 | 11/2002 | Sundrehagen et al. |
| 2002/0177174 A1 | 11/2002 | Zock et al. |

(56) References Cited

U.S. PATENT DOCUMENTS

| | | |
|---|---|---|
| 2002/0186874 A1 | 12/2002 | Price et al. |
| 2003/0002037 A1 | 1/2003 | Kasdan et al. |
| 2003/0073089 A1 | 4/2003 | Mauze et al. |
| 2003/0103981 A1 | 6/2003 | Spancake et al. |
| 2003/0153844 A1 | 8/2003 | Smith et al. |
| 2003/0170881 A1 | 9/2003 | Davis et al. |
| 2003/0175990 A1 | 9/2003 | Hayenga et al. |
| 2003/0194752 A1 | 10/2003 | Anderson et al. |
| 2003/0212424 A1 | 11/2003 | Briggs et al. |
| 2003/0233827 A1 | 12/2003 | Kuo et al. |
| 2004/0037739 A1* | 2/2004 | McNeely ............... B01L 3/5085 422/417 |
| 2004/0053290 A1 | 3/2004 | Terbrueggen et al. |
| 2004/0115838 A1 | 6/2004 | Quake et al. |
| 2004/0126008 A1 | 7/2004 | Chapoulaud et al. |
| 2004/0155309 A1 | 8/2004 | Sorin et al. |
| 2004/0191783 A1 | 9/2004 | Leclercq et al. |
| 2004/0197233 A1* | 10/2004 | Nagaoka ............... G01N 35/025 422/81 |
| 2004/0217256 A1 | 11/2004 | Ortyn et al. |
| 2004/0248205 A1 | 12/2004 | Stern et al. |
| 2005/0069958 A1 | 3/2005 | Mills et al. |
| 2005/0105077 A1 | 5/2005 | Padmanabhan et al. |
| 2005/0118723 A1 | 6/2005 | Padmanabhan |
| 2005/0121596 A1 | 6/2005 | Kam et al. |
| 2005/0148093 A1 | 7/2005 | Chien |
| 2005/0154268 A1 | 7/2005 | Hwang et al. |
| 2005/0181466 A1 | 8/2005 | Dambinova et al. |
| 2005/0221281 A1 | 10/2005 | Ho |
| 2005/0255001 A1 | 11/2005 | Padmanabhan et al. |
| 2005/0255600 A1 | 11/2005 | Padmanabhan et al. |
| 2005/0261560 A1 | 11/2005 | Ridder et al. |
| 2005/0275839 A1 | 12/2005 | Robinson et al. |
| 2006/0011539 A1 | 1/2006 | Lee et al. |
| 2006/0011862 A1 | 1/2006 | Bernstein et al. |
| 2006/0134599 A1 | 6/2006 | Toner et al. |
| 2006/0134712 A1 | 6/2006 | Stromgren et al. |
| 2006/0205012 A1 | 9/2006 | DeBad et al. |
| 2006/0215155 A1 | 9/2006 | Weber |
| 2006/0246575 A1 | 11/2006 | Lancaster et al. |
| 2006/0263888 A1 | 11/2006 | Fritz et al. |
| 2006/0269446 A1 | 11/2006 | Gilbert et al. |
| 2007/0015179 A1 | 1/2007 | Klapperich et al. |
| 2007/0031289 A1 | 2/2007 | Cox et al. |
| 2007/0059685 A1 | 3/2007 | Kohne |
| 2007/0098594 A1 | 5/2007 | Elkin et al. |
| 2007/0183935 A1* | 8/2007 | Clemmens .......... B01L 3/50273 435/286.7 |
| 2007/0190525 A1 | 8/2007 | Gu et al. |
| 2007/0227890 A1 | 10/2007 | Ramsey et al. |
| 2007/0253868 A1 | 11/2007 | Beebe et al. |
| 2007/0281311 A1 | 12/2007 | Roth et al. |
| 2007/0292941 A1 | 12/2007 | Handique et al. |
| 2008/0038873 A1 | 2/2008 | Tanida et al. |
| 2008/0101993 A1 | 5/2008 | Andersson et al. |
| 2008/0176253 A1 | 7/2008 | Christodoulides et al. |
| 2008/0212102 A1 | 9/2008 | Nuzzo et al. |
| 2008/0213854 A1 | 9/2008 | Wirth et al. |
| 2009/0042241 A1 | 2/2009 | Yu-Chong et al. |
| 2009/0059222 A1 | 3/2009 | Tan et al. |
| 2009/0117605 A1 | 5/2009 | Davis et al. |
| 2009/0148847 A1 | 6/2009 | Kokoris et al. |
| 2009/0181411 A1 | 7/2009 | Battrell et al. |
| 2009/0233300 A1 | 9/2009 | Saavedra et al. |
| 2010/0035349 A1 | 2/2010 | Bau et al. |
| 2010/0051124 A1 | 3/2010 | Imran |
| 2010/0056383 A1 | 3/2010 | Ririe et al. |
| 2010/0093019 A1 | 4/2010 | Ditcham et al. |
| 2010/0120083 A1 | 5/2010 | Ritzen et al. |
| 2010/0255473 A1 | 10/2010 | Ermantraut et al. |
| 2011/0094577 A1 | 4/2011 | Chatterjee et al. |
| 2011/0184537 A1 | 7/2011 | Kasdan et al. |
| 2012/0071342 A1 | 3/2012 | Lochhead et al. |
| 2012/0164036 A1 | 6/2012 | Stern et al. |
| 2012/0164627 A1 | 6/2012 | Battrell et al. |
| 2012/0177543 A1 | 7/2012 | Battrell et al. |
| 2012/0187117 A1 | 7/2012 | Weber |
| 2012/0266986 A1 | 10/2012 | Wimberger-Friedl et al. |
| 2012/0275972 A1 | 11/2012 | Schoen et al. |
| 2012/0280143 A1 | 11/2012 | Kim et al. |
| 2012/0329878 A1 | 12/2012 | Coussens et al. |
| 2013/0065269 A1 | 3/2013 | Nitta |
| 2013/0102087 A1 | 4/2013 | Kasdan et al. |
| 2013/0115607 A1 | 5/2013 | Nielsen et al. |
| 2013/0130262 A1 | 5/2013 | Battrell et al. |
| 2013/0130400 A1 | 5/2013 | Harbers et al. |
| 2013/0137135 A1 | 5/2013 | Tai et al. |
| 2013/0177543 A1 | 7/2013 | Patel et al. |
| 2013/0230867 A1 | 9/2013 | Davis et al. |
| 2013/0314705 A1 | 11/2013 | Tanabe et al. |
| 2013/0323737 A1 | 12/2013 | Zenhausern et al. |
| 2013/0323825 A1 | 12/2013 | Sekino et al. |
| 2014/0170678 A1 | 6/2014 | Kasdan et al. |
| 2014/0194305 A1 | 7/2014 | Kayyem et al. |
| 2014/0273188 A1 | 9/2014 | Mohan et al. |
| 2014/0287435 A1 | 9/2014 | Kasdan et al. |
| 2014/0377742 A1 | 12/2014 | Tai et al. |
| 2015/0004717 A1 | 1/2015 | McDevitt et al. |
| 2015/0132776 A1 | 5/2015 | Kasdan et al. |
| 2015/0309011 A1 | 10/2015 | Tai et al. |
| 2015/0338401 A1 | 11/2015 | Ram |
| 2016/0146793 A1 | 5/2016 | Kasdan et al. |
| 2017/0136463 A1 | 5/2017 | Tai et al. |

FOREIGN PATENT DOCUMENTS

| | | |
|---|---|---|
| CN | 101300478 A | 11/2008 |
| CN | 101389947 A | 3/2009 |
| CN | 101765462 A | 6/2010 |
| CN | 101848765 A | 9/2010 |
| CN | 102513168 A | 6/2012 |
| CN | 102740976 A | 10/2012 |
| EP | 1263533 A2 | 12/2002 |
| EP | 1846159 A2 | 10/2007 |
| JP | 2008544214 A | 12/2008 |
| JP | 2008545141 A | 12/2008 |
| JP | 2009529883 A | 8/2009 |
| JP | 2012508879 A | 4/2012 |
| JP | 2012132879 A | 7/2012 |
| WO | WO/2001/068238 A2 | 9/2001 |
| WO | WO/2006/055816 A2 | 5/2006 |
| WO | WO/2006/079082 A2 | 7/2006 |
| WO | WO/2006/118586 A2 | 11/2006 |
| WO | WO/2007/076549 A2 | 7/2007 |
| WO | WO-2008002462 A2 | 1/2008 |
| WO | WO/2008/121828 A2 | 10/2008 |
| WO | WO/2008/124589 A2 | 10/2008 |
| WO | WO/2009/003493 A2 | 1/2009 |
| WO | WO/2009/144660 A1 | 12/2009 |
| WO | WO/2011/094577 A2 | 8/2011 |
| WO | WO/2011/128893 A2 | 10/2011 |
| WO | WO/2012/019599 A2 | 2/2012 |
| WO | WO/2012/020257 A1 | 2/2012 |
| WO | WO/2012071342 A2 | 5/2012 |
| WO | WO/2012/092010 A2 | 7/2012 |
| WO | WO/2012/120506 A2 | 9/2012 |
| WO | WO/2012/170711 A1 | 12/2012 |
| WO | WO/2014/097286 A1 | 6/2014 |
| WO | WO/2014/097287 A1 | 6/2014 |

OTHER PUBLICATIONS

Adams, L. R., & Kamentsky, L. A. (1974). Fluorometric characterization of six classes of human leukocytes. Acta cytologica, 18(5), 389.

Altendorf, E., Zebert, D., Holl, M., & Yager, P. (Jun. 1997). Differential blood cell counts obtained using a microchannel based flow cytometer. In Proceedings of International Solid State Sensors and Actuators Conference (Transducers' 97) (vol. 1, pp. 531-534). IEEE.

Aouani, H., Deiss, F., Wenger, J., Ferrand, P., Sojic, N., & Rigneault, H. (2009). Optical-fiber-microsphere for remote fluorescence correlation spectroscopy. Optics express, 17(21), 19085-19092.

(56) References Cited

OTHER PUBLICATIONS

Assicot, M., Bohuon, C., Gendrel, D., Raymond, J., Carsin, H., & Guilbaud, J. (1993). High serum procalcitonin concentrations in patients with sepsis and infection. The Lancet, 341(8844), 515-518.

Aulesa, C., Pastor, I., Naranjo, D., Piqueras, J., & Galimany, R. (2003). Validation of the Coulter LH 750 in a hospital reference laboratory. Laboratory Hematology, 9, 15-28.

Ault, K. A. (1993). Flow Cytometric Measurement of Platelet Function and Reticulated Platelets: Brief Description of Platelets. Annals of the New York Academy of Sciences, 677(1), 293-308.

Bellows—definition from the Columbia Electronic EncyclopediaCopyright 2013, Columbia University Press. Licensed from Columbia University Press. All rights reserved, www.cc.columbia.edu/cu/cup/.

Bhattacharya, S., Datta, A., Berg, J. M., & Gangopadhyay, S. (2005). Studies on surface wettability of poly (dimethyl) siloxane (PDMS) and glass under oxygen-plasma treatment and correlation with bond strength. Journal of microelectromechanical systems, 14(3), 590-597.

Björnsson, S., Wahlström, S., Norström, E., Bernevi, I., O'Neill, U., Johansson, E., . . . & Simonsson, P. (2008). Total nucleated cell differential for blood and bone marrow using a single tube in a five-color flow cytometer. Cytometry Part B: Clinical Cytometry, 74(2), 91-103.

Blajchman, M. A., Beckers, E. A., Dickmeiss, E., Lin, L., Moore, G., & Muylle, L. (2005). Bacterial detection of platelets: current problems and possible resolutions. Transfusion medicine reviews, 19(4), 259-272.

Bodensteiner, D. C. (1989). A flow cytometric technique to accurately measure post-filtration white blood cell counts. Transfusion, 29(7), 651-653.

Buhlmann, C., Preckel, T., Chan, S., Luedke, G., & Valer, M. (2003). A new tool for routine testing of cellular protein expression: integration of cell staining and analysis of protein expression on a microfluidic chip-based system. Journal of biomolecular techniques: JBT, 14(2), 119.

Chen, H. T., & Wang, Y. N. (2008). Fluorescence detection in a micro flow cytometer without on-chip fibers. Microfluidics and nanofluidics, 5(5), 689-694.

Cheson, B. D., Bennett, J. M., Grever, M., Kay, N., Keating, M. J., O'Brien, S., & Rai, K. R. (1996). National Cancer Institute-sponsored Working Group guidelines for chronic lymphocytic leukemia: revised guidelines for diagnosis and treatment. Blood, 87(12), 4990-4997.

Christ-Crain, M., Jaccard-Stolz, D., Bingisser, R., Gencay, M. M., Huber, P. R., Tamm, M., & Müller, B. (2004). Effect of procalcitonin-guided treatment on antibiotic use and outcome in lower respiratory tract infections: cluster-randomised, single-blinded intervention trial. The Lancet, 363(9409), 600-607.

Cristofanilli, M., Budd, G. T., Ellis, M. J., Stopeck, A., Matera, J., Miller, M. C., . . . & Hayes, D. F. (2004). Circulating tumor cells, disease progression, and survival in metastatic breast cancer. New England Journal of Medicine, 351(8), 781-791.

Cui, L., Zhang, T., & Morgan, H. (2001). Optical particle detection integrated in a dielectrophoretic lab-on-a-chip. Journal of Micromechanics and Microengineering, 12(1), 7.

Davis, B. H., Olsen, S. H., Ahmad, E., & Bigelow, N. C. Neutrophil CD64 is an Improved Indicator of Infection or Sepsis in Emergency Room Patients.

Dieye, T. N., Vereecken, C., Diallo, A. A., Ondoa, P., Diaw, P. A., Camara, M., . . . & Kestens, L. (2005). Absolute CD4 T-cell counting in resource-poor settings: direct volumetric measurements versus bead-based clinical flow cytometry instruments. JAIDS Journal of Acquired Immune Deficiency Syndromes, 39(1), 32-37.

Dittrich, P. S., & Manz, A. (2005). Single-molecule fluorescence detection in microfluidic channels—the Holy Grail in μTAS?. Analytical and bioanalytical chemistry, 382(8), 1771-1782.

Dittrich, P. S., & Schwille, P. (2003). An integrated microfluidic system for reaction, high-sensitivity detection, and sorting of fluorescent cells and particles. Analytical chemistry, 75(21), 5767-5774.

Divers, S. G., Kannan, K., Stewart, R. M., Betzing, K. W., Dempsey, D., Fukuda, M., . . . & Holcombe, R. F. (1995). Quantitation of CD62, soluble CD62, and lysosome-associated membrane proteins 1 and 2 for evaluation of the quality of stored platelet concentrates. Transfusion, 35(4), 292-297.

Drexler, H. G., Menon, M., Gignac, S. M., Misra, B., & Minowada, J. (1986). Diagnostic value of immunological leukemia phenotyping. Acta haematologica, 76(1), 1-8.

Dziegiel, M. H., Nielsen, L. K., & Berkowicz, A. (2006). Detecting fetomaternal hemorrhage by flow cytometry. Current opinion in hematology, 13(6), 490-495.

Ernst, D., Bolton, G., Recktenwald, D., Cameron, M. J., Danesh, A., Persad, D., . . . & Gaur, A. (2006). Bead-based flow cytometric assays: a multiplex assay platform with applications in diagnostic microbiology. In Advanced techniques in diagnostic microbiology (pp. 427-443). Springer, Boston, MA.

European Search Report dated Jan. 29, 2019 for corresponding European Patent Application No. EP18194844.9, dated Dec. 17, 2013.

European Search Report dated Mar. 1, 2016 for corresponding European Patent Application No. EP11768557.8, dated Apr. 11, 2011.

European Search Report dated Oct. 28, 2016 for corresponding European Patent Application No. EP13864008.1, dated Dec. 17, 2013.

European Search Report dated Sep. 19, 2017 for corresponding European Patent Application No. EP17173498.1, dated Apr. 11, 2011.

European Search Report dated Sep. 21, 2016 for corresponding European Patent Application No. EP13865771.3, dated Dec. 17, 2013.

European Search Report dated Jun. 7, 2019 for corresponding European Patent Application No. EP18215979.8, dated Dec. 17, 2013.

Ferris, M. M., McCabe, M. O., Doan, L. G., & Rowlen, K. L. (2002). Rapid enumeration of respiratory viruses. Analytical chemistry, 74(8), 1849-1856.

Fischer, J. C., Quenzel, E. M., Moog, R., Wenzel, F., Riethmacher, R., Tutschek, B., & Giers, G. (2011). Reducing costs in flow-cytometric counting of residual white blood cells in blood products: utilization of a single-platform bead-free flow-rate calibration method. Transfusion, 51(7), 1431-1438.

Frengen, J., Kierulf, B., Schmid, R., Lindmo, T., & Nustad, K. (1994). Demonstration and minimization of serum interference in flow cytometric two-site immunoassays. Clinical chemistry, 40(3), 420-425.

Frengen, J., Schmid, R., Kierulf, B., Nustad, K., Paus, E., Berge, A., & Lindmo, T. (1993). Homogeneous immunofluorometric assays of alpha-fetoprotein with macroporous, monosized particles and flow cytometry. Clinical chemistry, 39(10), 2174-2181.

Fujimoto, K. (1999). Principles of measurement in hematology analyzers manufactured by Sysmex Corporation. Sysmex Journal International, 9(1; SEAS SUM), 31-44.

Gawad, S., Schild, L., & Renaud, P. (2001). Micromachined impedance spectroscopy flow cytometer for cell analysis and particle sizing. Lab on a Chip, 1(1), 76-82.

Gmitro, A. F., & Aziz, D. (1993). Confocal microscopy through a fiber-optic imaging bundle. Optics letters, 18(8), 565-567.

Gosling, J. P. (1990). A decade of development in immunoassay methodology. Clinical chemistry, 36(8), 1408-1427.

Graff, J., Klinkhardt, U., Schini-Kerth, V. B., Harder, S., Franz, N., Bassus, S., & Kirchmaier, C. M. (2002). Close relationship between the platelet activation marker CD62 and the granular release of platelet-derived growth factor. Journal of Pharmacology and Experimental Therapeutics, 300(3), 952-957.

Groselj-Grenc, M., Ihan, A., & Derganc, M. (2008). Neutrophil and monocyte CD64 and CD163 expression in critically ill neonates and children with sepsis: comparison of fluorescence intensities and calculated indexes. Mediators of inflammation, 2008.

Guerti, K., Vertessen, F., Daniëls, L., & Van Der Planken, M. (2009). Performance evaluation of the Pentra 60C+ automated hematology analyzer and comparison with the ADVIA 2120. International journal of laboratory hematology, 31(2), 132-141.

(56) References Cited

OTHER PUBLICATIONS

Hammatsu Photonics K.K. Electron Tube Division. Photon Counting Using Photomultiplier Tubes [online], Jul. 2005 (See bottom right of last page) [retrieve on Sep. 13, 2011], Retrieved from the Internet: <http://sales.hamamatsu.com/assets/applications/ETD/PhotonCounting_TPH09001E04.pdf>: table.1-2; p. 1, Introduction, p. 2, Fig. 2, p. 9, Section 3-1 and p. 14, col. 1.

Hawkins, R. C. (2007). Laboratory turnaround time. The Clinical Biochemist Reviews, 28(4), 179.

Hayenga, J., Bardell, R., Morris, C., Graham, P., Kesler, N., Lancaster, C., . . . & Saltsman, P. (2002). Enabling Technologies for a Personal Flow Cytometer, Part II: Integrated Analysis Cartridges. In Micro Total Analysis Systems 2002 (pp. 207-209). Springer, Dordrecht.

Hershman, M. J., Cheadle, W. G., Wellhausen, S. R., Davidson, P. F., & Polk Jr, H. C. (1990). Monocyte HLA-DR antigen expression characterizes clinical outcome in the trauma patient. British Journal of Surgery, 77(2), 204-207.

Hilfrich, R., & Hariri, J. (2008). Prognostic relevance of HPV L1 capsid protein detection within mild to moderate dysplastic lesions of the cervix uteri in combination with a second biomarker p16. Anal Quant Cytol Histol, 30(2), 78-82.

Hillier, S. L., Martius, J., Krohn, M., Kiviat, N., Holmes, K. K., & Eschenbach, D. A. (1988). A case-control study of chorioamnionic infection and histologic chorioamnionitis in prematurity. New England Journal of Medicine, 319(15), 972-978.

Hoffmann, J. J. (2011). Neutrophil CD64 as a sepsis biomarker. Biochemia medica: Biochemia medica, 21(3), 282-290.

Holmes, D., Morgan, H., & Green, N. G. (2006). High throughput particle analysis: Combining dielectrophoretic particle focussing with confocal optical detection. Biosensors and Bioelectronics, 21(8), 1621-1630.

Holmes, D., Pettigrew, D., Reccius, C. H., Gwyer, J. D., van Berkel, C., Holloway, J., . . . & Morgan, H. (2009). Leukocyte analysis and differentiation using high speed microfluidic single cell impedance cytometry. Lab on a Chip, 9(20), 2881-2889.

Hughes-Jones, N. C., Norley, I., Young, J. M., & England, J. M. (1974). Differential white cell counts by frequency distribution analysis of cell volumes. Journal of clinical pathology, 27(8), 623-625.

International Preliminary Report on Patentability—Chapter I dated Oct. 16, 2012 for PCT/IL2011/000296 filed Apr. 11, 2011.

International Preliminary Report on Patentability—Chapter I dated Jun. 23, 2015 for PCT/IL2013/000092 filed Dec. 17, 2013.

International Preliminary Report on Patentability—Chapter I dated Jun. 23, 2015 for PCT/IL2013/000093 filed Dec. 17, 2013.

International Search Report dated Jan. 3, 2012 for PCT/IL2011/000296 filed Apr. 11, 2011.

International Search Report dated Apr. 1, 2014 for PCT/IL2013/000092 filed Dec. 17, 2013.

International Search Report dated Apr. 2, 2014 for PCT/IL2013/000093 filed Dec. 17, 2013.

Jackson, J. F. (1961). Supravital blood studies, using acridine orange fluorescence. Blood, 17(5), 643-649.

Kass, L. (1981). Chlorazol black E: a new stain for granulocytic cells. Am J Clin Pathol, 76, 810-812.

Kass, L. (1988). Identification of lymphocyte subpopulations with a polymethine dye. Journal of Histochemistry & Cytochemistry, 36(7), 711-715.

Kibe, S., Adams, K., & Barlow, G. (2011). Diagnostic and prognostic biomarkers of sepsis in critical care. Journal of antimicrobial chemotherapy, 66(suppl_2), ii33-ii40.

Kostner, S & Vellekoop, M. J. (2008). Cell analysis in a microfluidic cytometer applying a DVD pickup head. Sensors and Actuators B: Chemical, 132(2), 512-517.

Krogmeier, J. R., Schaefer, I., Seward, G., Yantz, G. R., & Larson, J. W. (2007). An integrated optics microfluidic device for detecting single DNA molecules. Lab on a Chip, 7(12), 1767-1774.

Kunst, B. H., Schots, A., & Visser, A. J. (2004). Design of a confocal microfluidic particle sorter using fluorescent photon burst detection. Review of scientific instruments, 75(9), 2892-2898.

LaRosa, S. P., & Opal, S. M. (2011). Biomarkers: the future. Critical care clinics, 27(2), 407-419.

Lee, D. W., Yi, S., & Cho, Y. H. (Jan. 2005). A flow-rate independent cell counter using a fixed control volume between double electrical sensing zones. In 18th IEEE International Conference on Micro Electro Mechanical Systems, 2005. MEMS 2005. (pp. 678-681). IEEE.

Lee, G. B., Lin, C. H., & Chang, S. C. (2004). Micromachine-based multi-channel flow cytometers for cell/particle counting and sorting. Journal of Micromechanics and Microengineering, 15(3), 447.

Lin et al. ("Microfluidic Immunoassays," JALA, 2010, 15, 253-275).

Liu, N. I. N. G., Wu, A. H., & Wong, S. S. (1993). Improved quantitative Apt test for detecting fetal hemoglobin in bloody stools of newborns. Clinical chemistry, 39(11), 2326-2329.

Liu, P., Seo, T. S., Beyor, N., Shin, K. J., Scherer, J. R., & Mathies, R. A. (2007). Integrated portable polymerase chain reaction-capillary electrophoresis microsystem for rapid forensic short tandem repeat typing. Analytical chemistry, 79(5), 1881-1889.

Lotan, Y., Elias, K., Svatek, R. S., Bagrodia, A., Nuss, G., Moran, B., & Sagalowsky, A. I. (2009). Bladder cancer screening in a high risk asymptomatic population using a point of care urine based protein tumor marker. The Journal of urology, 182(1), 52-58.

Masse, M., Naegelen, C., Pellegrini, N., Segier, J. M., Marpaux, N., & Beaujean, F. (1992). Validation of a simple method to count very low white cell concentrations in filtered red cells or platelets. Transfusion, 32(6), 565-571.

Matic, G. B., Chapman, E. S., Zaiss, M., Rothe, G., & Schmitz, G. (1998). Whole blood analysis of reticulated platelets: improvements of detection and assay stability. Cytometry: the Journal of the International Society for Analytical Cytology, 34(5), 229-234.

McDonald, C. P., Colvin, J., Robbins, S., & Barbara, J. A. J. (2005). Use of a solid-phase fluorescent cytometric technique for the detection of bacteria in platelet concentrates. Transfusion Medicine, 15(3), 175-183.

Michelson, A. D. (1996). Flow cytometry: a clinical test of platelet function. Open Access Articles, 290.

Miller, E. M., Freire, S., & Wheeler, A. R. (2008). Proteomics in Microfluidic Devices. Encyclopedia of Microfluidics and Nanofluidics, 1749-1758.

Morgan, H., Holmes, D., & Green, N. G. (2006). High speed simultaneous single particle impedance and fluorescence analysis on a chip. Current Applied Physics, 6(3), 367-370.

Moriyama, Y., Takano, T., & Ohkuma, S. (1982). Acridine orange as a fluorescent probe for lysosomal proton pump. The Journal of Biochemistry, 92(4), 1333-1336.

Moro, R., Tcherkassova, J., Song, E., Shen, G., Moro, R., Schmid, R., . . . & Chen, C. (2005). A new broad-spectrum cancer marker. Vitro Diagnostic Technology.

Niehren, S., Kinzelbach, W., Seeger, S., & Wolfrum, J. (1995). An all-solid-state flow cytometer for counting fluorescent microspheres. Analytical Chemistry, 67(15), 2666-2671.

Oberjat, T. E., Zucker, R. M., & Cassen, B. (1970). Rapid and reliable differential counts on dilute leukocyte suspensions. The Journal of laboratory and clinical medicine, 76(3), 518-522.

Ozanich Jr, R. M., Bruckner-Lea, C. J., Warner, M. G., Miller, K., Antolick, K. C., Marks, J. D., . . . & Grate, J. W. (2009). Rapid multiplexed flow cytometric assay for botulinum neurotoxin detection using an automated fluidic microbead-trapping flow cell for enhanced sensitivity. Analytical chemistry, 81(14), 5783-5793.

Pál, J., Pálinkás, L., Nyárády, Z., Czömpöly, T., Marczinovits, I., Lustyik, G., . . . & Pár, A. (2005). Sandwich type ELISA and a fluorescent cytometric microbead assay for quantitative determination of hepatitis B virus X antigen level in human sera. Journal of immunological methods, 306(1-2), 183-192.

Patibandla, P. K., Estrada, R., Kannan, M., & Sethu, P. (2014). A microfluidics-based technique for automated and rapid labeling of cells for flow cytometry. Journal of Micromechanics and Microengineering, 24(3), 034002.

(56) References Cited

OTHER PUBLICATIONS

Perry, S. E., Mostafa, S. M., Wenstone, R., Shenkin, A., & McLaughlin, P. J. (2003). Is low monocyte HLA-DR expression helpful to predict outcome in severe sepsis?. Intensive care medicine, 29(8), 1245-1252.
Piyasena, M. E., & Graves, S. W. (2014). The intersection of flow cytometry with microfluidics and microfabrication. Lab on a Chip, 14(6), 1044-1059.
Preckel, T., Luedke, G., Chan, S. D., Wang, B. N., Dubrow, R., & Buhlmann, C. (2002). Detection of cellular parameters using a microfluidic chip-based system. JALA: Journal of the Association for Laboratory Automation, 7(4), 85-89.
Ramakumar, S., Bhuiyan, J., Besse, J. A., Roberts, S. G., Wollan, P. C., Blute, M. L, & O'kane, D. J. (1999). Comparison of screening methods in the detection of bladder cancer. The Journal of urology, 161(2), 388-394.
Rawstron, A. C., Kennedy, B., Evans, P. A., Davies, F. E., Richards, S. J., Haynes, A. P., . . . & Hillmen, P. (2001). Quantitation of minimal disease levels in chronic lymphocytic leukemia using a sensitive flow cytometric assay improves the prediction of outcome and can be used to optimize therapy. Blood, 98(1), 29-35.
Rodriguez, W. R., Christodoulides, N., Floriano, P. N., Graham, S., Mohanty, S., Dixon, M., . . . & Romanovicz, D. (2005). A microchip CD4 counting method for HIV monitoring in resource-poor settings. PLoS medicine, 2(7), e182.
Rylatt, D. B., Blake, A. S., Cottis, L. E., Massingham, D. A., Fletcher, W. A., Masci, P. P., . . . & Wyatt, D. (1983). An immunoassay for human D dimer using monoclonal antibodies. Thrombosis research, 31(6), 767-778.
Sacks, D. B., Bruns, D. E., Goldstein, D. E., Maclaren, N. K., McDonald, J. M., & Parrott, M. (2002). Guidelines and recommendations for laboratory analysis in the diagnosis and management of diabetes mellitus. Clinical chemistry, 48(3), 436-472.
Satake, D., Ebi, H., Oku, N., Matsuda, K., Takao, H., Ashiki, M., & Ishida, M. (2002). A sensor for blood cell counter using MEMS technology. Sensors and Actuators B: Chemical, 83(1-3), 77-81.
Schwartz, M. K., Bethune, V. G., Fleisher, M., Pennacchia, G., Menendez-Botet, C. J., & Lehman, D. (1974). Chemical and Clinical Evaluation of the Continuous-flow Analyzer"SMAC". Clinical chemistry, 20(8), 1062-1070.
Segal, H. C., Briggs, C., Kunka, S., Casbard, A., Harrison, P., Machin, S. J., & Murphy, M. F. (2005). Accuracy of platelet counting haematology analysers in severe thrombocytopenia and potential impact on platelet transfusion. British journal of haematology, 128(4), 520-525.
Shapiro, H. M., & Perlmutter, N. G. (2006). Personal cytometers: slow flow or no flow?. Cytometry part A, 69(7), 620-630.
Shapiro, H. M., Schildkraut, E. R., Curbelo, R., Laird, C. W., Turner, B., & Hirschfeld, T. (1976). Combined blood cell counting and classification with fluorochrome stains and flow instrumentation. Journal of Histochemistry & Cytochemistry, 24(1), 396-401.
Shapiro, H. M., Schildkraut, E. R., Curbelo, R., Turner, R. B., Webb, R. H., Brown, D. C., & Block, M. J. (1977). Cytomat-R: a computer-controlled multiple laser source multiparameter flow cytophotometer system. Journal of Histochemistry & Cytochemistry, 25(7), 836-844.
Sheehan, H. L., & Storey, G. W. (1947). An improved method of staining leucocyte granules with Sudan black B. The Journal of pathology and bacteriology, 59(1-2), 336-337.
Simonnet, C., & Groisman, A. (2006). High-throughput and high-resolution flow cytometry in molded microfluidic devices. Analytical chemistry, 78(16), 5653-5663.
Skeggs, L. T., & Hochstrasser, H. (1964). Multiple automatic sequential analysis. Clinical Chemistry, 10(10), 918-936.
Smal, I., Draegestein, K., Galjart, N., Niessen, W., & Meijering, E. (2008). Particle filtering for multiple object tracking in dynamic fluorescence microscopy images: Application to microtubule growth analysis. IEEE transactions on medical imaging, 27(6), 789-804.
Stein, P. D., Hull, R. D., Patel, K. C., & Gould, M. K. (2004). Review: of the various D-dimer assays, negative ELISA results are most useful for excluding a diagnosis of deep venous thrombosis or pulmonary embolism/COMMENTARY. ACP Journal Club, 141(3), 77.
Stein, P. D., Hull, R. D., Patel, K. C., Olson, R. E., Ghali, W. A., Brant, R., . . . & Kalra, N. K. (2004) D-dimer for the exclusion of acute venous thrombosis and pulmonary embolism: a systematic review. Annals of internal medicine, 140(8), 589-602.
Steinkamp, J. A., Romero, A., & Van, M. D. (1973). Multiparameter cell sorting: identification of human leukocytes by acridine orange fluorescence. Acta cytologica, 17(2), 113-117.
Sutherland, D. R., Anderson, L., Keeney, M., Nayar, R., & Chin-Yee, I. A. N. (1996). The ISHAGE guidelines for CD34+ cell determination by flow cytometry. Journal of hematotherapy, 5(3), 213-226.
Tatsumi, N., Tsuda, I., Furota, A., Takubo, T., Hayashi, M., & Matsumoto, H. (1999). Principle of blood cell counter-development of electric impedance method Sysmex Journal International, 9(1; SEAS SUM), 8-20.
Tibbe, A. G., de Grooth, B. G., Greve, J., Liberti, P. A., Dolan, G. J., & Terstappen, L. W. (1999). Optical tracking and detection of immunomagnetically selected and aligned cells. Nature biotechnology, 17(12), 1210.
Tung, Y. C., Zhang, M., Lin, C. T., Kurabayashi, K., & Skerlos, S. J. (2004). PDMS-based opto-fluidic micro flow cytometer with two-color, multi-angle fluorescence detection capability using PIN photodiodes. Sensors and Actuators B: Chemical, 98(2-3), 356-367.
Van Dilla, M. A., Fulwyler, M. J., & Boone, I. U. (1967). Volume distribution and separation of normal human leucocytes. Proceedings of the Society for Experimental Biology and Medicine, 125(2), 367-370.
Wang, C., Smith, B. R., Ault, K. A., & Rinder, H. M. (2002). Reticulated platelets predict platelet count recovery following chemotherapy. Transfusion, 42(3), 368-374.
Weigl, B. H., Bardell, R., Schulte, T., Battrell, F., & Hayenga, J. (2001). Design and rapid prototyping of thin-film laminate-based microfluidic devices. Biomedical Microdevices, 3(4), 267-274.
Westgard, J. O., Carey, R. N., Feldbruegge, D. H., & Jenkins, L. M. (1976). Performance studies on the Technicon"SMAC" analyzer: Precision and comparison of values with methods in routine laboratory service. Clinical chemistry, 22(4), 489-496.
Written Opinion of the International Search Authority dated Jan. 3, 2012 for PCT/IL2011/000296 filed Apr. 11, 2011.
Written Opinion of the International Search Authority dated Jan. 3, 2012 for PCT/IL2013/000092 filed Dec. 17, 2013.
Written Opinion of the International Search Authority dated Apr. 2, 2014 for PCT/IL2013/000093 filed Dec. 17, 2013.
Yang, S. Y., Hsiung, S. K., Hung, Y. C., Chang, C. M., Liao, T. L , & Lee, G. B. (2006). A cell counting/sorting system incorporated with a microfabricated flow cytometer chip. Measurement Science and Technology, 17(7), 2001.
Zhong, C. F., Ye, J. Y., Myc, A., Cao, Z., Kukowska, J., Baker, J. R., & Nomis, T. B. (Oct. 2004). In vivo flow cytometry. In Frontiers in Optics (p. FTuE5) Optical Society of America.

* cited by examiner

The setup for RGB lasters

SYSTEMS AND METHODS FOR DETERMINING A CHEMICAL STATE

CROSS REFERENCE TO RELATED APPLICATIONS

The present invention is a continuation of U.S. patent application Ser. No. 16/010,520, filed on Jun. 18, 2018, which is a continuation of U.S. patent application Ser. No. 15/670,560, filed on Aug. 7, 2017, which is a continuation of U.S. patent application Ser. No. 14/646,395, filed on May 21, 2015, which is a National Stage application of PCT International Application No. PCT/IL2013/000092, which claims priority from U.S. Provisional Patent Application No. 61/737,854, filed on Dec. 17, 2012, from U.S. Provisional Patent Application No. 61/737,856, filed on Dec. 17, 2012, and from U.S. patent application Ser. No. 13/716,246, filed on Dec. 17, 2012, incorporated herein by reference.

FIELD OF THE INVENTION

The present invention relates generally to apparatus and methods for detecting a biological condition, and more specifically to methods and apparatus for detecting a biological condition in small fluid samples.

BACKGROUND OF THE INVENTION

There are numerous medical conditions which are hard to diagnose. Often diagnosis by a physician is based on the physician's observation of combinations of symptoms in a patient. This sometimes leads to misdiagnosis. Furthermore, the patient's response to a treatment, whether drug or other modality is often followed up by physician's observation.

Many laboratory tests are performed in the diagnostic arena on a bodily specimen or fluid to determine a biological condition in a patient. However, these tests are performed off-line in diagnostic laboratories. Often, the laboratory services are only provided during a single 8-hour shift during the day and tend to be labor intensive.

Some prior art publications in the field include, inter alia,

U.S. Pat. No. 8,116,984 to Davis et al., discloses a method of quantifying CD64 and CD163 expression in leukocytes and, specifically to a kit for use with a flow cytometer including a suspension of quantitative fluorescent microbead standards, fluorescent labeled antibodies directed to CD64 and CD163, and analytical software. Hie software is used to take information on the microbead suspension and fluorescent labeled antibodies from a flow cytometer and analyze data, smooth curves, calculate new parameters, provide quality control measures and notify of expiration of the assay system.

Several developments have been published in the microfluidics field, such as: US2006215155A, which describes a flow cell comprising a layered arrangement of three plates (3-5) in which an intermediate plate (4) consisting of a flexible material is inserted between plates (3, 5) consisting of a more solid material, and at least one of the plates comprises at least one recess (15, 17) for receiving fluid, that is bordered by another plate (3, 5) of the layered arrangement. Such recesses are especially microchannels and reaction chambers. According to the invention, the plates are interconnected by means arranged parallel to the plate plane at a distance to the recess, compressing the intermediate plate.

WO 12019599A describes a microfluidic device for transporting a fluid, in particular a micropump or microvalve. The device according to the invention is characterized by films (2, 3), which lie against each other at film surfaces facing each other and are connected to each other in such a way that a transport channel (19) to be formed between the films (2, 3) is defined, and by deflecting apparatuses for forming the transport channel (19) by jointly deflecting the films (2, 3) lying against each other in a direction perpendicular to the film surfaces, wherein a deflecting surface region (12) of the rear film (2) in the deflection direction lies within the deflecting surface region (14) of the front film (3) in the deflection direction defined by the connection (15) between the films (2, 3).

US2012187117A discloses a fluid reservoir, in particular a fluid reservoir to be integrated into a miniaturized flow cell, comprising a reservoir space, which is enclosed by two bodies (6,7) that lie against each other in a fluid-tight manner. According to the invention, in addition to a stored liquid (9), a solid filling body (12) that fills the remaining reservoir space is arranged in the reservoir space. A part of the reservoir space filled by the stored liquid is preferably bounded predominately by one of the two bodies (6,7) and the solid filling body (12).

Typical turnaround times for diagnostic prior art assays are 30-120 minutes. Often, the time lost in waiting for laboratory results can lead to a further deterioration in a patient, and sometimes death. In some cases, the physician has to act without having the laboratory results. This can lead to providing the patient with the wrong treatment. There is thus a need to provide rapid assays to save lives and provide fast correct treatments to a patient. Despite the inventions described hereinabove, there still remains an unmet need to provide improved apparatus and methods for detecting and diagnosing biological conditions in a patient.

There are many other diagnostic tests, such as to water samples, to detect toxins and contaminants that currently have a long turnaround. There still is an unmet need to provide systems, kits and methods to provide quantitative and/or qualitative tests for determining a chemical state.

SUMMARY OF THE INVENTION

It is an object of some aspects of the present invention to provide improved apparatus and methods for detecting a chemical state of a sample.

In some embodiments of the present invention, improved methods, systems, apparatus and kits are provided for detecting and diagnosing a biological condition in a patient.

In other embodiments of the present invention, a method and system are described for providing rapid detection of biological moieties in a sample from a patient.

In further embodiments of the present invention, a method and kit are disclosed for providing detection of biological moieties in a small fluid sample from a patient.

It is an object of some aspects of the present invention to provide improved apparatus and methods for detecting a chemical entity in small fluid samples.

In some embodiments of the present invention, improved rapid methods, apparatus and kits are provided for detecting chemical entities.

In some embodiments of the present invention, improved rapid methods, apparatus and kits are provided for detecting biological entities.

In further embodiments of the present invention, a method and kit are disclosed for providing detection of biological and/or chemical moieties in a small fluid samples.

In further embodiments of the present invention, a microfluidics method, apparatus and kit are disclosed for providing detection of biological and/or chemical moieties in a small fluid samples.

There is thus provided according to an embodiment of the present invention, a self-contained system for performing an assay for determining a chemical state, the system including;
 a. a stationary cartridge for performing the assay therein;
 b. at least one reagent adapted to react with a sample; and
 c. at least one reporter functionality adapted to report a reaction of the at least one reagent with the sample to report a result of the assay;
wherein the at least one reagent, the sample and the at least one reporter functionality are contained within the cartridge.

Additionally, according to an embodiment of the present invention, the assay is a flow cytometric assay.

Furthermore, according to an embodiment of the present invention, the chemical state is a biochemical state.

Moreover, according to an embodiment of the present invention, the biochemical state is indicative of a biological condition.

Further, according to an embodiment of the present invention, the sample is a biological sample.

Yet further, according to an embodiment of the present invention, the biological sample is a bodily sample.

Additionally, according to an embodiment of the present invention, the bodily sample is selected from a the group consisting of blood, serum, plasma, urine, saliva, cerebrospinal fluid (CSF), serous fluid, peritoneal fluid and synovial fluid blood, urine, plasma, serum and saliva.

Importantly, according to an embodiment of the present invention, the cartridge is valveless.

Notably, according to an embodiment of the present invention, the cartridge is a disposable microfluidics cartridge.

Additionally, according to an embodiment of the present invention, the at least one reagent includes at least one of;
 a. at least one target antibody;
 b. at least one positive control identifying antibody; and
 c. at least one negative control identifying detection moiety.

Furthermore, according to an embodiment of the present invention, the at least one reagent includes at least one reference composition including at least one of;
 a. a target signal reference composition; and
 b. a reference identifier composition.

There is thus provided according to another embodiment of the present invention, a method for performing an assay for determining a chemical state in a self-contained stationary cartridge, the method including;
 a. introducing a sample into the cartridge;
 b. reacting at least one reagent with the sample; and
 c. detecting a signal associated with at least one reporter functionality, the at least one reporter functionality adapted to report a reaction of the at least one reagent with the sample, thereby determining the chemical state.

Additionally, according to an embodiment of the present invention, the method further includes forming at least one product and detecting a signal associated with the product.

Moreover, according to an embodiment of the present invention, the assay is a flow cytometric assay.

Furthermore, according to an embodiment of the present invention, the chemical state is a biochemical state.

Notably, according to an embodiment of the present invention, the biochemical state is indicative of a biological condition.

Further, according to an embodiment of the present invention, the sample is a biological sample.

Yet further, according to an embodiment of the present invention, the biological sample is a bodily sample.

Additionally, according to an embodiment of the present invention, the bodily sample is selected from the group consisting of blood, serum, plasma, urine, saliva, cerebrospinal fluid (CSF), serous fluid, peritoneal fluid and synovial fluid.

Furthermore, according to an embodiment of the present invention, the at least one reagent includes;
 a. a cell surface marker;
 b. a cell stain;
 c. a reagent bound to a solid support;
 d. a chemical indicator; and
 e. a biological cell indicator.

Additionally, according to an embodiment of the present invention, the cell surface marker is selected from the group consisting of CD64, CD4, CD8, a stem cell indicator, a Minimal Residual Disease indicator and a lymphocyte subtype indicator.

Moreover, according to an embodiment of the present invention, the cell stain is selected from the group consisting of a white blood cell differential indicator, an apoptosis indicator.

Furthermore, according to an embodiment of the present invention, the reagent bound to the solid support is selected from the group consisting of an immobilized enzyme, an immobilized substrate, a plasma protein bead, an antibody bead, an antigen bead and an ELISA assay.

Further, according to an embodiment of the present invention, the chemical indicator is selected from the group consisting of a color indicator, a turbidity indicator, a pH indicator, an adsorption indicator, an emission indicator and a chemical reaction indicator.

Yet further, according to an embodiment of the present invention, the biological cell indicator is selected from the group consisting of a cell cycle stage indicator, a cell proliferation indicator, a cytokine indicator, a metabolic indicator and an apoptosis indicator.

Additionally, according to an embodiment of the present invention, the at least one reagent includes at least two reagents.

Furthermore, according to an embodiment of the present invention, the at least two reagents include at least one of;
 a. a cell surface marker and a cell element stain;
 b. a cell surface marker and a plasma protein bead assay;
 c. a cell surface marker and a solution change marker;
 d. a cell element stain and a plasma protein bead assay; and
 e. a cell element stain and a solution change marker.

Additionally, according to an embodiment of the present invention, the biological condition is selected from blood diseases such as leukemia, thrombocytopenia immune system disorders, local infections, urinary tract disorders, autoimmune diseases and sepsis.

There is thus provided, according to an additional embodiment of the present invention, a method for forming a chemical reaction in a stationary cartridge, the method including;
 a. storing at least one composition in the cartridge; and
 b. activating at least one inflatable chamber to provide at least one pressure force to the at least one composition thereby inducing the chemical reaction.

Additionally, according to an embodiment of the present invention, the cartridge is a valveless cartridge.

Additionally, according to an embodiment of the present invention, the at least one composition includes at least two compositions.

Furthermore, according to an embodiment of the present invention, the at least one pressure force is a positive pressure force.

Further, according to an embodiment of the present invention, the at least one pressure force is a negative pressure force.

Importantly, according to an embodiment of the present invention, the at least one pressure force includes at least one positive pressure force and at least one negative pressure force.

Additionally, according to an embodiment of the present invention, the at least one positive pressure force and at least one negative pressure force include alternating positive and negative pressure forces.

Furthermore, according to an embodiment of the present invention, the at least one inflatable chamber includes two one inflatable chambers.

Further, according to an embodiment of the present invention, the chemical reaction includes at least one intermediate.

Additionally, according to an embodiment of the present invention, the at least one pressure force is provided sequentially to a several combinations of compositions of the at least one composition.

According to an embodiment of the present invention, the method further includes introducing a specimen to the cartridge before the activating step.

Additionally, according to an embodiment of the present invention, the specimen is a bodily sample.

Moreover, according to an embodiment of the present invention, the chemical reaction provides a flow cytometric assay result to the bodily sample.

Furthermore, according to an embodiment of the present invention, the chemical reaction is for determining a biological condition in a mammalian subject.

Additionally, according to an embodiment of the present invention, the method further includes;
  c. incubating a specimen from the subject in the cartridge for a predetermined period of time; and
  d. receiving an indication responsive to at least one reporter element thereby providing the indication of the biological condition in the subject.

Additionally, according to an embodiment of the present invention, the biological condition is selected from blood diseases such as leukemia, thrombocytopenia immune system disorders, local infections, urinary tract disorders, autoimmune diseases and sepsis.

Furthermore, according to an embodiment of the present invention, at least one composition disposed in the cartridge includes a sepsis biomarker.

Further, according to an embodiment of the present invention, the biomarker includes at least one of CD64 and CD 163.

Additionally, according to an embodiment of the present invention, the indication is quantitative.

Importantly, according to an embodiment of the present invention, the sample is of a volume of less than 200 microliters (μL).

Additionally notably, according to an embodiment of the present invention, the method is completed within twenty minutes. In some cases, the method is completed within fifteen minutes, ten minutes or five minutes.

There is thus provided according to an embodiment of the present invention, a method for determining a biological condition in a mammalian subject, the method including;
  a. incubating a specimen from the subject with at least one composition in a stationary cartridge as described herein, for a predetermined period of time to form at least one reaction product, when the subject has the biological condition; and
  b. receiving an indication of the at least one reaction product responsive to at least one reporter element in the method thereby providing the indication of the biological condition in the subject.

There is thus provided according to an embodiment of the present invention, a microfluidics kit for detecting a chemical entity, the kit comprising;
  a. a disposable element for receiving a sample and for combining said sample with at least one composition;
  b. at least one composition comprising at least one detector moiety adapted to react with said sample to form a reaction product; and
  c. at least one reporter element adapted to provide an indication of reaction product thereby providing the indication of the presence of the chemical entity.

Additionally, according to an embodiment of the present invention, the kit further comprises;
  a. instructions for using the kit.

There is thus provided according to an embodiment of the present invention, a kit for evaluating a biological condition in a patient, the kit comprising;
  a. a disposable element for receiving a biological specimen and for combining said specimen with at least one composition;
  b. at least one composition comprising at least one detector moiety adapted to react with said specimen to form a reaction product, when said patient has said biological condition; and
  c. at least one reporter element adapted to provide an indication of reaction product thereby providing the indication of the biological condition.

Additionally, according to an embodiment of the present invention, the kit further comprises;
  a. instructions for using the kit.

Furthermore, according to an embodiment of the present invention, the disposable element is a disposable cartridge.

Moreover, according to an embodiment of the present invention, the disposable cartridge is a disposable microfluidics cartridge.

Additionally, according to an embodiment of the present invention, the disposable microfluidics cartridge comprises at least one of the following elements;
  a) a reservoir;
  b) a pump;
  c) a conduit;
  d) a miniaturized flow cell;
  e) a transport channel;
  f) a microfluidic element;
  g) a compressed gas holding element
  h) a compressed gas releasing element;
  i) a nozzle element;
  j) a mixing element;
  k) a bellows element;
  l) software adapted to activate said elements according to a specific sequence; and
  m) hardware to activate said elements according to a specific sequence.

Additionally, according to an embodiment of the present invention, the disposable microfluidics cartridge comprises at least two of the elements.

Additionally, according to an embodiment of the present invention, the disposable microfluidics cartridge comprises at least three of the elements.

Additionally, according to an embodiment of the present invention, the disposable microfluidics cartridge comprises at least four of the elements.

Additionally, according to an embodiment of the present invention, the disposable microfluidics cartridge comprises at least five of the elements.

Additionally, according to an embodiment of the present invention, the disposable microfluidics cartridge comprises at least ten of the elements.

Additionally, according to an embodiment of the present invention, the disposable microfluidics cartridge comprises at least twenty of the elements.

Additionally, according to an embodiment of the present invention, the disposable microfluidics cartridge comprises at least thirty of the elements.

According to an embodiment of the present invention, the microfluidics kit is configured to provide the rapid indication with one hour.

According to another embodiment of the present invention, the microfluidics kit is configured to provide the rapid indication with thirty minutes.

According to another embodiment of the present invention, the microfluidics kit is configured to provide the rapid indication with fifteen minutes.

According to another embodiment of the present invention, the microfluidics kit is configured to provide the rapid indication with ten minutes.

According to another embodiment of the present invention, the microfluidics kit is configured to provide the rapid indication with five minutes.

According to another embodiment of the present invention, the microfluidics kit is configured to provide the rapid indication with one minute.

According to another embodiment of the present invention, the microfluidics kit is configured to provide the rapid indication with thirty seconds.

According to another embodiment of the present invention, the microfluidics kit is configured to provide the rapid indication with ten seconds.

According to another embodiment of the present invention, the microfluidics kit is configured to provide the rapid indication with one second.

There is thus provided according to an embodiment of the present invention, a microfluidics assay kit for performing a rapid biological assay, the kit comprising;
  a) a disposable element comprising a reactant, the disposable element being adapted to receive a sample comprising a biological entity and for combining said reactant with said biological entity to form a reaction product; and
  b) at least one reporter element adapted to provide a rapid indication of disappearance of said reactant thereby providing rapid assay of the biological entity.

There is thus provided according to an embodiment of the present invention, a microfluidics assay kit for performing a rapid assay of a biological entity, the kit comprising;
  a) a disposable element comprising a reactant, the disposable element being adapted to receive a sample comprising the biological entity and for combining said reactant with said biological entity to form a reaction product; and
  b) at least one reporter element adapted to provide a rapid indication of appearance of said reaction product thereby providing rapid assay of the biological entity.

There is thus provided according to an embodiment of the present invention, a composition for evaluating a biological condition, the composition comprising;
  a. a sample composition comprising at least one of;
    i. a bodily specimen comprising a target moiety;
    ii. a positive control moiety; and
    iii. a negative control moiety;
  b. a detection composition comprising at least one of;
    i. at least one target antibody;
    ii. at least one positive control identifying antibody; and
    iii. at least one negative control identifying detection moiety or characteristic; and
  c. at least one reference composition comprising at least one of;
    i. a target signal reference composition; and
    ii. a reference identifier composition.

There is thus provided according to another embodiment of the present invention a composition for evaluating a biological condition, the composition comprising;
  a. a sample composition comprising at least one of;
    i. a bodily specimen comprising a target moiety;
    ii. a positive control moiety; and
    iii. a negative control moiety;
  b. an antibody composition comprising at least one of;
    i. at least one target antibody (CD64 antibody);
    ii. at least one positive control identifying antibody (CD163); and
    iii. at least one negative control identifying antibody or characteristic; and
  c. at least one reference composition comprising at least one of;
    i. a target signal reference composition; and
    ii. a reference identifier composition.

Additionally, according to an embodiment of the present invention, the composition further comprises at least one conditioning moiety comprising;
  d. at least one lysis reagent; and
  e. at least one diluent.

Furthermore, according to an embodiment of the present invention, biological the condition is selected from a group consisting of blood diseases such as leukemia, thrombocytopenia immune system disorders, local infections, urinary tract disorders, autoimmune diseases and sepsis.

Moreover, according to an embodiment of the present invention the bodily specimen is selected from a group consisting of blood, serum, plasma, urine, saliva, cerebrospinal fluid (CSF), serous fluid, peritoneal fluid and synovial fluid.

According to another embodiment of the present invention, the target moiety includes a CD64 surface antigen on neutrophils.

Additionally, according to a further embodiment of the present invention, the positive control moiety includes monocytes and the negative control includes lymphocytes.

Additionally, according to an embodiment of the present invention, the target moiety is CD64 on neutrophils, the positive control moiety includes CD64 expression on monocytes, and the negative control moiety includes lymphocytes without CD64 expression.

Further, according to an embodiment of the present invention, the target indicator is bound to a signaling moiety on the at least one target antibody.

Yet further, according to an embodiment of the present invention, the at least one reference composition includes beads.

Additionally, according to an embodiment of the present invention, the beads include polystyrene microbeads.

Moreover, according to an embodiment of the present invention, the target antibody reference composition includes a first fluorescent signal and the reference identifier composition includes a second fluorescent signal.

Furthermore, according to an embodiment of the present invention, the first fluorescent signal includes FITC and the second fluorescent signal includes Starfire Red fluor.

There is thus provided according to an embodiment of the present invention, a method of quantifying a biomarker in a sample, comprising;
  a. contacting the sample with a fluorescently-labeled binding moiety that specifically binds to the biomarker;
  b. detecting a first fluorescent signal from at least a portion of the labeled sample;
  c. detecting a second fluorescent signal from a population of fluorescently-labeled particles, wherein the population includes a known fluorescent intensity over a fixed time; and
  d. normalizing the first fluorescent signal to the second fluorescent signal, thereby quantifying the biomarker, wherein the normalizing includes using a device comprising software capable of comparing the first and second fluorescent signal.

Furthermore, according to an embodiment of the present invention, the biomarker is a sepsis biomarker.

Moreover, according to an embodiment of the present invention, the biomarker is CD64 or CD163.

Additionally, according to an embodiment of the present invention, the sample is a blood sample.

According to another embodiment of the present invention, the fluorescent label of the binding moiety and the fluorescent label of the particles is the same fluorescent label.

Further, according to an embodiment of the present invention, the binding moiety is an antibody.

According to an embodiment of the present invention, the software is capable of recognizing a specific lot of fluorescently-labeled particles.

Moreover, according to an embodiment of the present invention, the individual fluorescent signals include at least one first fluorescent signal and at least one second fluorescent signal.

Additionally, according to an embodiment of the present invention the fluorescently-labeled binding moiety targets a first cell population and a second cell population in the sample.

According to another embodiment of the present invention the detection of binding of the binding moiety to the second cell population provides an internal positive control for the sample.

Furthermore, according to an embodiment of the present invention, the binding moiety is anti-CD64 antibody and the first cell population includes neutrophil leukocytes.

Yet further, according to an embodiment of the present invention, the second cell population includes monocytes.

According to an embodiment of the present invention, the method further comprises the step of determining the presence of at least one cell population in the sample that is not bound by the binding moiety, thus providing an internal negative control for the sample.

There is thus provided according to another embodiment of the present invention, a composition for evaluating a biological condition, the composition comprising;
  a. a sample comprising at least one of;
    i. a bodily specimen comprising a target moiety;
    ii. a positive control moiety; and
    iii. a negative control moiety;
  b. an antibody composition comprising at least one of;
    i. at least one target antibody (cd64 antibody);
    ii. at least one positive control identifying antibody (CD 163); and
    iii. at least one negative control identifying antibody or characteristic (scatter); and
  c. at least one reference composition (beads) comprising at least one of;
    i. a target antibody reference composition; and
    ii. a reference identifier composition.

According to an embodiment of the present invention, the composition further comprises at least one conditioning moiety comprising;
  a. at least one lysis reagent; and
  b. at least one diluent.

There is thus provided according to another embodiment of the present invention, a method of determining the presence or absence of sepsis in a subject, the method including:
  a) contacting a blood sample from the subject with a fluorescently-labeled binding moiety specific to a sepsis marker, wherein the volume of the blood sample is 50 μL or smaller; and
  b) detecting the presence, absence or level of the binding moiety in the sample, thereby determining the presence or absence of sepsis in the subject.

There is thus provided according to another embodiment of the present invention, a method of quantifying a biomarker in a sample, comprising;
  a) contacting the sample with a fluorescently-labeled binding moiety that specifically binds to the biomarker;
  b) detecting a first fluorescent signal from at least a portion of the labeled sample;
  c) detecting a second fluorescent signal from a population of fluorescently-labeled particles, wherein the population includes a known fluorescent intensity over a fixed time; and
  d) normalizing the first fluorescent signal to the second fluorescent signal, thereby quantifying the biomarker, wherein the normalizing includes using a device comprising software capable of comparing the first and second fluorescent signal.

There is thus provided according to an embodiment of the present invention, a method of quantifying a second biomarker in a sample, comprising;
  a. contacting the sample with a first fluorescently-labeled binding moiety that specifically binds to a first biomarker;
  b. contacting the sample with a second fluorescently-labeled binding moiety that specifically binds to a second biomarker;
  c. detecting a first fluorescent signal from at least a portion of the labeled sample;
  d. detecting a second fluorescent signal from a population of fluorescently-labeled particles, wherein the population includes a known fluorescent intensity over a fixed time; and
  e. normalizing the first fluorescent signal to the second fluorescent signal, thereby quantifying the second biomarker, wherein the normalizing includes using a device comprising software capable of comparing the first and second fluorescent signal.

According to some embodiments, the sample may be liquid, according to other embodiments, the sample may be a colloid or suspension. According to further embodiments, the sample may be a solid, such as in a powder or crystal form.

There is thus provided according to an embodiment of the present invention, a microfluidics kit for performing a chemical reaction, the kit comprising;
a) a disposable element for receiving a sample and for combining said sample with at least one composition;
b) at least one composition comprising at least one detector moiety adapted to react with said sample to form a reaction product; and
c) at least one reporter element adapted to provide an indication of said reaction product.

There is thus provided according to an embodiment of the present invention, a microfluidics kit for performing a chemical reaction, the kit comprising;
a) a disposable element for receiving a sample and for combining said sample with at least one composition;
b) at least one composition comprising at least one detector moiety adapted to react with said sample to form a reaction product; and
c) at least one reporter element adapted to provide an indication of disappearance of a reactant in said sample thereby providing the indication of the presence of the reaction product.

There is thus provided according to an embodiment of the present invention, a microfluidics kit for performing a chemical reaction, the kit comprising;
a) a disposable element for receiving a first reactant and for combining said first reactant with at least one composition;
b) at least one composition comprising at least one detector moiety adapted to react with a reaction product; and
c) at least one reporter element adapted to provide an indication said of at least one detector moiety thereby providing the indication of the presence of the reaction product.

There is thus provided according to an embodiment of the present invention, a microfluidics kit for performing a rapid detection of a chemical entity, the kit comprising;
a) a disposable element for receiving a first reactant and for combining said sample with at least one composition;
b) at least one composition comprising at least one detector moiety adapted to react with a reaction product; and
c) at least one reporter element adapted to provide a rapid indication said of at least one detector moiety thereby providing rapid detection of the chemical entity.

There is thus provided according to an embodiment of the present invention, a microfluidics kit for performing a rapid detection of a chemical entity, the kit comprising;
a) a disposable element for receiving a first reactant and for combining said sample with at least one composition to form a reaction product;
b) at least one detector moiety adapted to react with a reaction product; and
c) at least one reporter element adapted to provide a rapid indication said of at least one detector moiety thereby providing rapid detection of the chemical entity.

There is thus provided according to an embodiment of the present invention, a microfluidics kit for performing a rapid detection of a chemical entity, the kit comprising;
a) a disposable element for receiving a first reactant and for combining said sample with at least one composition to form a reaction product; and
b) at least one reporter element adapted to provide a rapid indication said of reaction product thereby providing rapid detection of the chemical entity.

There is thus provided according to an embodiment of the present invention, a microfluidics kit for performing a rapid detection of a chemical entity, the kit comprising;
a) a disposable element for receiving a first reactant and for combining said sample with at least one composition to form a reaction product; and
b) at least one reporter element adapted to provide a rapid indication of disappearance of said chemical entity thereby providing rapid detection of the chemical entity.

According to an embodiment of the present invention, the microfluidics kit is configured to provide the rapid indication with one hour.

According to another embodiment of the present invention, the microfluidics kit is configured to provide the rapid indication with thirty minutes.

According to another embodiment of the present invention, the microfluidics kit is configured to provide the rapid indication with fifteen minutes.

According to another embodiment of the present invention, the microfluidics kit is configured to provide the rapid indication with ten minutes.

According to another embodiment of the present invention, the microfluidics kit is configured to provide the rapid indication with five minutes.

According to another embodiment of the present invention, the microfluidics kit is configured to provide the rapid indication with one minute.

According to another embodiment of the present invention, the microfluidics kit is configured to provide the rapid indication with thirty seconds.

According to another embodiment of the present invention, the microfluidics kit is configured to provide the rapid indication with ten seconds.

According to another embodiment of the present invention, the microfluidics kit is configured to provide the rapid indication with one second.

There is thus provided according to an embodiment of the present invention, a microfluidics kit for performing a rapid detection of a chemical entity, the kit comprising;
a) a disposable element for receiving a first reactant and for combining said sample with at least one composition to form a reaction product; and
b) at least one reporter element adapted to provide a rapid indication said of reaction product thereby providing rapid detection of the chemical entity.

There is thus provided according to an embodiment of the present invention, a microfluidics kit for performing a rapid detection of a chemical entity, the kit comprising;
a) a disposable element for receiving a first reactant and for combining said sample with at least one composition to form a reaction product; and
b) at least one reporter element adapted to provide a rapid indication of disappearance of said chemical entity thereby providing rapid detection of the chemical entity.

There is thus provided according to an embodiment of the present invention, a microfluidics assay kit for assaying a chemical entity, the kit comprising;
   a) a disposable element for receiving a sample and for combining said sample with at least one composition;
   b) at least one composition comprising at least one detector moiety adapted to react with said sample to form a reaction product; and
   c) at least one reporter element adapted to provide an indication of reaction product thereby providing the assay of the chemical entity.

Additionally, according to an embodiment of the present invention, the kit further comprises;
   d) instructions for using the kit.

Furthermore, according to an embodiment of the present invention, the disposable element is a disposable cartridge.

Moreover, according to an embodiment of the present invention, the disposable cartridge is a disposable microfluidics cartridge.

There is thus provided according to another embodiment of the present invention, a method of quantifying a biomarker in a sample, comprising;
   a) contacting the sample with a fluorescently-labeled binding moiety that specifically binds to the biomarker;
   b) detecting a first fluorescent signal from at least a portion of the labeled sample;
   c) detecting a second fluorescent signal from a population of fluorescently-labeled particles, wherein the population includes a known fluorescent intensity over a fixed time; and
   d) normalizing the first fluorescent signal to the second fluorescent signal, thereby quantifying the biomarker, wherein the normalizing includes using a device comprising software capable of comparing the first and second fluorescent signal.

There is thus provided according to an embodiment of the present invention, a method of quantifying a second biomarker in a sample, comprising;
   a. contacting the sample with a first fluorescently-labeled binding moiety that specifically binds to a first biomarker;
   b. contacting the sample with a second fluorescently-labeled binding moiety that specifically binds to a second biomarker;
   c. detecting a first fluorescent signal from at least a portion of the labeled sample;
   d. detecting a second fluorescent signal from a population of fluorescently-labeled particles, wherein the population includes a known fluorescent intensity over a fixed time; and
   e. normalizing the first fluorescent signal to the second fluorescent signal, thereby quantifying the second biomarker, wherein the normalizing includes using a device comprising software capable of comparing the first and second fluorescent signal.

There is thus provided according to an embodiment of the present invention, a method for performing a microfluidic chemical reaction on a sample, the method comprising;
   a) combining the sample with at least one composition comprising at least one detector moiety adapted to react with said sample to form a reaction product; and
   b) detecting said at least one detector moiety to provide an indication of said reaction product.

There is thus provided according to an embodiment of the present invention, a method for performing a chemical reaction on a microfluidic scale, the method comprising;
   a) receiving a sample into a microfluidic element;
   b) combining said sample with at least one composition comprising at least one detector moiety disposed in said microfluidic element; and
   c) detecting said at least one detector moiety.

There is thus provided according to an embodiment of the present invention, a method for performing a chemical reaction on a microfluidic scale, the method comprising;
   a) reacting a sample with at least one composition disposed in a microfluidics element to form a reaction product in said microfluidics element; and
   b) detecting at least one detector moiety adapted to react with said sample to provide an indication of appearance of said reaction product thereby providing the indication of the chemical reaction.

There is thus provided according to an embodiment of the present invention, a method for performing a chemical reaction, the method comprising;
   a) receiving a first reactant in a microfluidics disposable element;
   b) combining said first reactant with at least one composition comprising at least one detector moiety to form a reaction product, said detector moiety being adapted to react with a reaction product; and
   c) providing an indication of said chemical reaction responsive to said detector moiety.

There is thus provided according to an embodiment of the present invention, a method for performing a chemical reaction, the method comprising;
   a) receiving a first reactant in a microfluidics disposable element;
   b) combining said first reactant with at least one composition comprising at least one detector moiety to form a reaction product, said detector moiety being adapted to react with the first reactant product; and
   c) providing an indication of said chemical reaction responsive to said detector moiety.

There is thus provided according to an embodiment of the present invention, a method for performing a rapid detection of a chemical entity, the method comprising;
   a) receiving a sample comprising a first reactant in a disposable element;
   b) reacting said sample with a composition disposed in said disposable element to form at least one reaction product; and
   c) detecting said disappearance of said first reactant responsive to activation of a reporter element disposed in said disposable element thereby providing rapid detection of said chemical entity.

There is thus provided according to an embodiment of the present invention, a method for performing a rapid detection of a chemical entity, the method comprising;
   a) receiving a said sample comprising the chemical entity into a disposable element;
   b) reacting at least part of the sample with at least one composition disposed in said disposable element to form at least one reaction product; and
   c) detecting at least one detector moiety in said at least one composition responsive to said reacting step thereby detecting said chemical entity.

There is thus provided according to an embodiment of the present invention, a method for performing a rapid detection of a chemical entity, the method comprising;
   a) receiving a sample comprising a first reactant in a disposable element;
   b) combining said sample with at least one composition disposed in said disposable element to form a reaction product; and c) detecting at least one detector moiety disposed in said disposable element, said at least one detector moiety being adapted to react with a reaction product thereby providing rapid detection of the chemical entity.

There is thus provided according to an embodiment of the present invention, a method for performing a rapid detection of a chemical entity, the method comprising;
 a) receiving a first reactant in a sample into a disposable element;
 b) reacting at least one composition with at least part of said sample to form a reaction product; and
 c) detecting at least one reporter element disposed in said disposable element, said at least one reporter element being adapted to provide a rapid indication said of reaction product thereby providing rapid detection of the chemical entity.

There is thus provided according to an embodiment of the present invention, a method for performing a rapid detection of a chemical entity, the method comprising;
 a) receiving a first reactant in a sample into a microfluidics element;
 b) reacting at least part of said sample with at least one composition disposed in said microfluidics element to form a reaction product; and
 c) detecting at least one reporter element disposed in said microfluidics element, said at least one reporter element being adapted to provide a rapid indication of disappearance of said chemical entity thereby providing rapid detection of the chemical entity.

According to an embodiment of the present invention, the microfluidics method is configured to provide the rapid indication with one hour.

According to another embodiment of the present invention, the microfluidics method is configured to provide the rapid indication with thirty minutes.

According to another embodiment of the present invention, the microfluidics method is configured to provide the rapid indication with fifteen minutes.

According to another embodiment of the present invention, the microfluidics method is configured to provide the rapid indication with ten minutes.

According to another embodiment of the present invention, the microfluidics method is configured to provide the rapid indication with five minutes.

According to another embodiment of the present invention, the microfluidics method is configured to provide the rapid indication with one minute.

According to another embodiment of the present invention, the microfluidics method is configured to provide the rapid indication with thirty seconds.

According to another embodiment of the present invention, the microfluidics method is configured to provide the rapid indication with ten seconds.

According to another embodiment of the present invention, the microfluidics method is configured to provide the rapid indication with one second.

There is thus provided according to an embodiment of the present invention, a microfluidics method for performing a rapid detection of a biological entity, the method comprising;
 a) receiving a sample comprising a biological entity into a disposable element comprising a reactant;
 b) reacting said sample with said reactant to form a reaction product; and
 c) detecting at least one reporter element in said disposable element thereby providing a rapid indication of disappearance of said reactant so as to provide rapid detection of the biological entity.

There is thus provided according to an embodiment of the present invention, a microfluidics method for performing a rapid detection of a biological entity, the method comprising;
 a) receiving a sample comprising a biological entity into a disposable element comprising a reactant;
 b) reacting said sample with said reactant to form a reaction product; and
 c) detecting at least one reporter element in said disposable element thereby providing a rapid indication of appearance of said reaction product so as to provide rapid detection of the biological entity.

There is thus provided according to an embodiment of the present invention, a microfluidics method for performing a rapid detection of a chemical entity, the method comprising;
 a) receiving a sample comprising a first reactant into a disposable element;
 b) combining at least part of said sample with at least one composition in said disposable element to form a reaction product;
 c) reacting at least one detector moiety, disposed in said disposable element with said reaction product; and
 d) detecting said at least one detector moiety thereby providing rapid detection of the chemical entity.

There is thus provided according to an embodiment of the present invention, a microfluidics method for performing a rapid detection of a chemical entity, the method comprising;
 a) a receiving a sample comprising a first reactant into a disposable element;
 b) combining said sample with at least one composition to form a reaction product; and
 c) detecting at least one reporter element, said at least one reporter element being adapted to provide a rapid indication said of reaction product thereby providing rapid detection of the chemical entity.

There is thus provided according to an embodiment of the present invention, a microfluidics method for performing a rapid detection of a chemical entity, the method comprising;
 a) receiving a sample comprising a first reactant into a disposable element;
 b) combining said sample with at least one composition, disposed in said disposable element, to form a reaction product; and
 c) detecting at least one reporter element adapted to provide a rapid indication of disappearance of said chemical entity thereby providing rapid detection of the chemical entity.

According to some embodiments, the sample may be liquid, according to other embodiments, the sample may be a colloid or suspension. According to further embodiments, the sample may be a solid, such as in a powder or crystal form.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified schematic illustration showing an apparatus for detecting a biological condition, in accordance with an embodiment of the present invention;

FIG. 2 is a simplified flow chart of a method for detecting a biological condition, in accordance with an embodiment of the present invention;

FIG. 3 is a simplified schematic illustration showing a methodology for detecting a biological condition associated with a CD64 cell surface antigen, in accordance with an embodiment of the present invention;

FIG. 4 is a simplified flow chart of a method for detecting a biological condition associated with a CD64 cell surface antigen, in accordance with an embodiment of the present invention;

FIG. 5A is a graphical output of a fluorescent detection assay of a non-activated neutrophil signature associated with the method of FIGS. 3-4, in accordance with an embodiment of the present invention;

FIG. 5B is a graphical output of a fluorescent detection assay of an activated neutrophil signature, associated with the method of FIGS. 3-4, in accordance with an embodiment of the present invention;

FIG. 5C is a graphical output of a fluorescent detection assay of a monocyte signature, associated with the method of FIGS. 3-4, in accordance with an embodiment of the present invention;

FIG. 5D is a graphical output of a fluorescent detection assay of a reference bead signature, associated with the method of FIGS. 3-4, in accordance with an embodiment of the present invention;

FIG. 6 is a simplified schematic illustration showing a methodology for detecting a biological condition associated with a plasma protein, in accordance with an embodiment of the present invention;

FIG. 7 is a simplified flow chart of a method for detecting a biological condition associated with a plasma protein, in accordance with an embodiment of the present invention;

FIG. 8A is a graphical output of a fluorescent detection assay of plasma protein beads with a no target binding signature, associated with the method of FIGS. 6-7, in accordance with an embodiment of the present invention;

Figure 6:
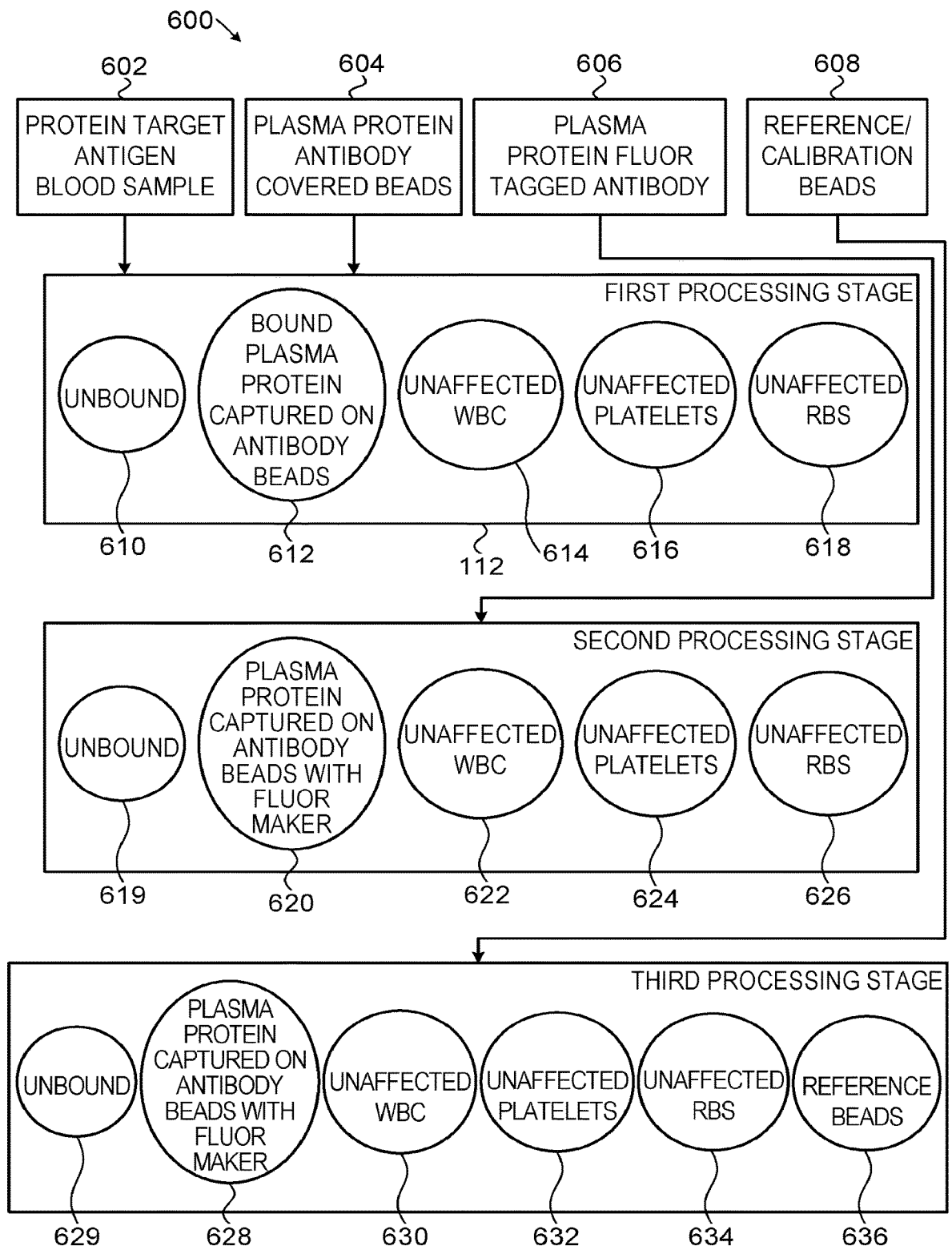
Figure 7:
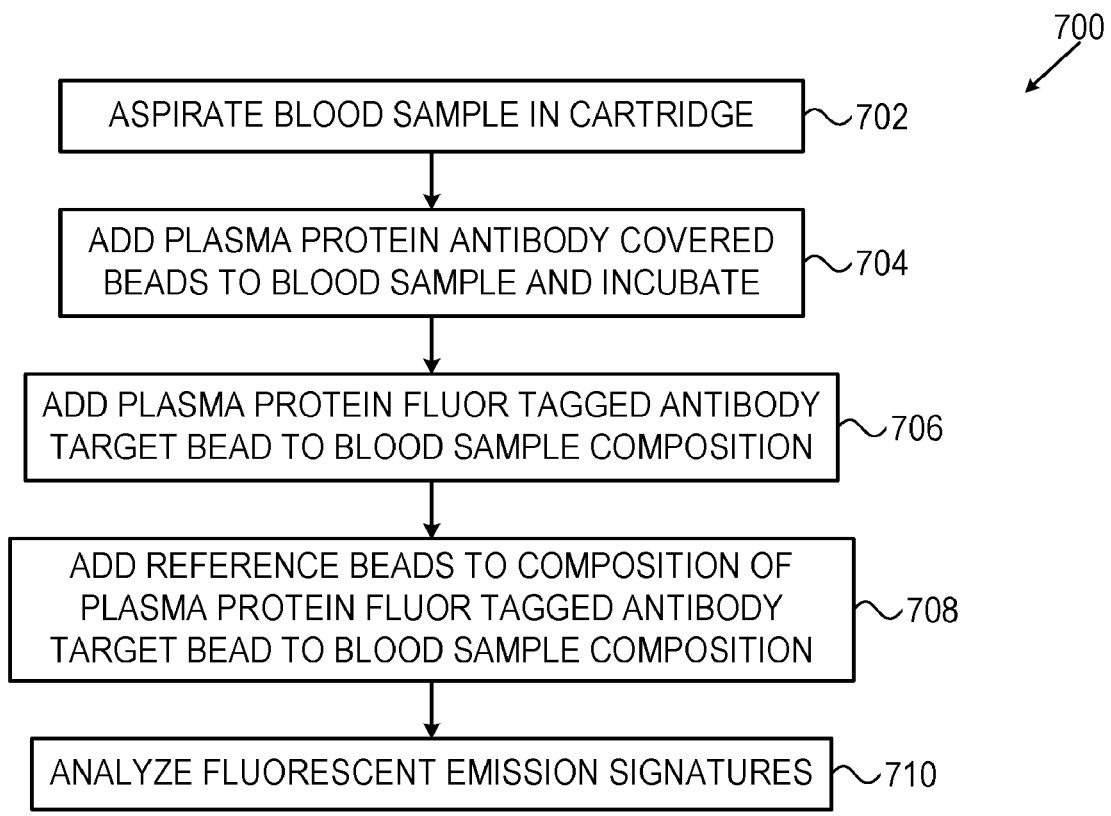
Figure 8A:
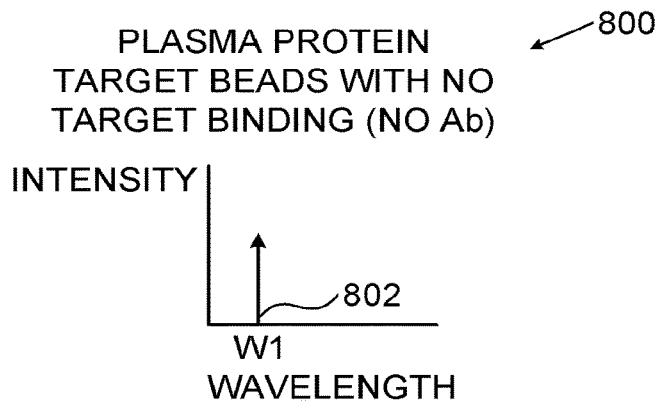
Figure 8B:
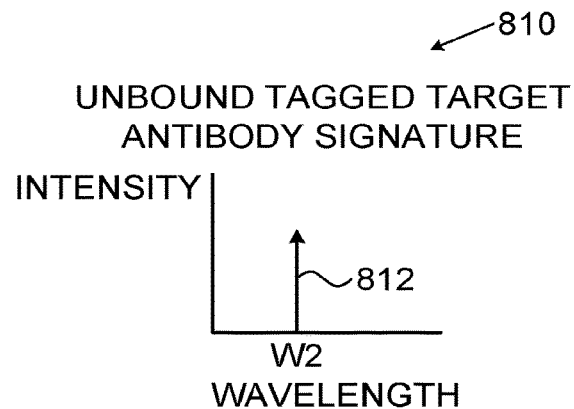
Figure 8C:
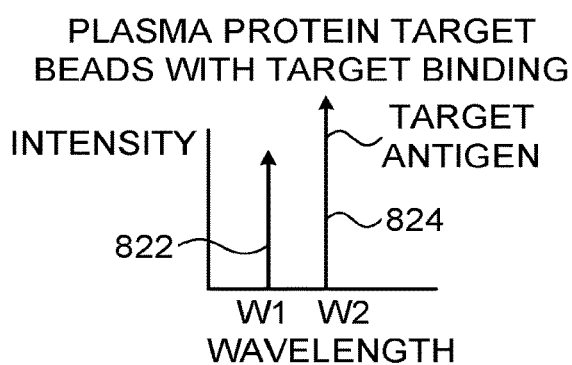
Figure 8D:
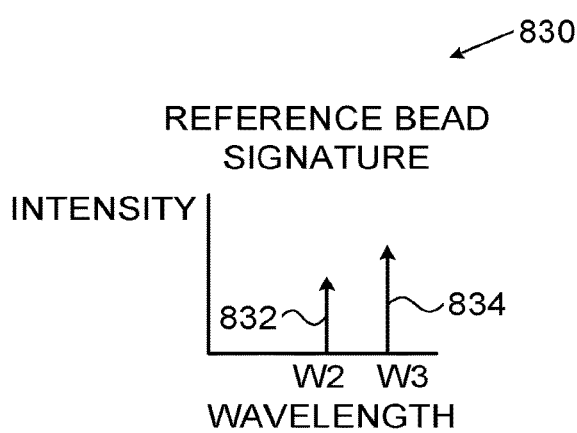
Figure 9:
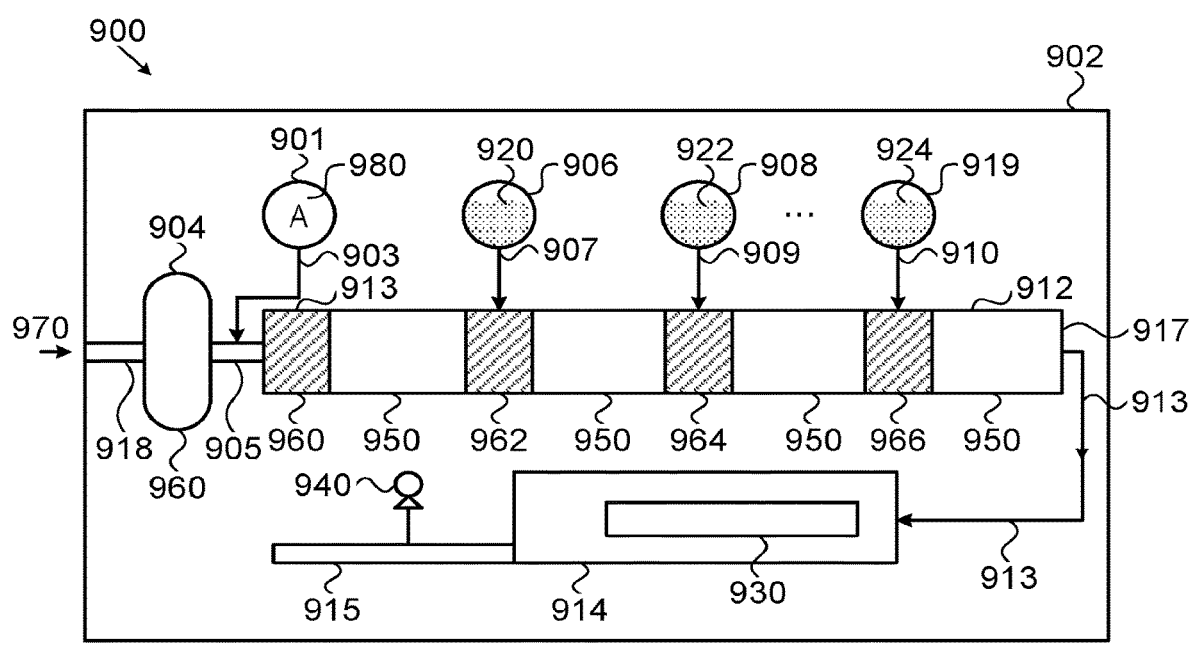
Figure 10:
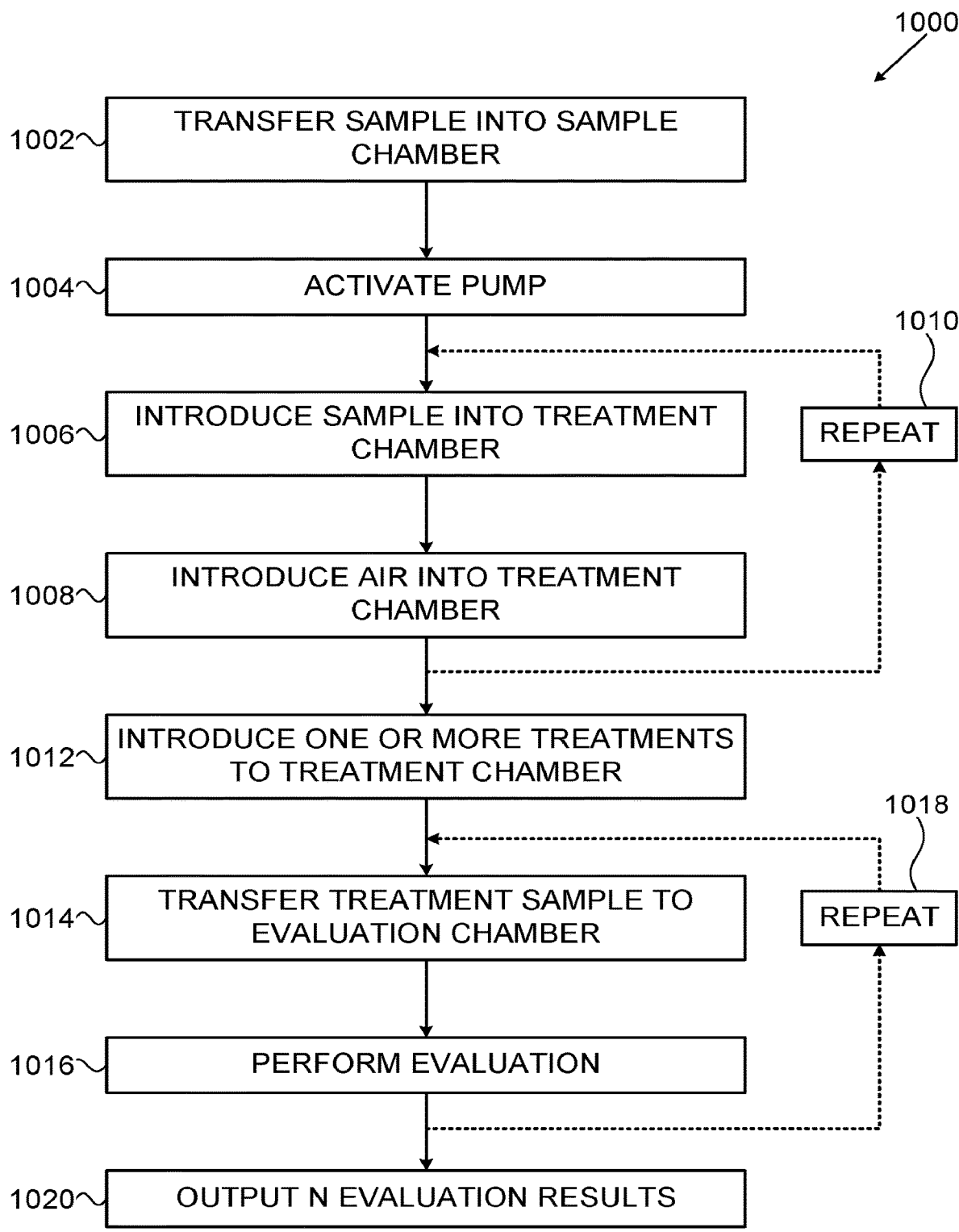
Figure 11:
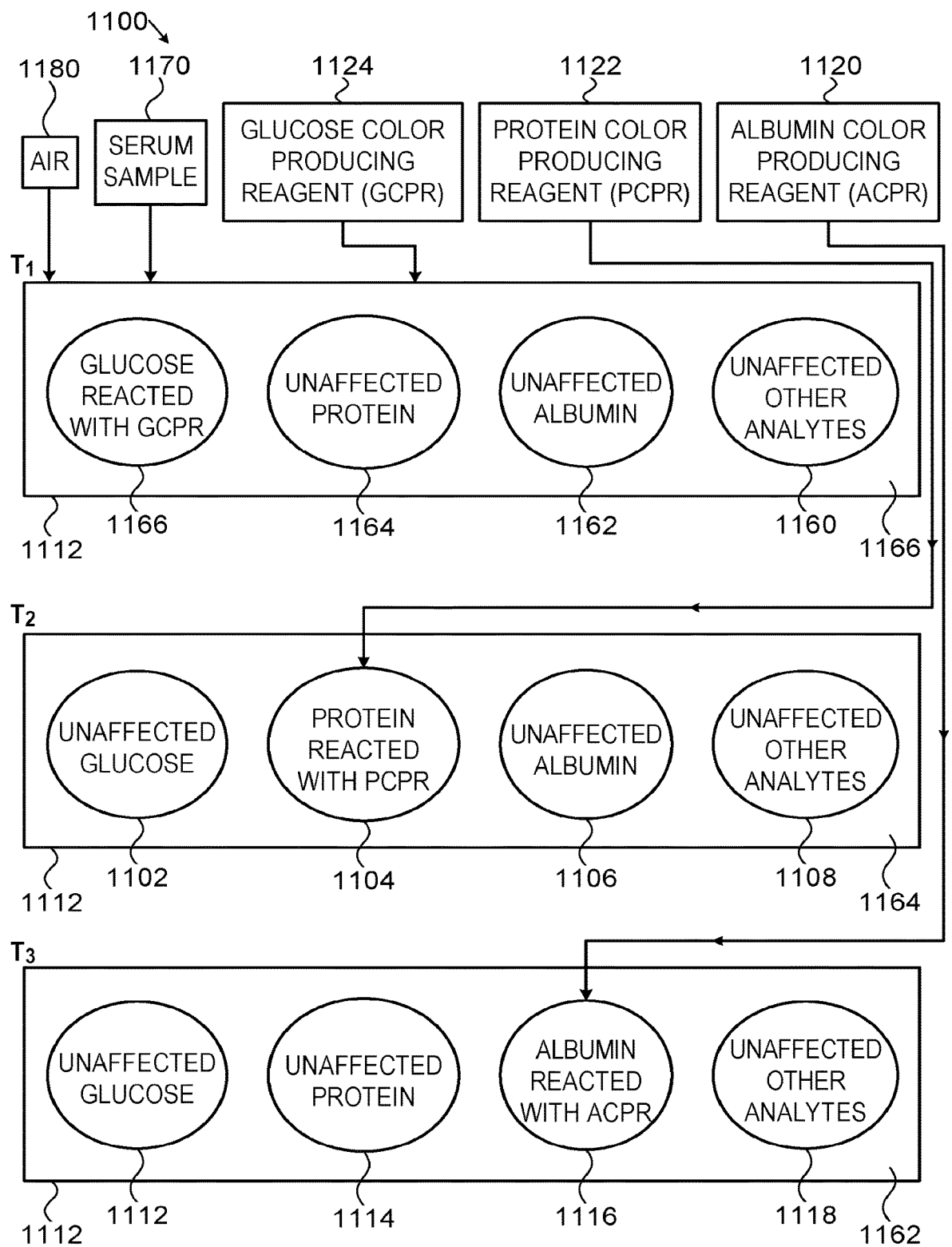
Figure 12A:
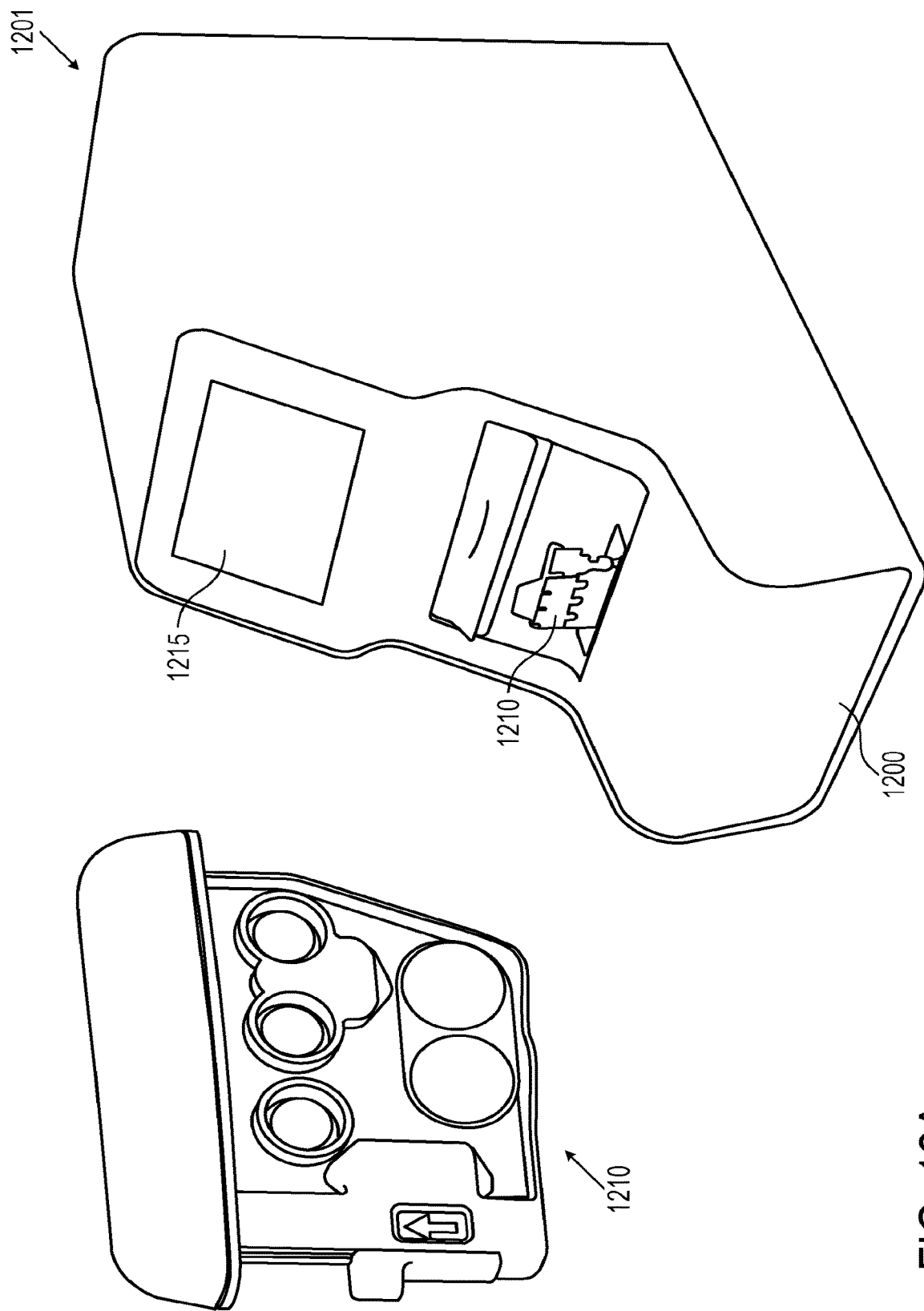
Figure 12C:
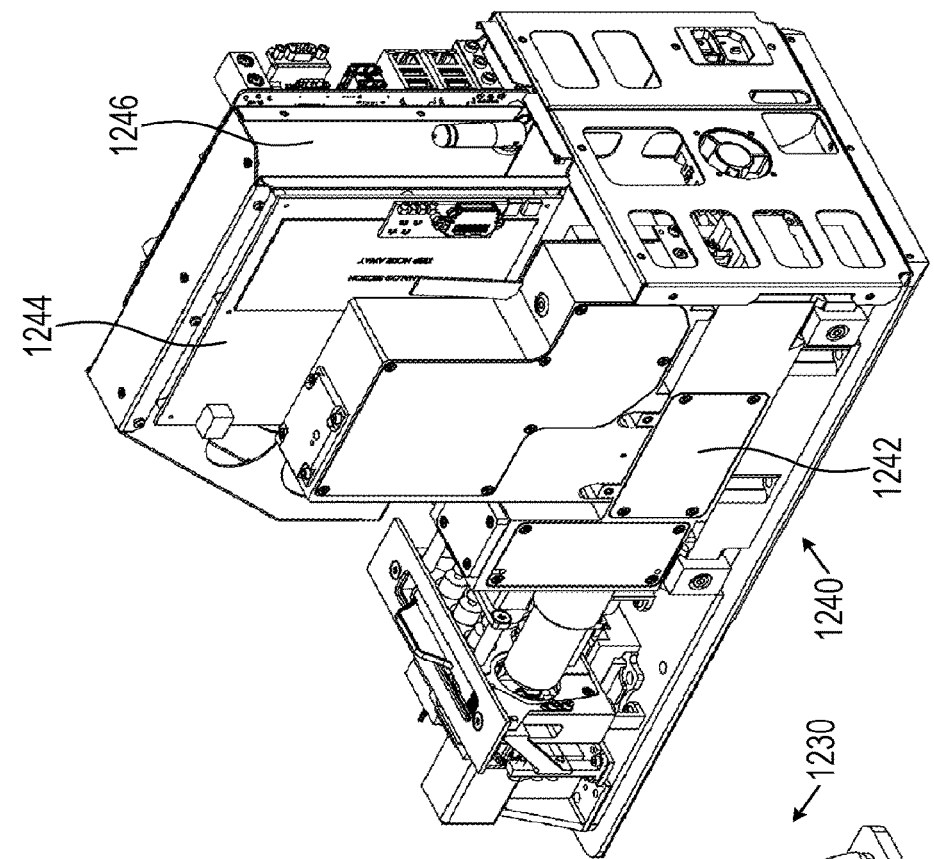
Figure 12B:
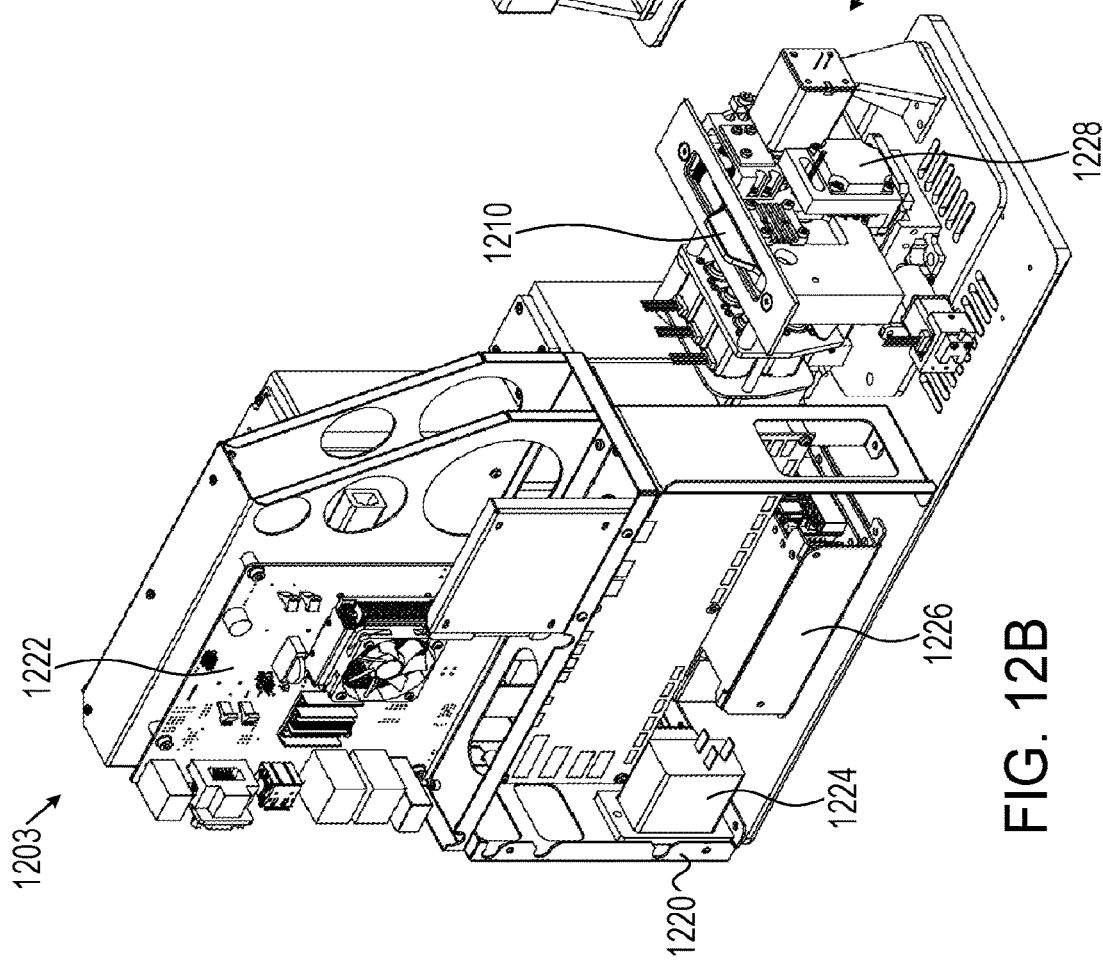
Figure 13A:
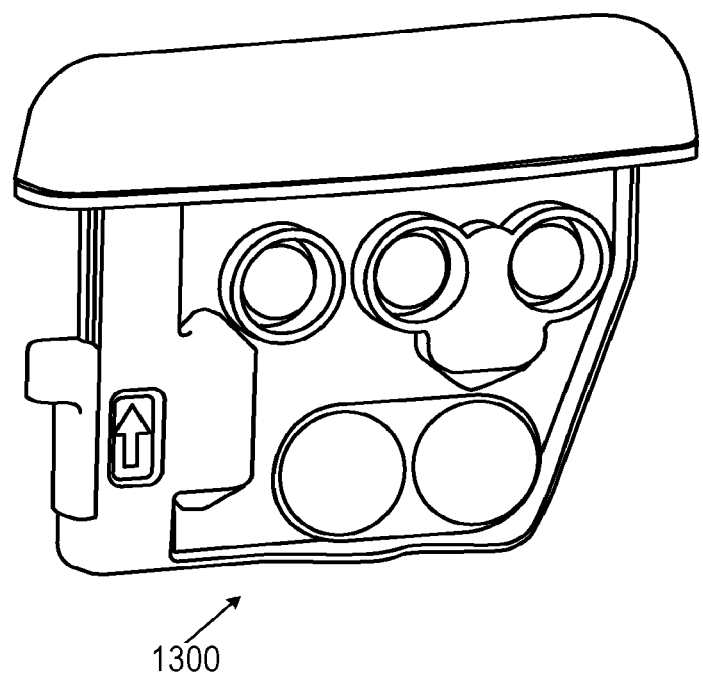
Figure 13B:
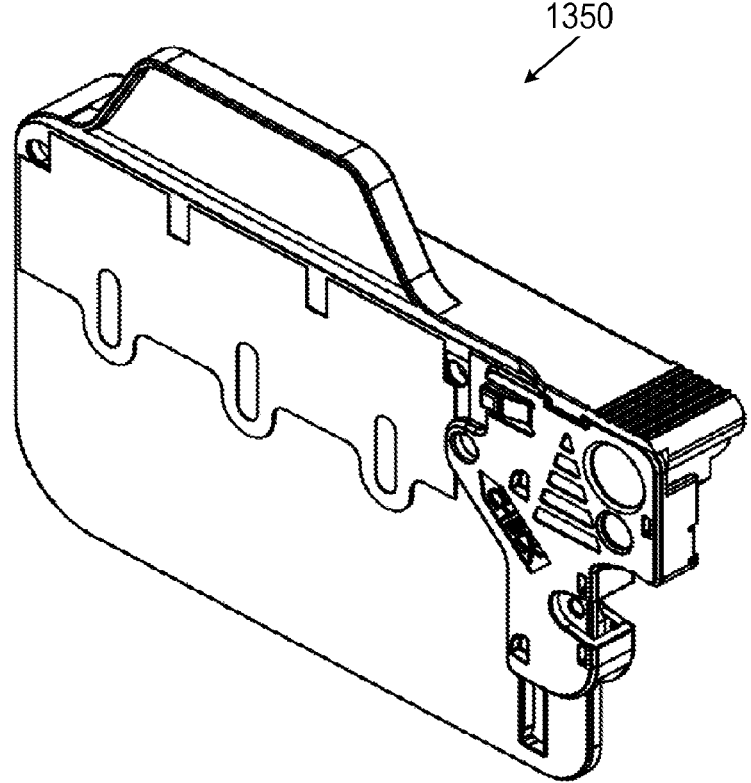
Figure 14A:
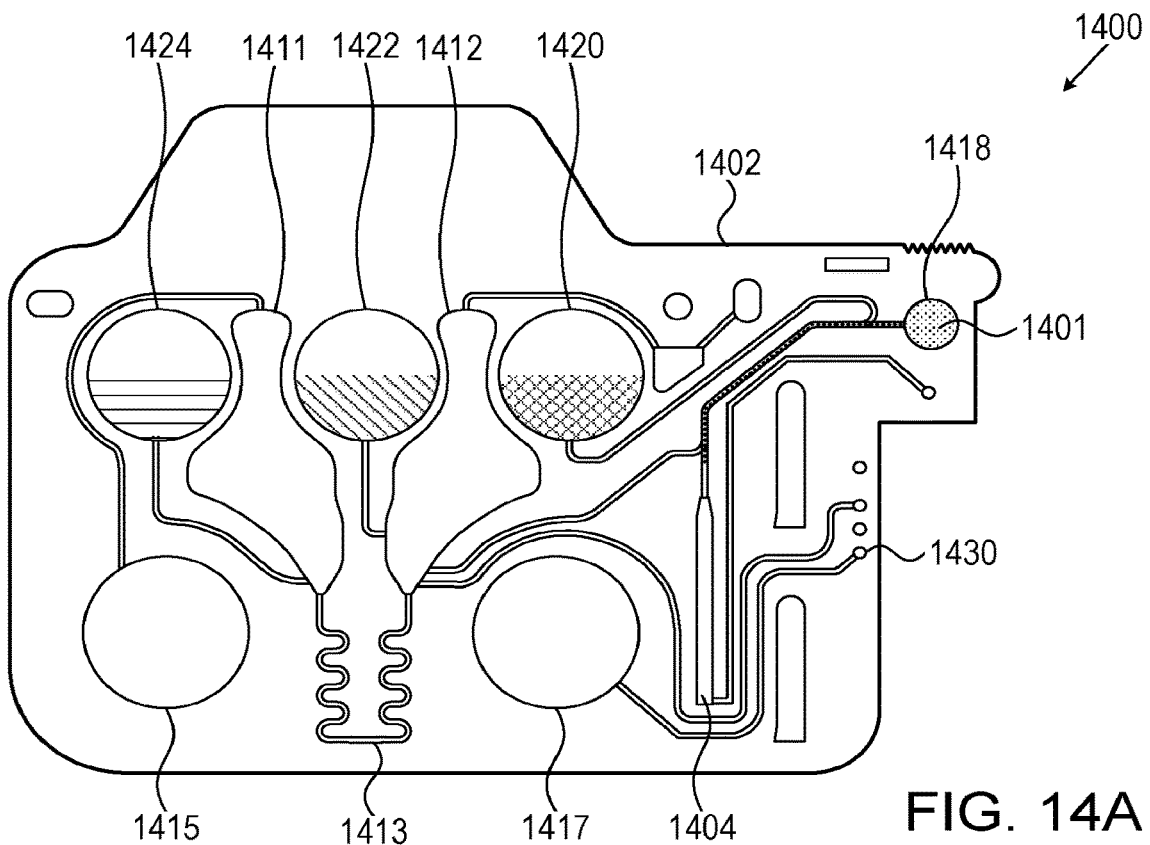
Figure 14B:
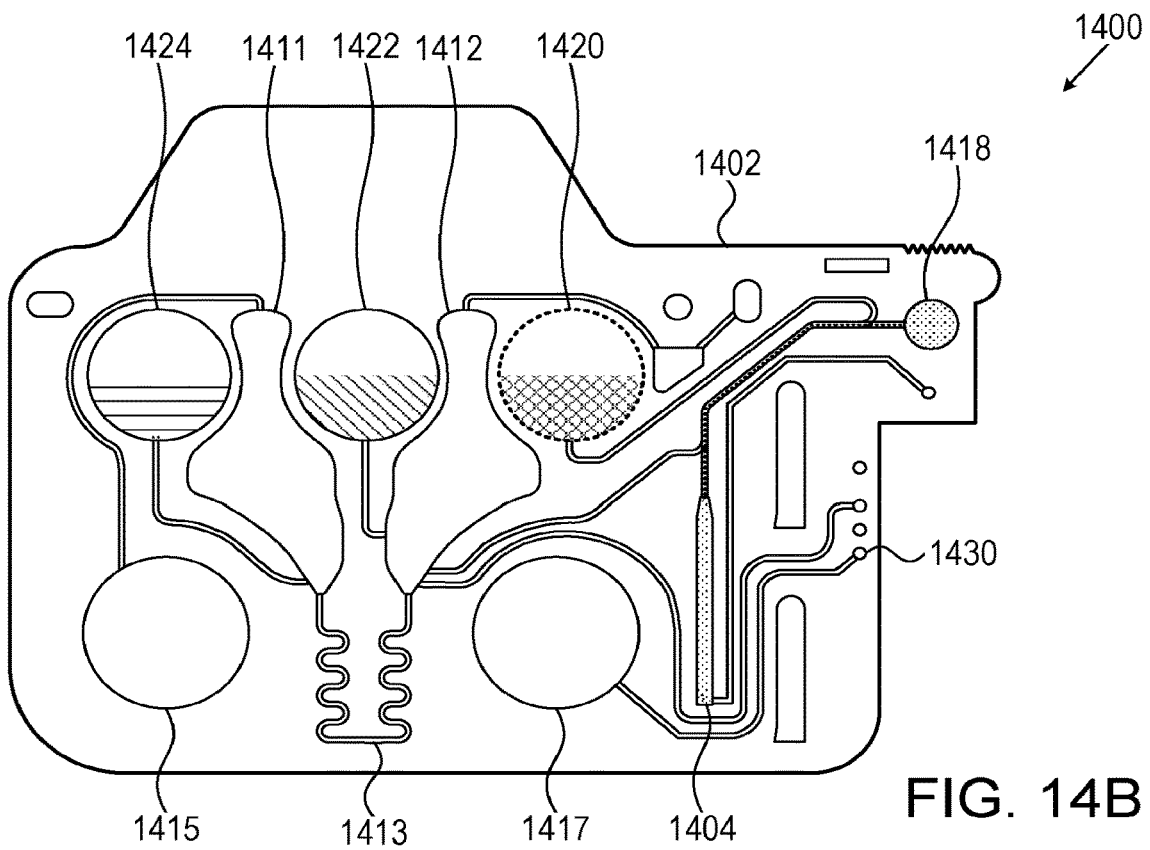
Figure 14C:
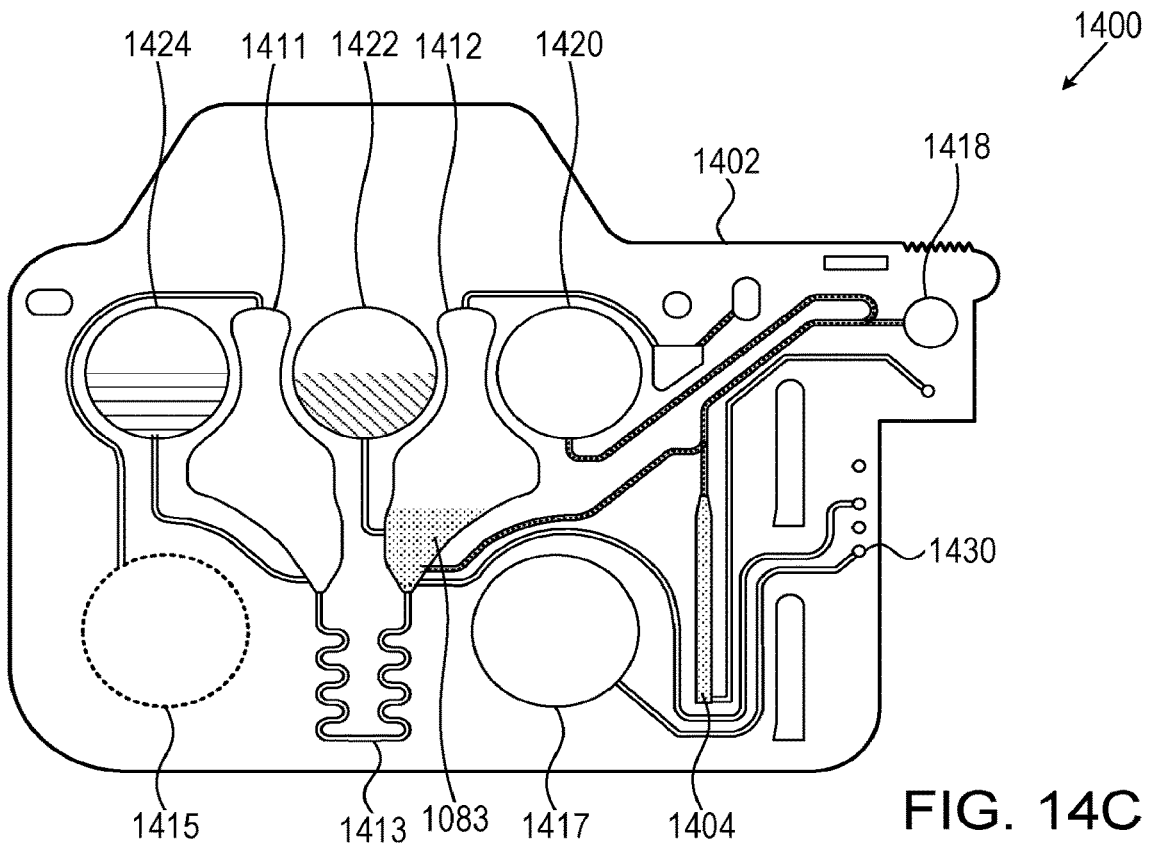
Figure 14D:
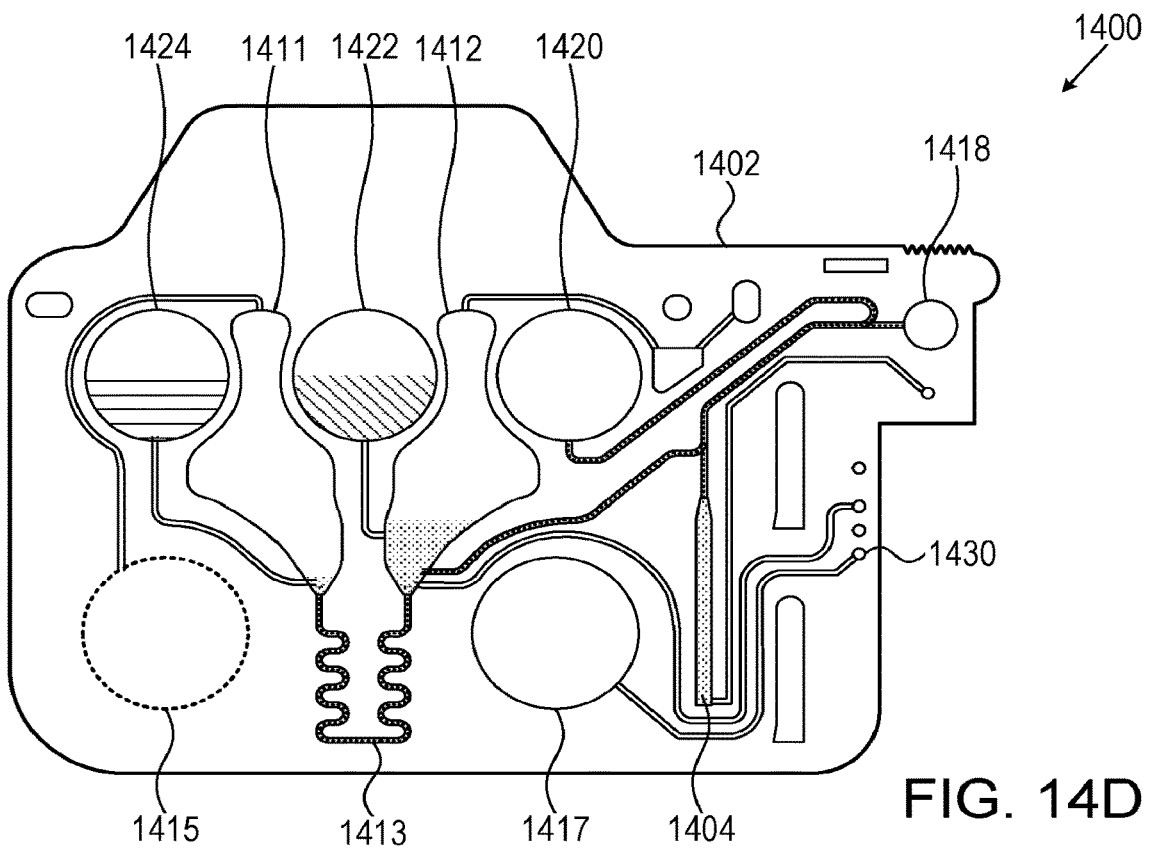
Figure 14E:
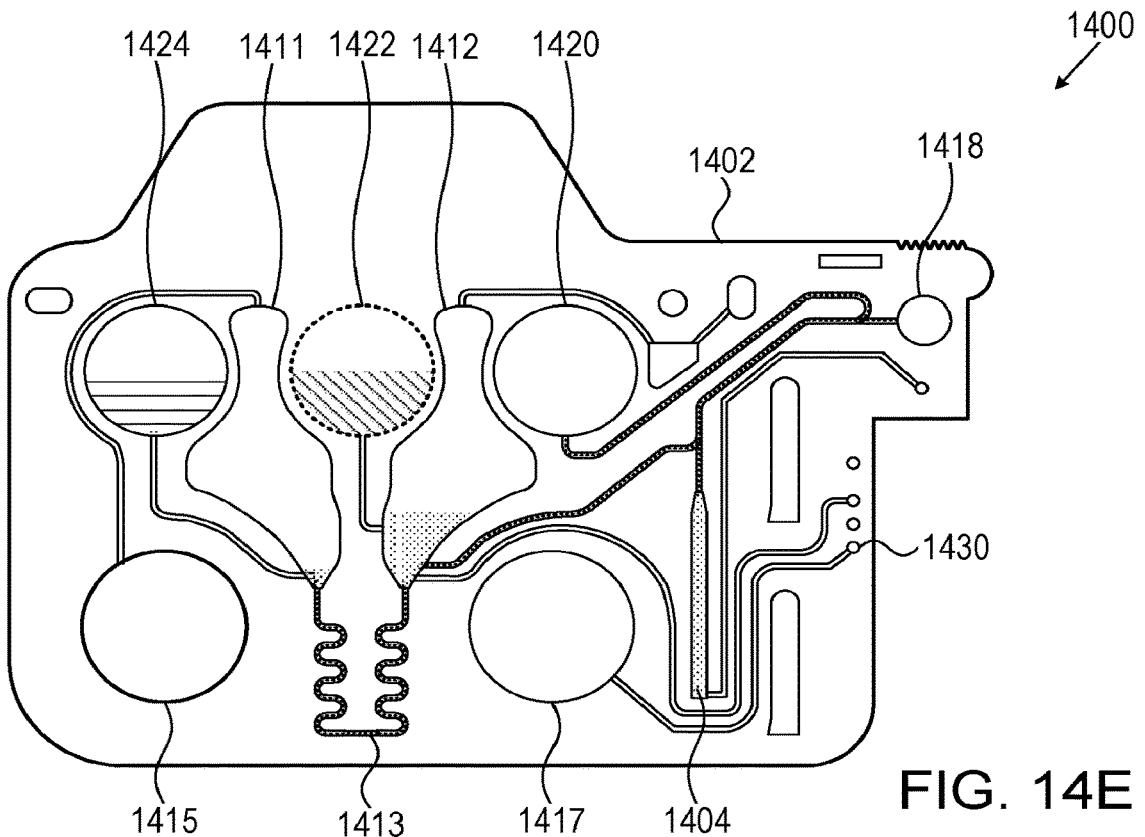
Figure 14F:
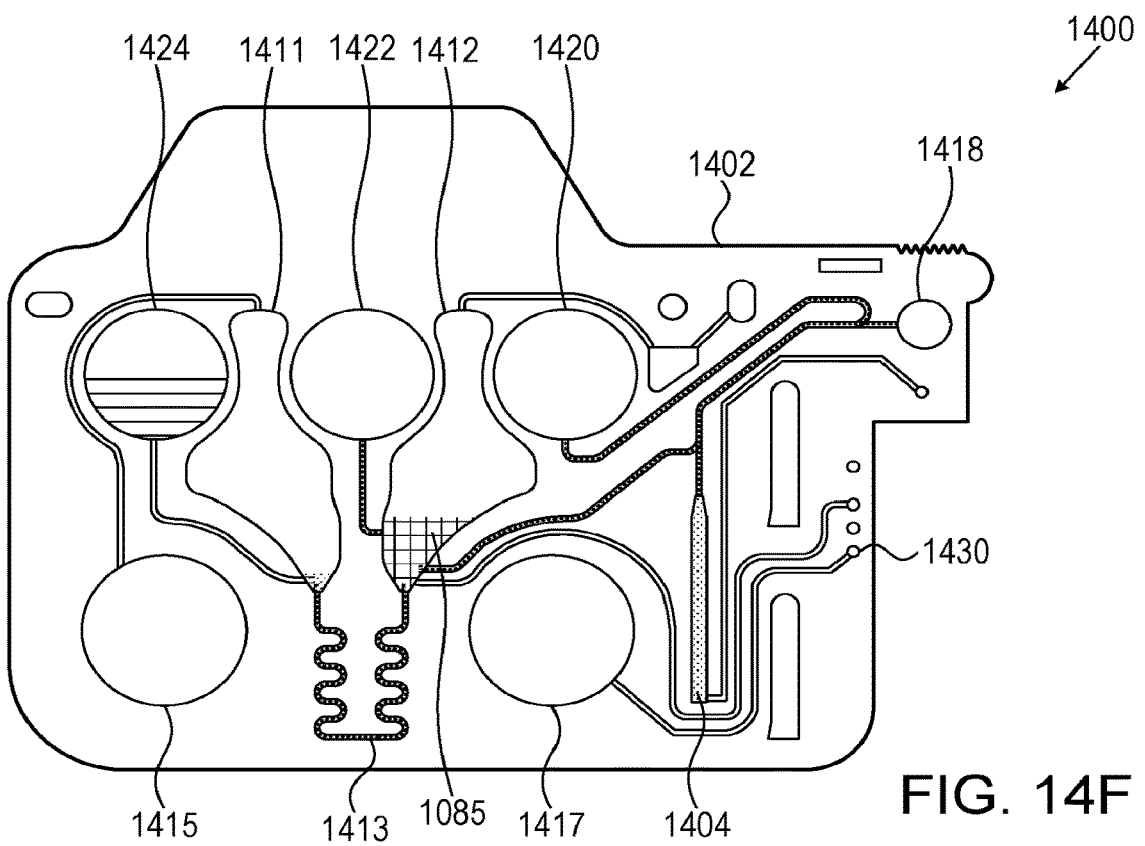
Figure 14G:
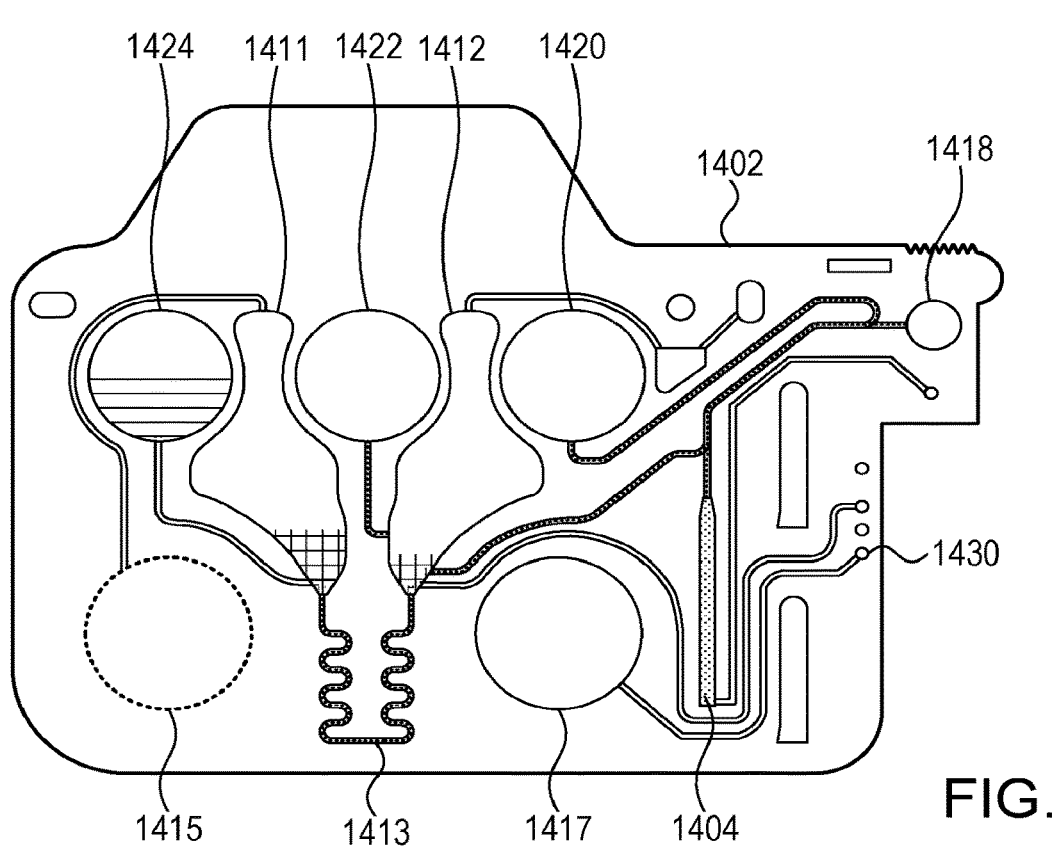
Figure 14H:
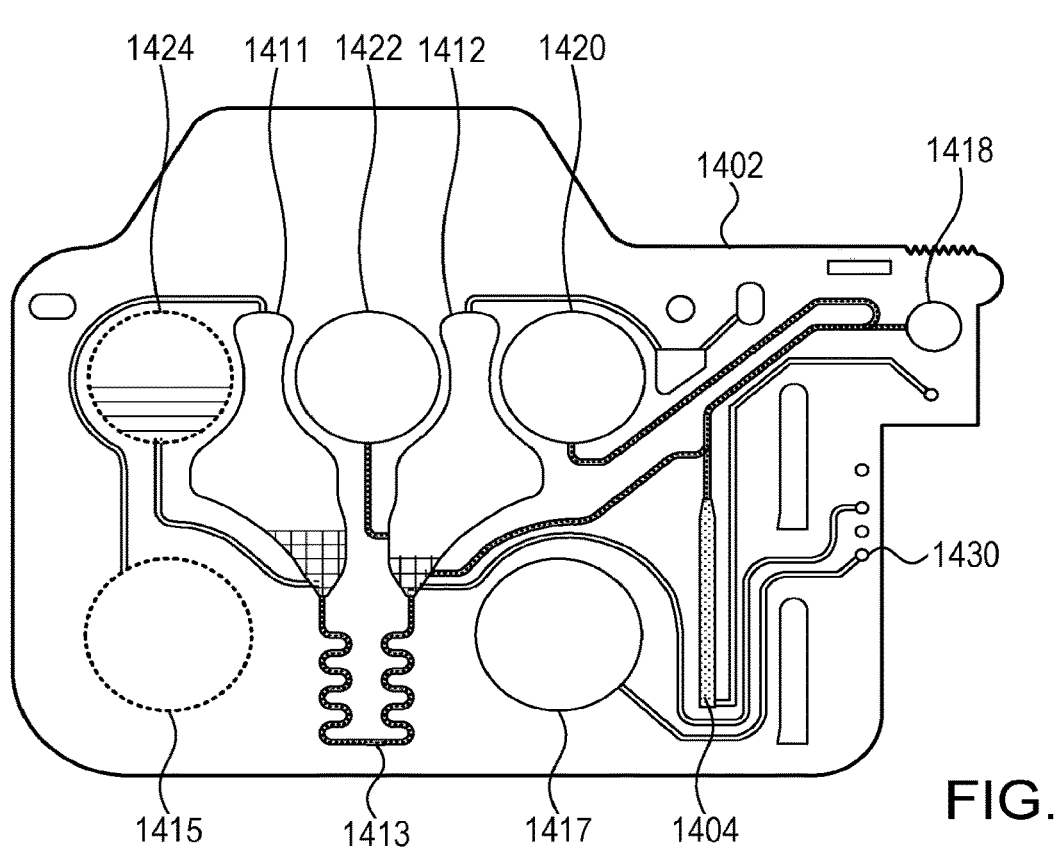
Figure 14I:
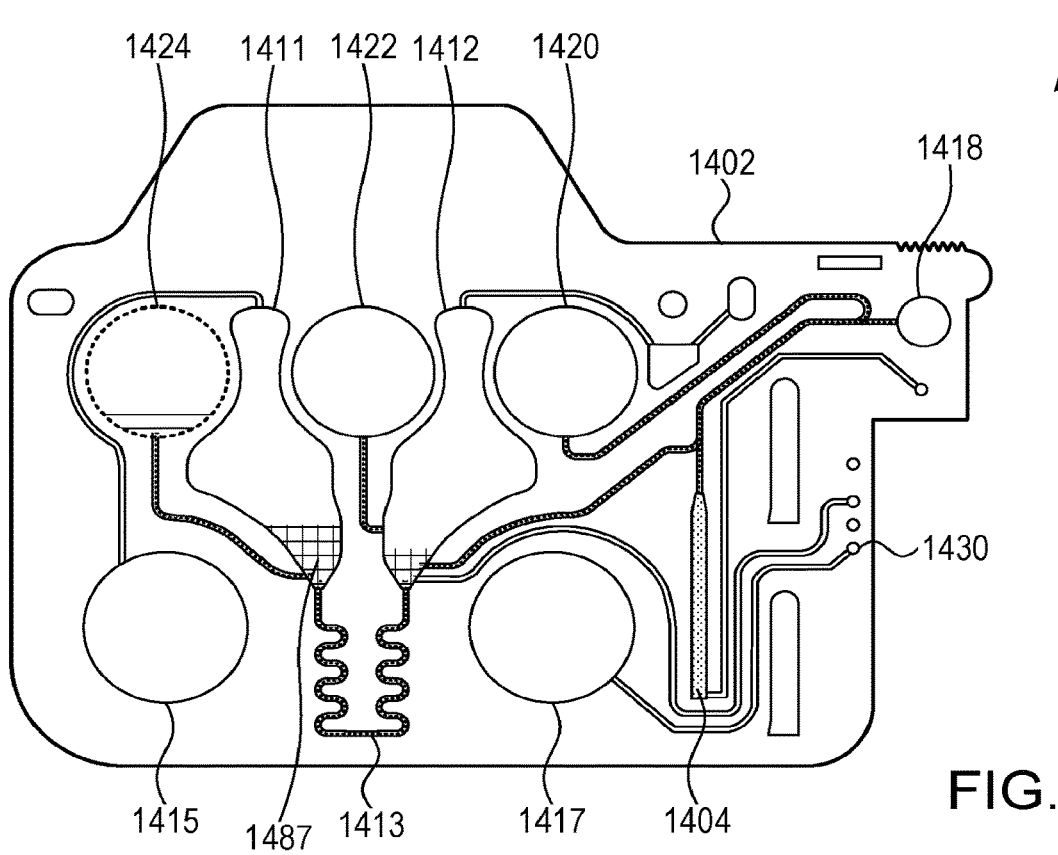
Figure 14J:
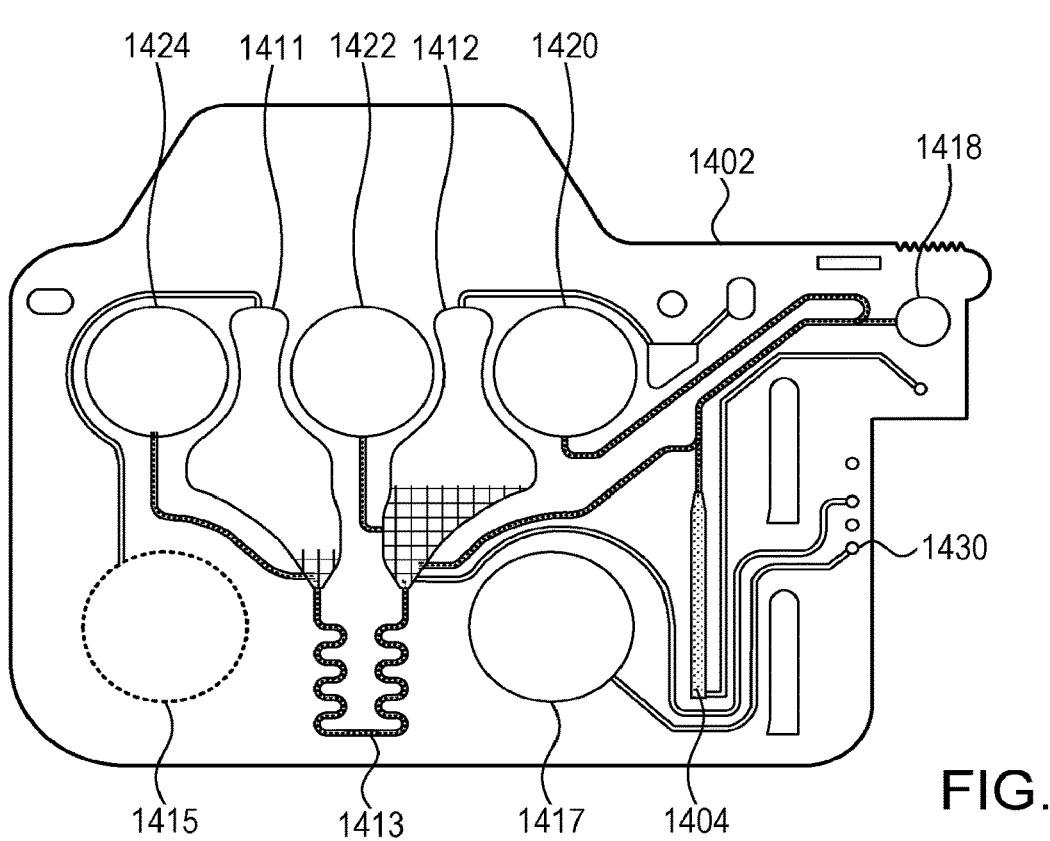
Figure 14K:
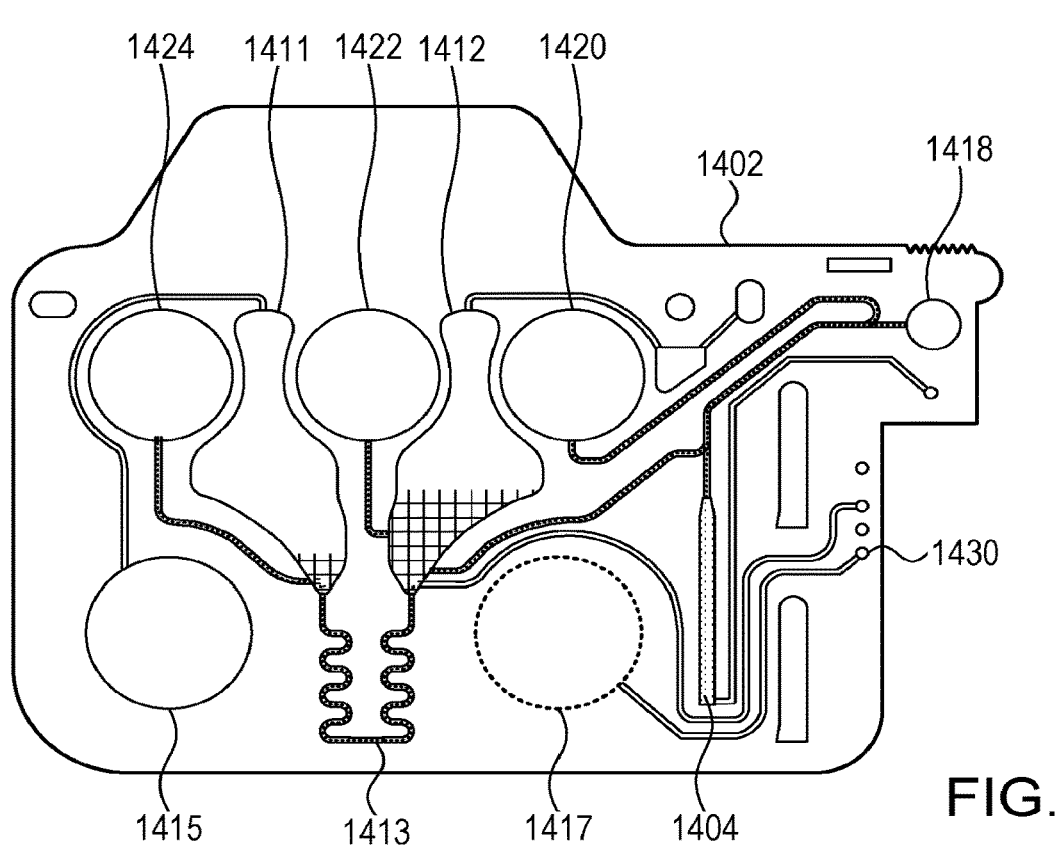
Figure 14L:
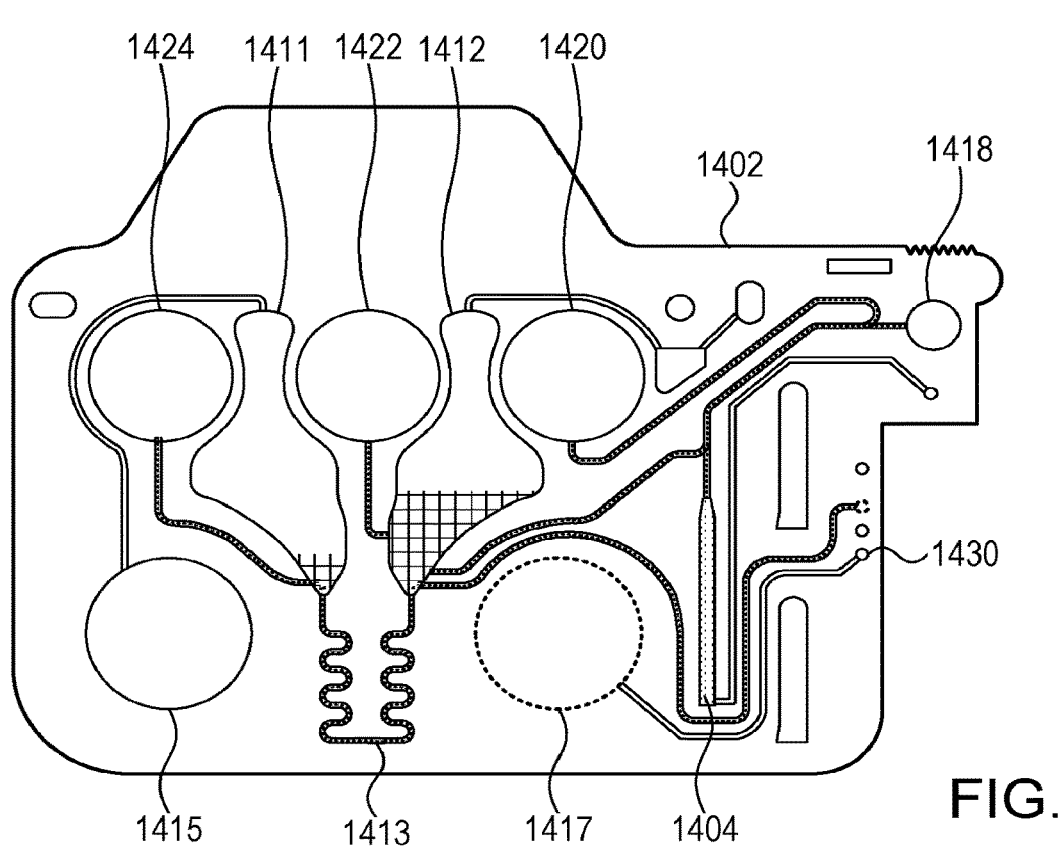
Figure 14M:
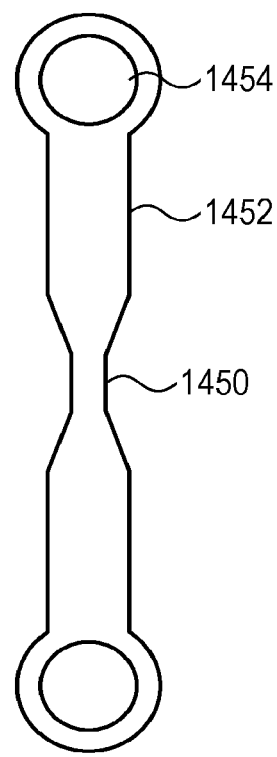
Figure 14N:
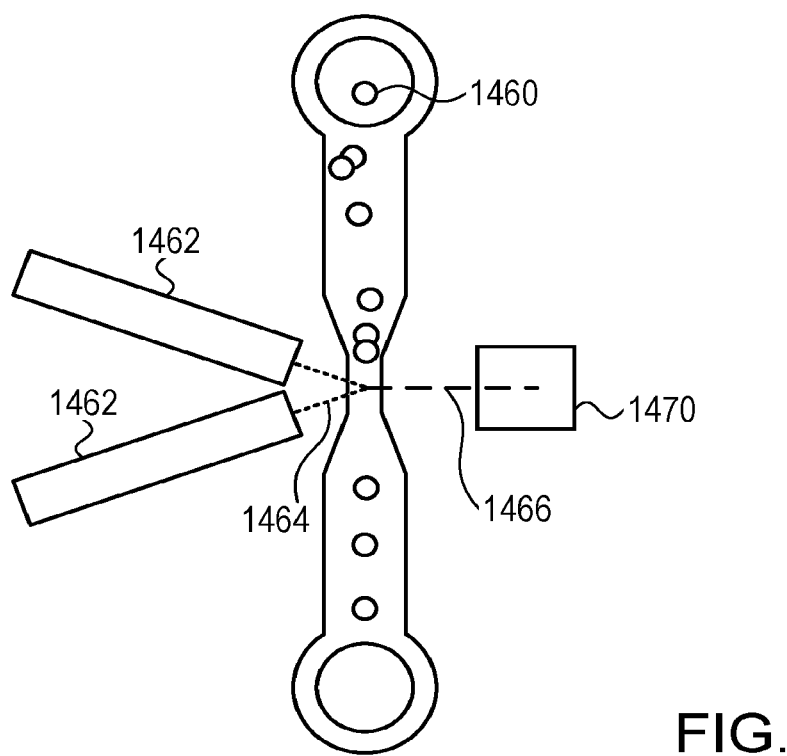
Figure 14O:
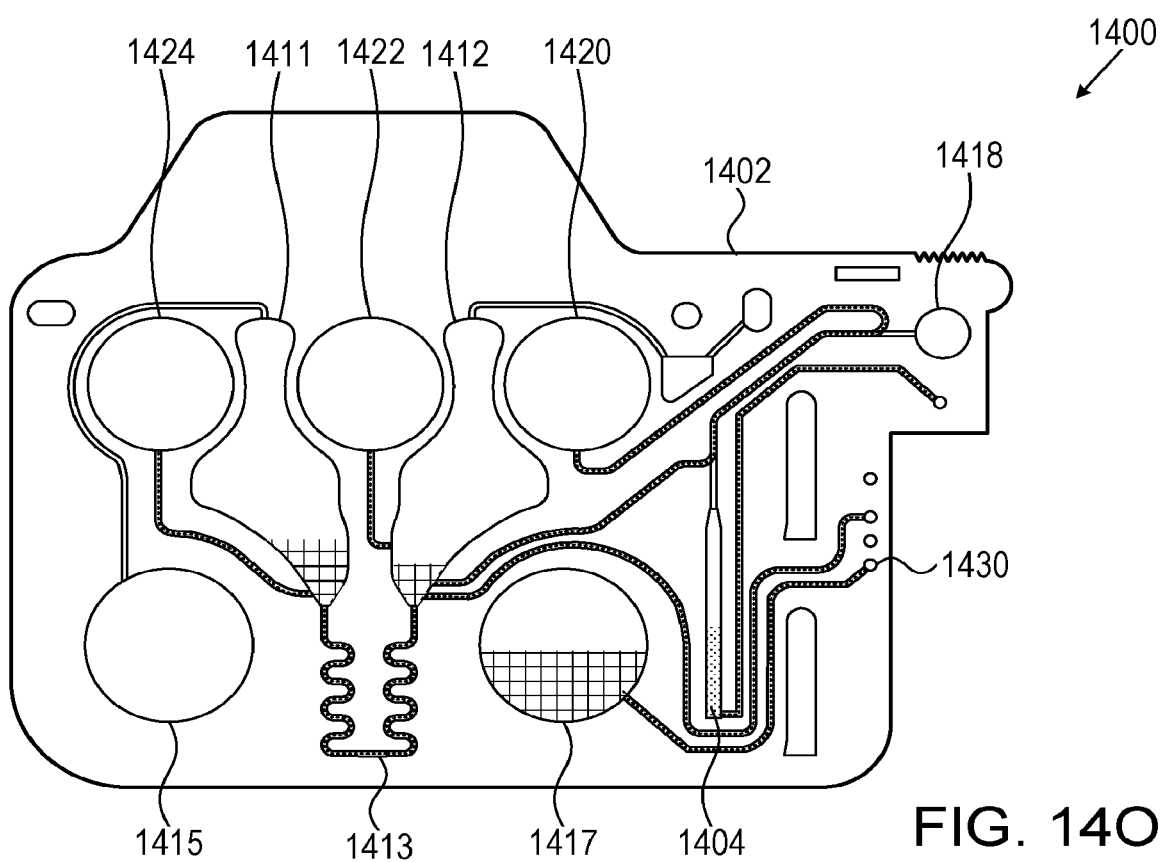
Figure 15:
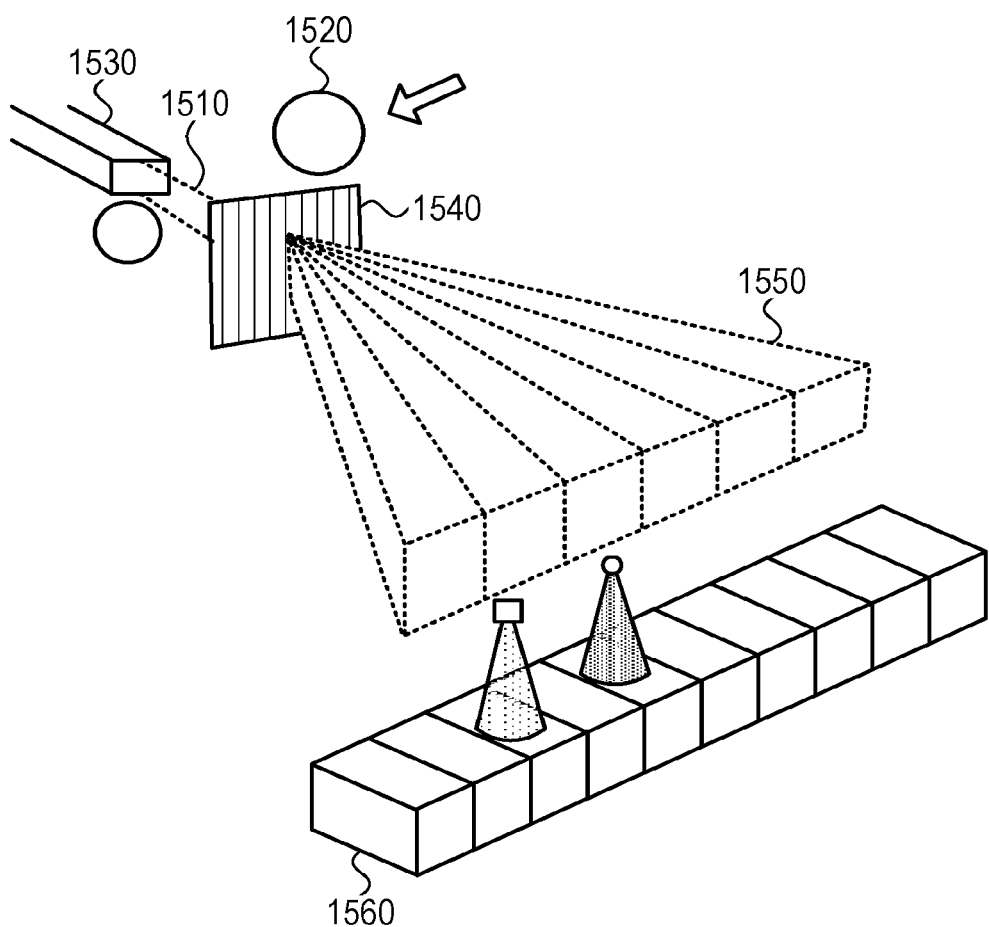
Figure 16:
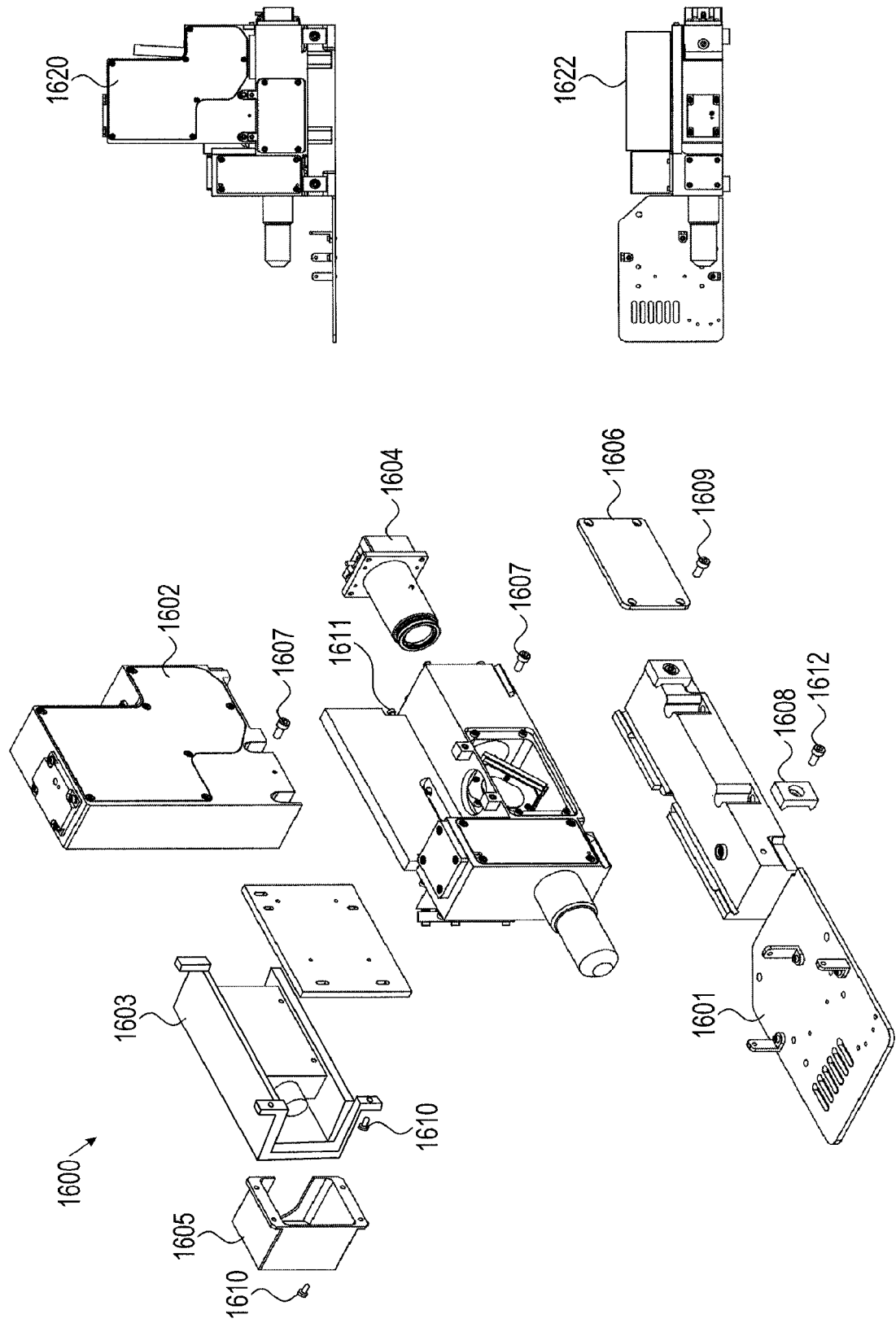
Figure 17:
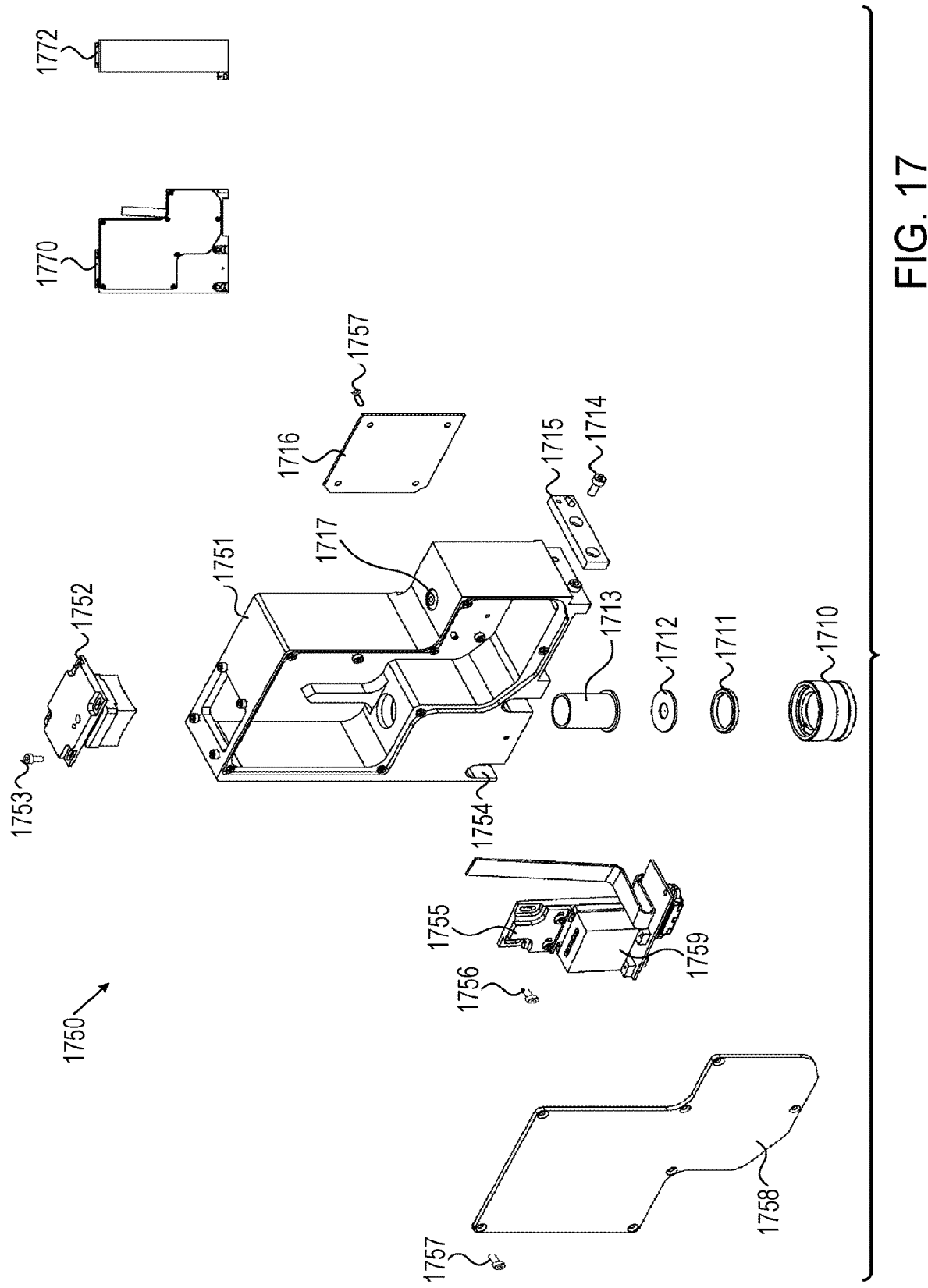
Figure 18A:
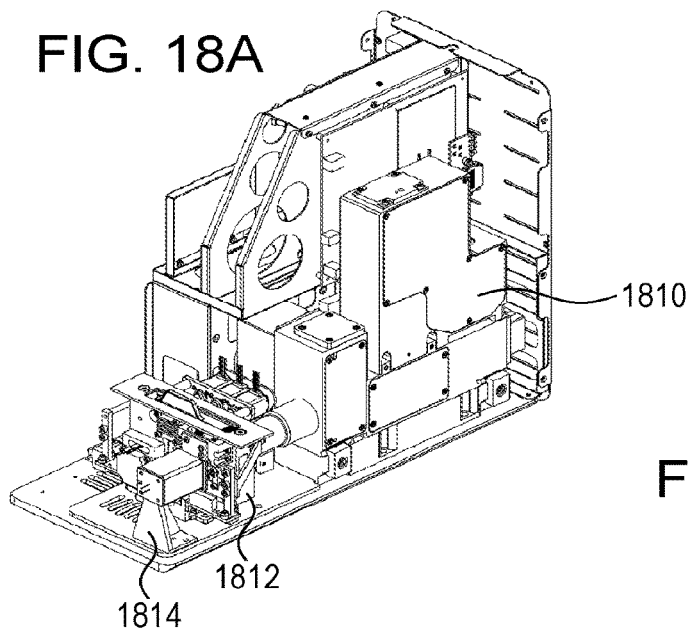
Figure 18B:
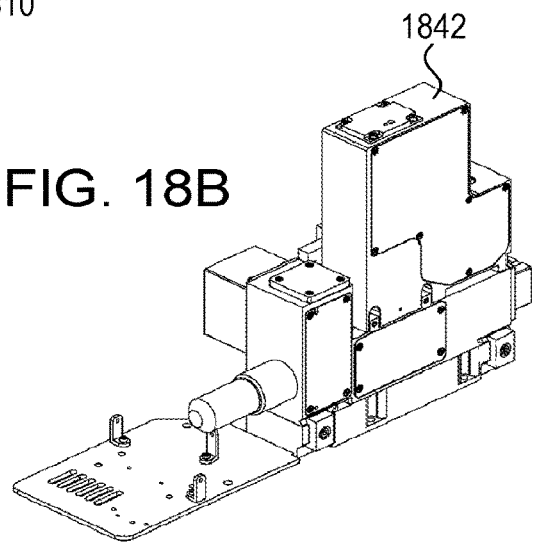
Figure 18C:
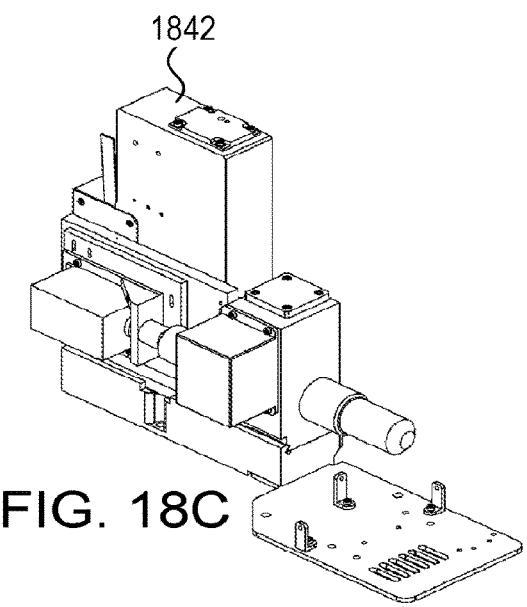
Figure 18D:
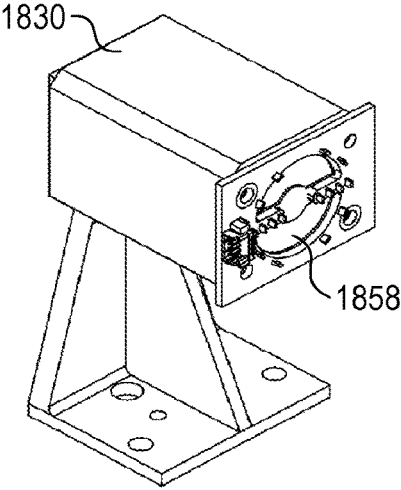
Figure 18E:
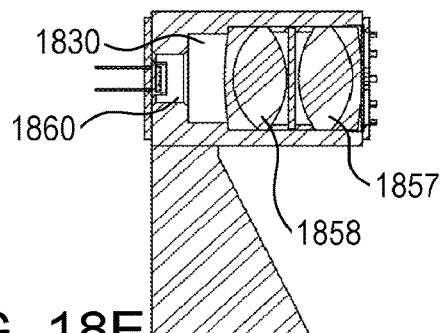
Figure 19A:
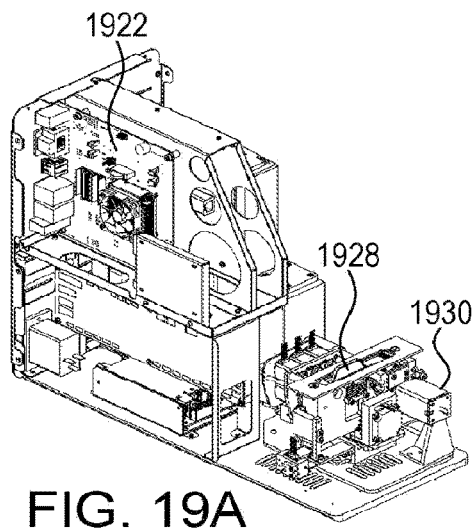
Figure 19B:
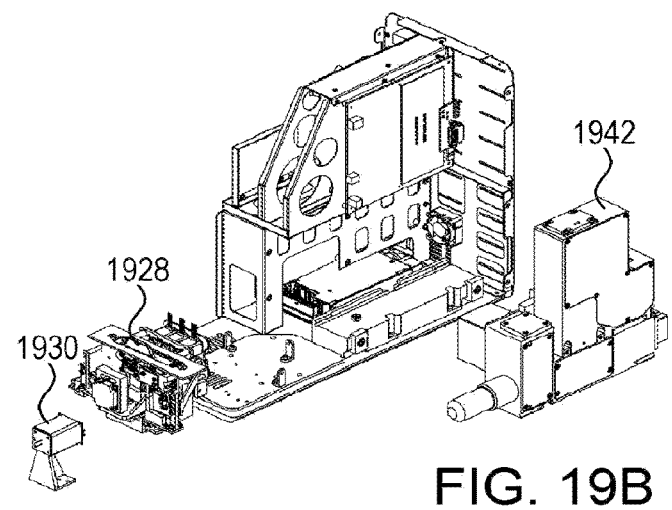
Figure 19C:
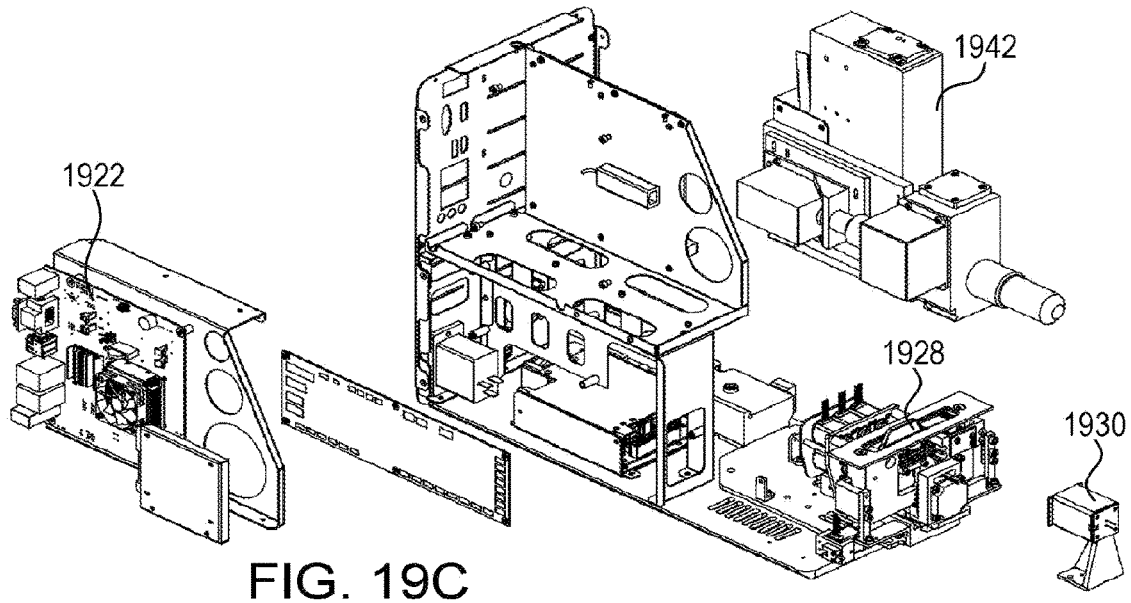
Figure 19D:
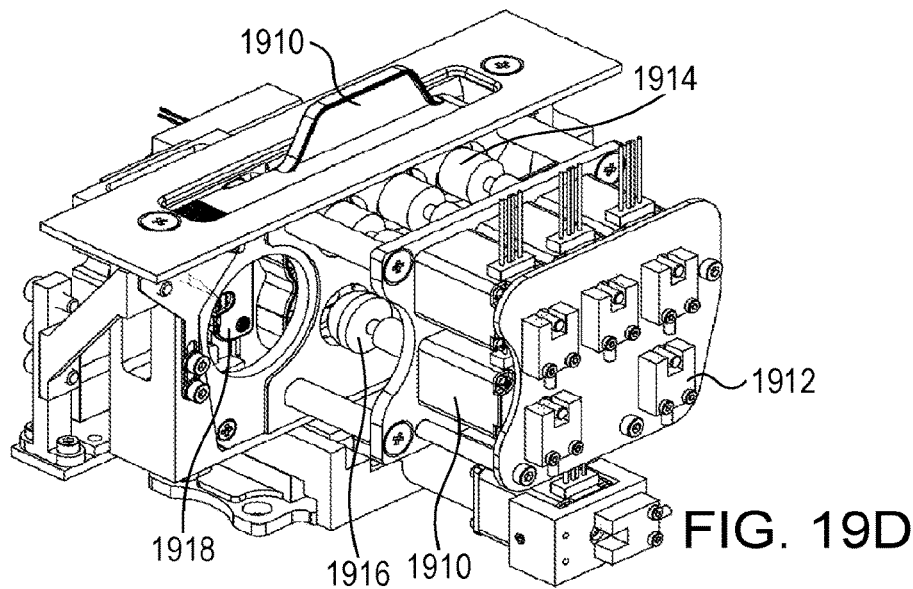
Figure 19E:
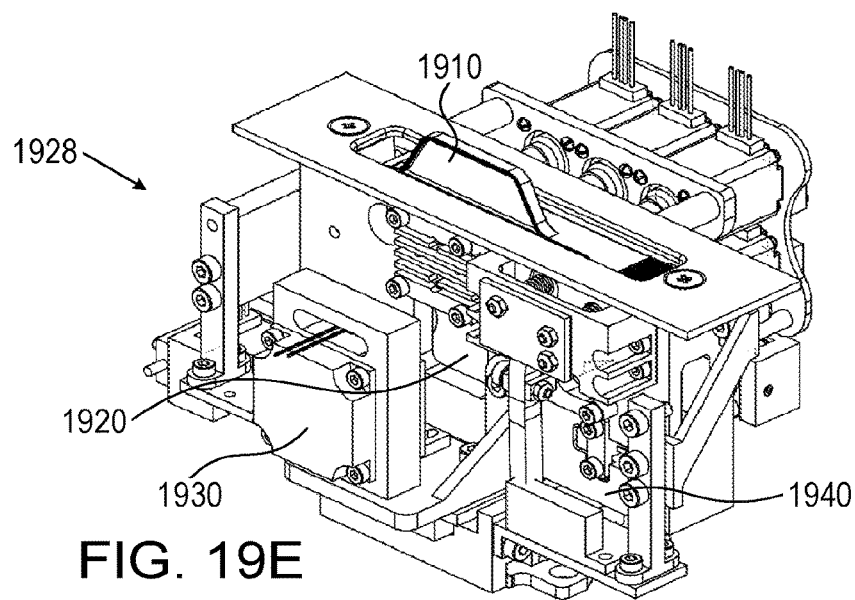
Figure 19F:
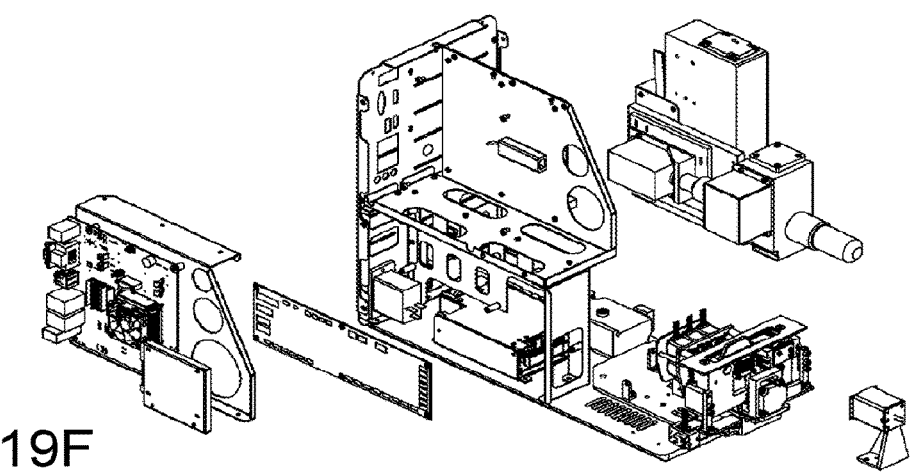
Figure 20:
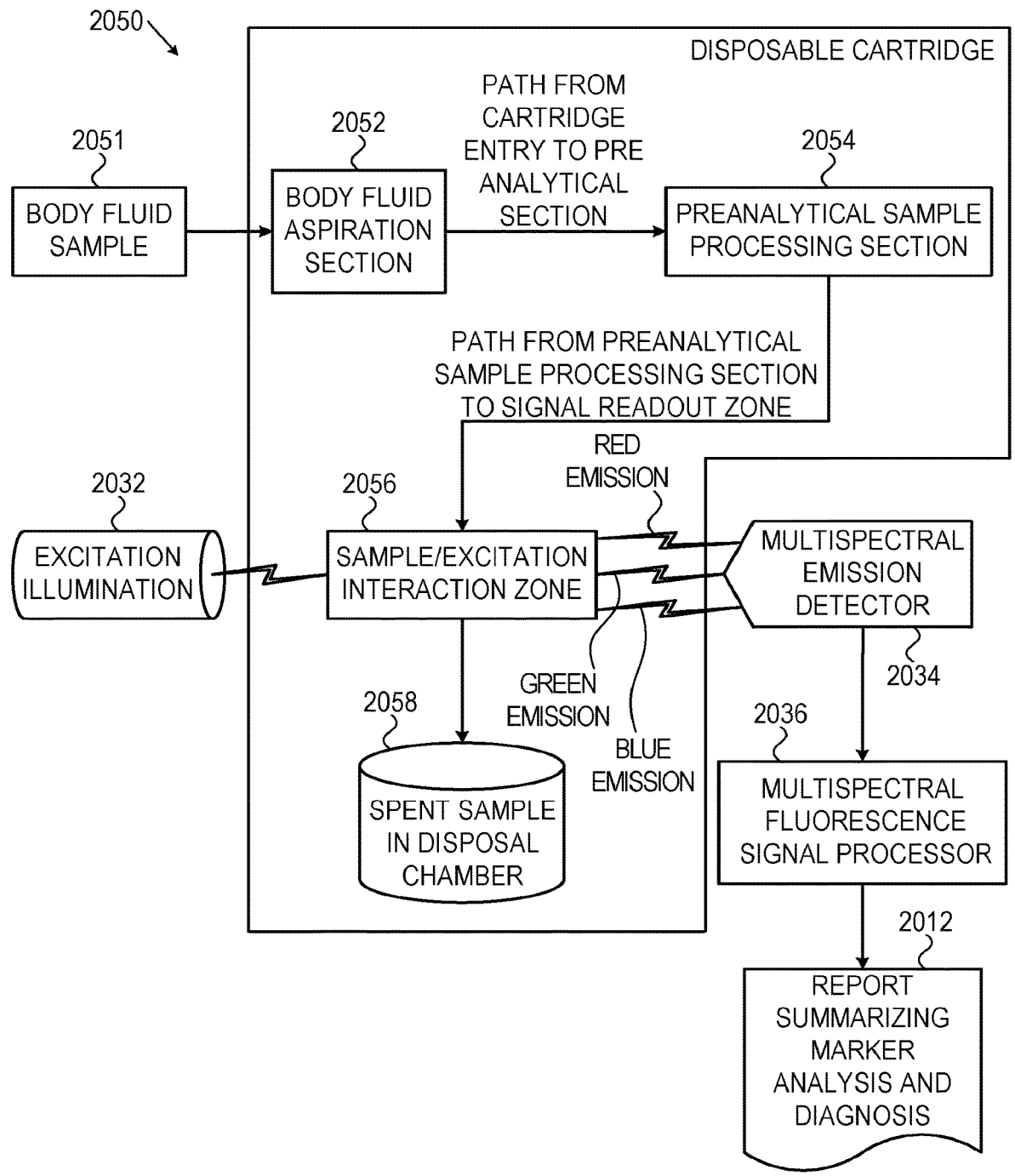
Figure 21A:
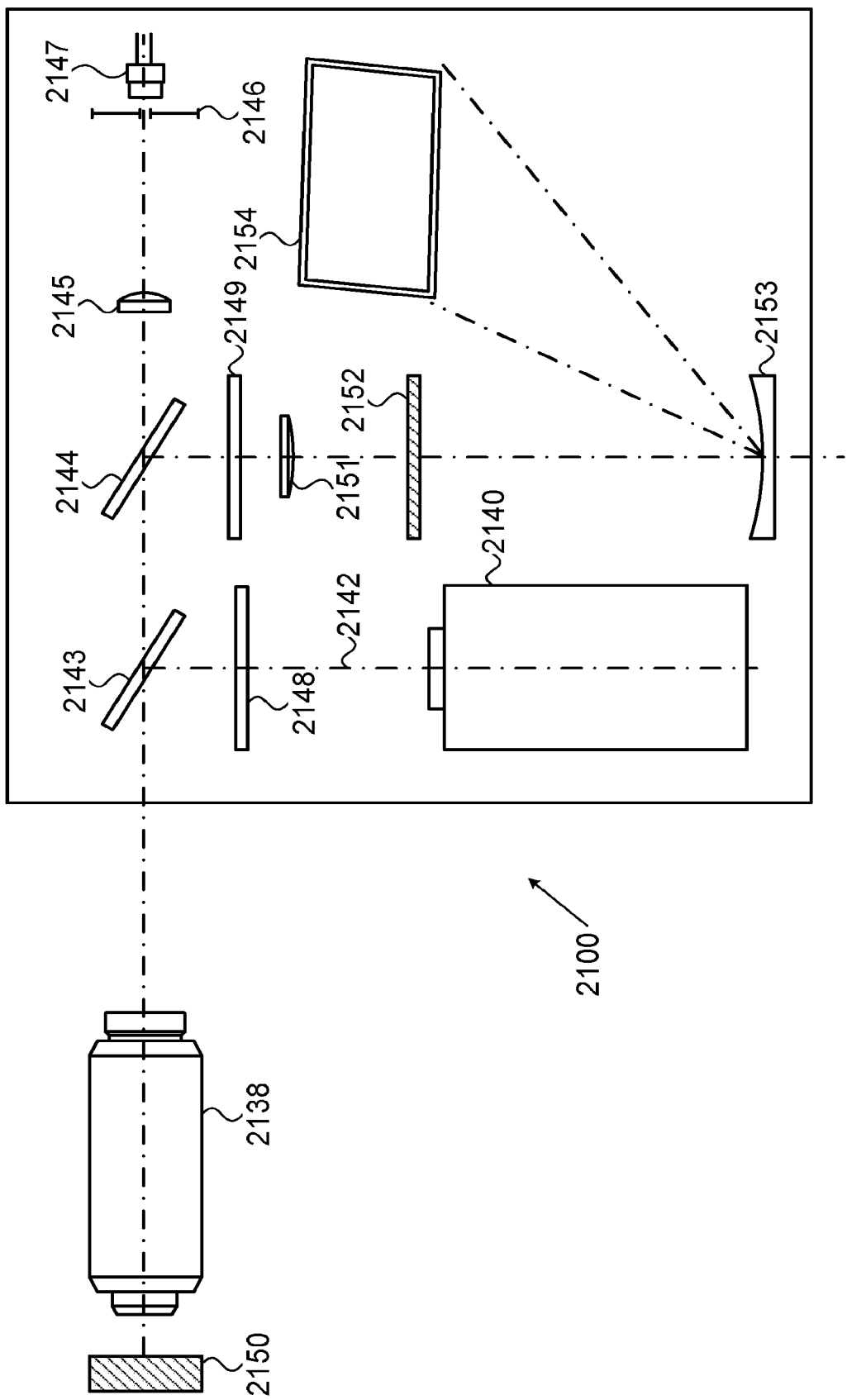
Figure 21B:
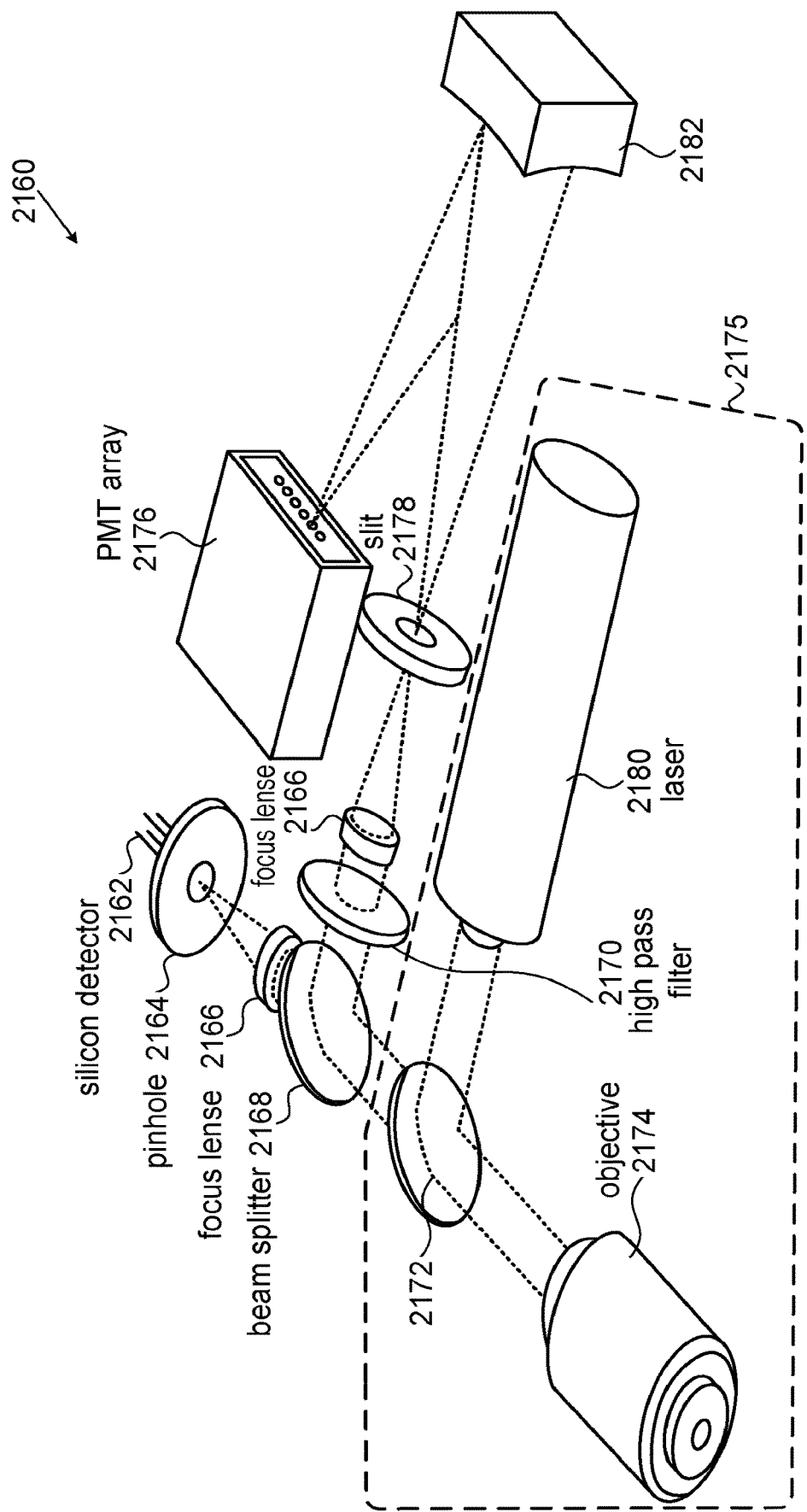
Figure 22A:
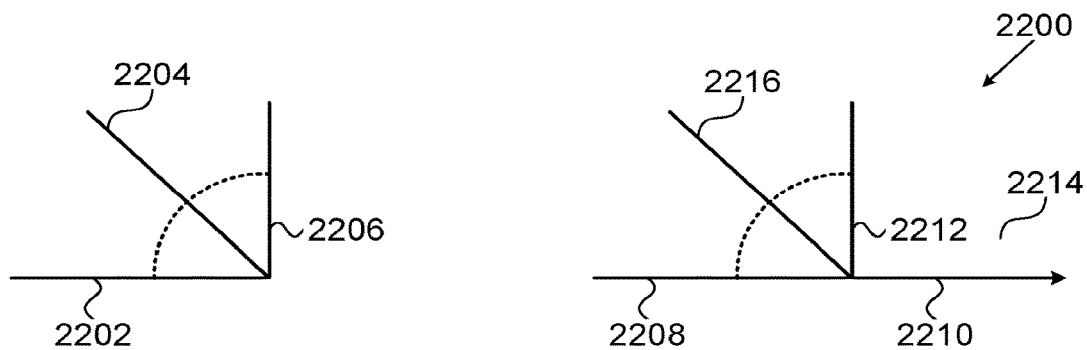
Figure 22B:
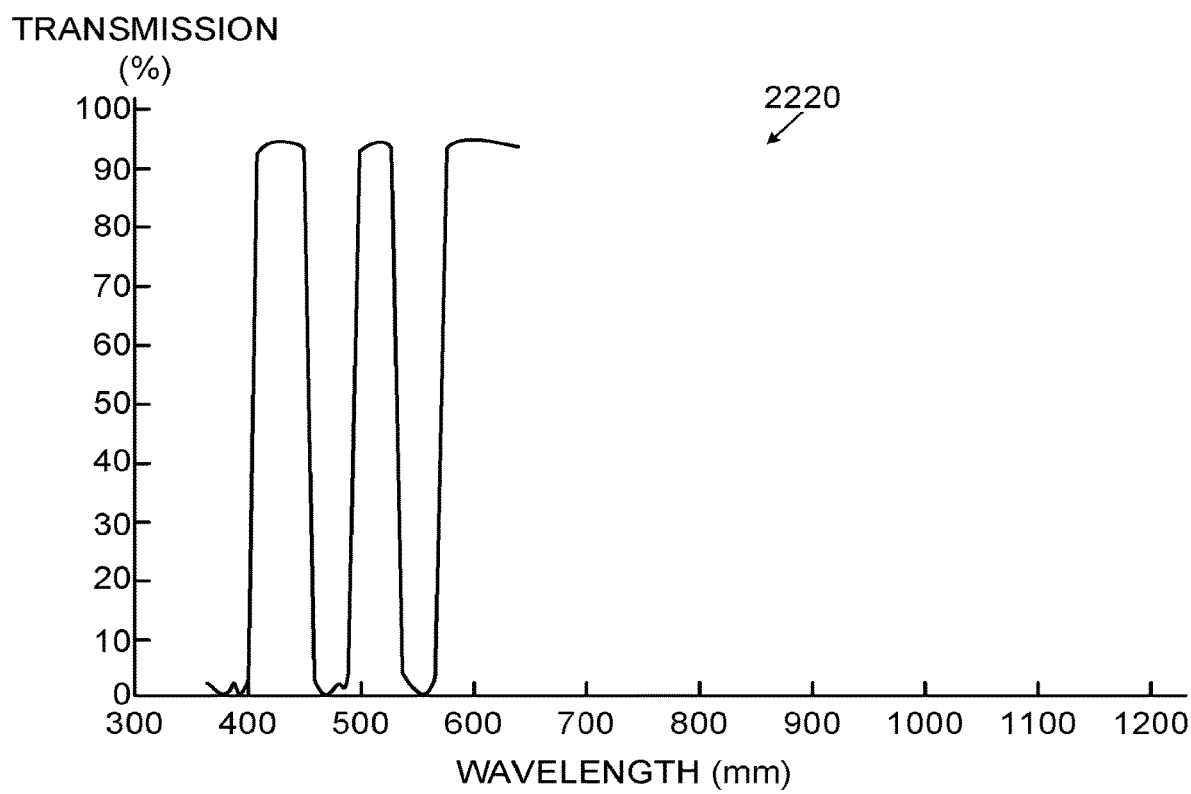
Figure 22C:
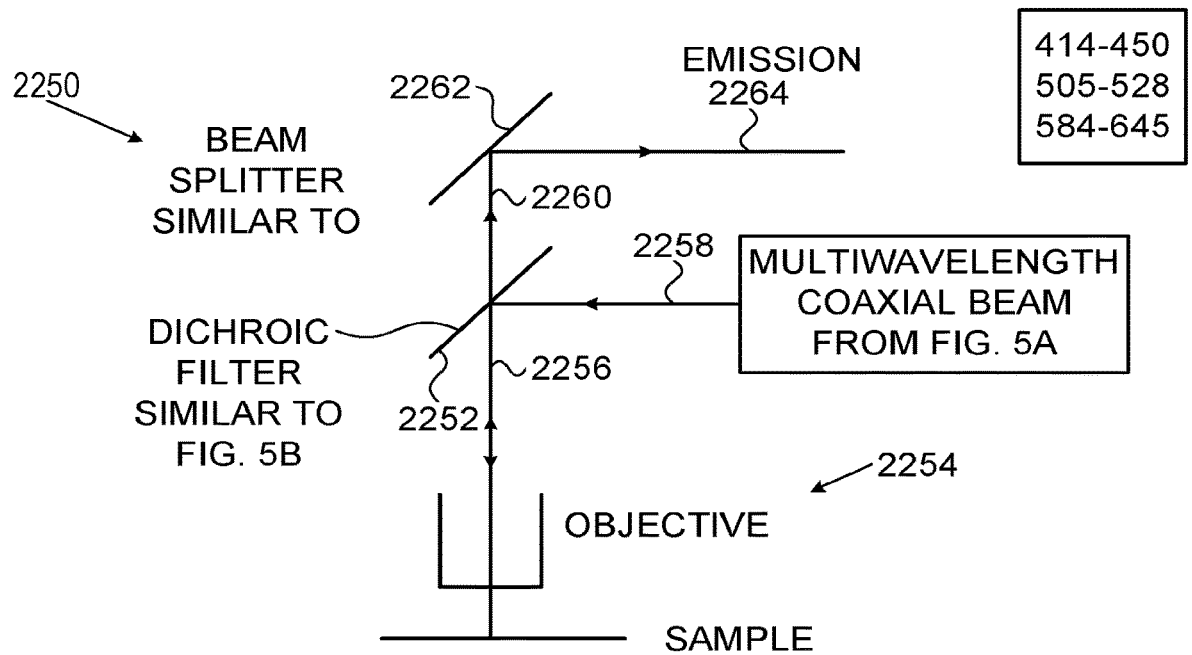

FIG. 8B is a graphical output of a fluorescent detection assay of an unbound tagged antibody signature, associated with the method of FIGS. 6-7, in accordance with an embodiment of the present invention;

FIG. 8C is a graphical output of a fluorescent detection assay of plasma protein target beads with target binding, associated with the method of FIGS. 6-7, in accordance with an embodiment of the present invention;

FIG. 8D is a graphical output of a fluorescent detection assay of a reference bead signature, associated with the method of FIGS. 6-7, in accordance with an embodiment of the present invention;

FIG. 9 is a simplified schematic illustration showing another microfluidics apparatus for detecting a chemical entity, in accordance with an embodiment of the present invention;

FIG. 10 is another simplified flow chart of a method for detecting a chemical entity, in accordance with an embodiment of the present invention;

FIG. 11 is a simplified schematic illustration showing a methodology for detecting and quantifying glucose, protein and albumin in a serum sample, in accordance with an embodiment of the present invention;

FIG. 12A is a simplified three dimensional front view of a reader assembly and cartridge for detecting a biological condition, in accordance with an embodiment of the present invention;

FIG. 12B is a simplified three dimensional inner front view of a reader assembly for detecting a biological condition, in accordance with an embodiment of the present invention;

FIG. 12C is a simplified three dimensional inner rear view of a reader assembly for detecting a biological condition, in accordance with an embodiment of the present invention;

FIG. 13A is an outer side view of a cartridge assembly, in accordance with an embodiment of the present invention;

FIG. 13B is an inner side view of a cartridge assembly, in accordance with an embodiment of the present invention;

FIGS. 14A-14O show a sequence of process events in a cartridge assembly, in accordance with an embodiment of the present invention;

FIG. 15 is a schematic illustration of a micro flow spectrometer reading, in accordance with an embodiment of the present invention;

FIG. 16 is a simplified blown up diagram of an optical reader assembly for detecting a biological condition, in accordance with an embodiment of the present invention;

FIG. 17 is another simplified blown up diagram of a photomultiplier tube of the optical reader assembly for detecting a biological condition, in accordance with an embodiment of the present invention;

FIG. 18A shows a reader optics assembly, a cartridge handling unit, and a forward scatter detection unit, in accordance with an embodiment of the present invention;

FIG. 18B shows a right side view of a reader optics assembly, in accordance with an embodiment of the present invention;

FIG. 18C shows a left side view of a reader optics assembly, in accordance with an embodiment of the present invention;

FIG. 18D is a forward scatter detection assembly, in accordance with an embodiment of the present invention;

FIG. 18E is a side view of the forward scatter detection assembly, in accordance with an embodiment of the present invention;

FIG. 19A shows a cutaway view of a reader assembly, in accordance with an embodiment of the present invention;

FIG. 19B shows an exploded right side view of a reader assembly, in accordance with an embodiment of the present invention;

FIG. 19C shows a left side blown up view of the reader assembly, in accordance with an embodiment of the present invention;

FIG. 19D shows a rear view of a cartridge handling unit (CHU), in accordance with an embodiment of the present invention;

FIG. 19E shows a front view of a cartridge handling unit (CHU), in accordance with an embodiment of the present invention;

FIG. 19F is a simplified illustration of a disposable cartridge of the system of FIG. 12A, in accordance with an embodiment of the present invention;

FIG. 20 is a simplified illustration of a disposable cartridge for rapid determination of a medical condition, in accordance with an embodiment of the present invention;

FIG. 21A is a simplified schematic illustration of an optical arrangement of a reader optics assembly, in accordance with an embodiment of the present invention;

FIG. 21B is another simplified schematic illustration of optical arrangement of a reader optics assembly, in accordance with an embodiment of the present invention;

FIG. 22A is a schematic representation of one example of multi-wavelength excitation in the optical unit of FIG. 21A or 21B, in accordance with an embodiment of the present invention;

FIG. 22B shows a graphical output of transmission as a function of wavelength for a dichroic filter of FIG. 21B, employing the multi-wavelength excitation of FIG. 22A, in accordance with an embodiment of the present invention;

FIG. 22C is a schematic representation of part of the optical unit employing multi-wavelength excitation of FIG. 22A and the dichroic filter of FIG. 21A, in accordance with an embodiment of the present invention.

Figure 1:
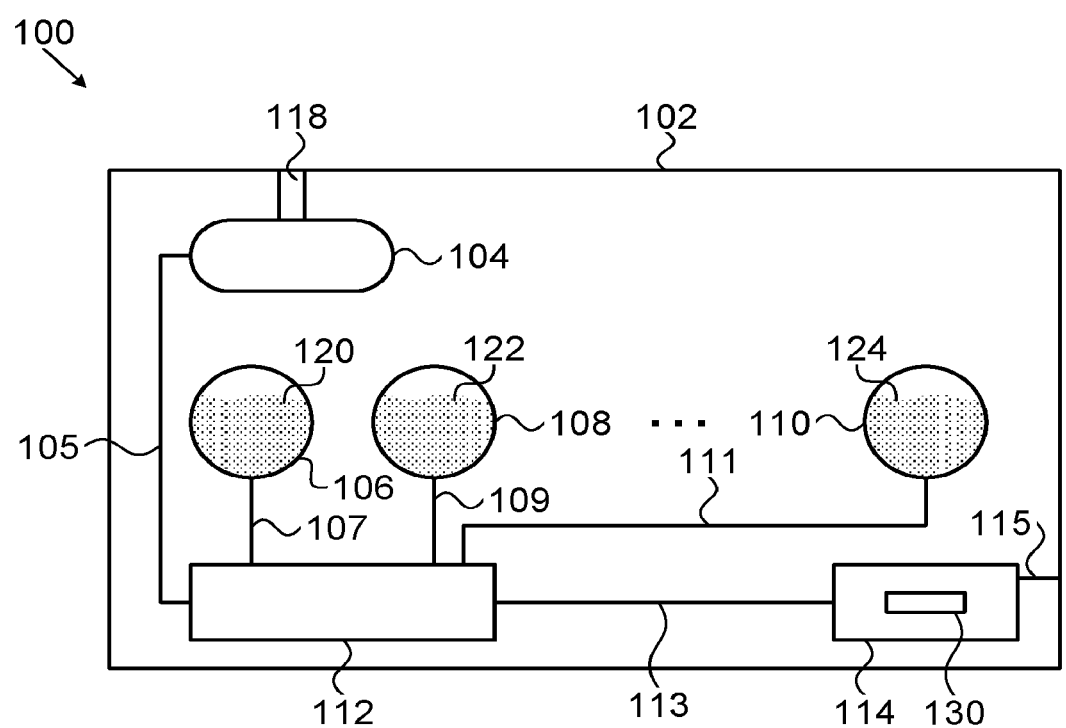
Figure 23A:
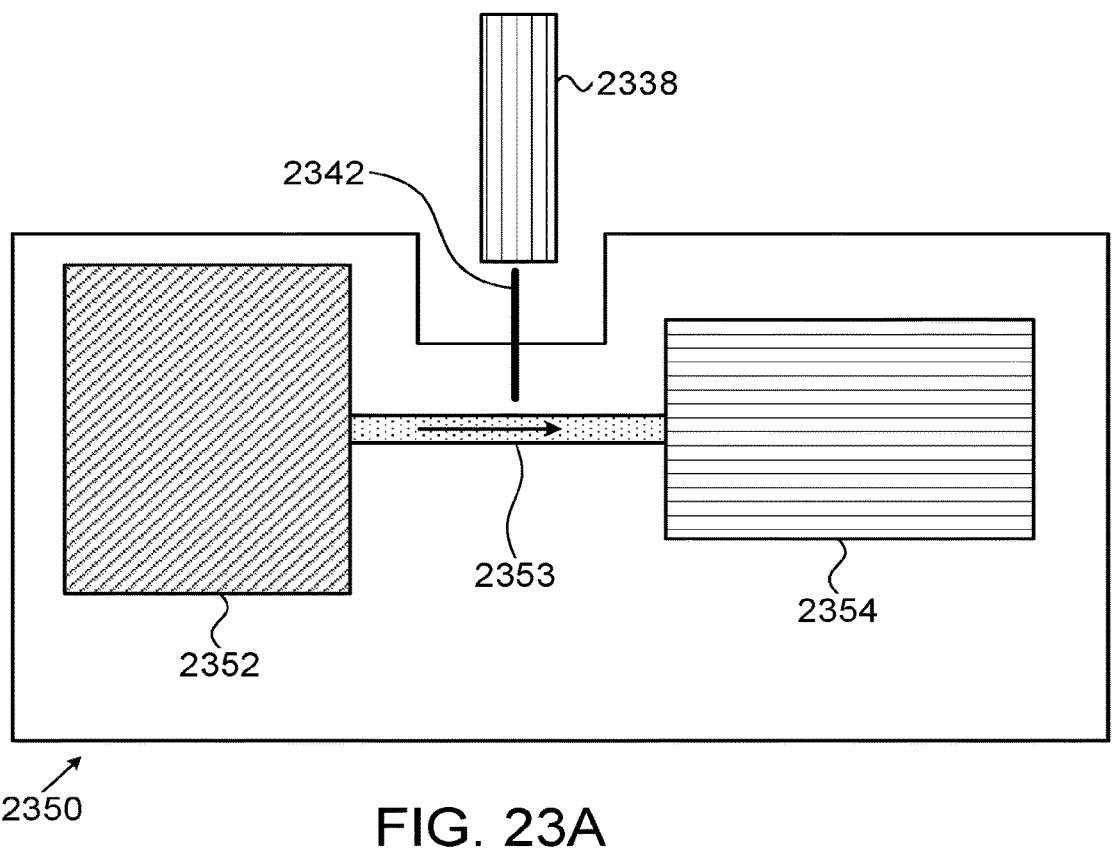
Figure 23B:
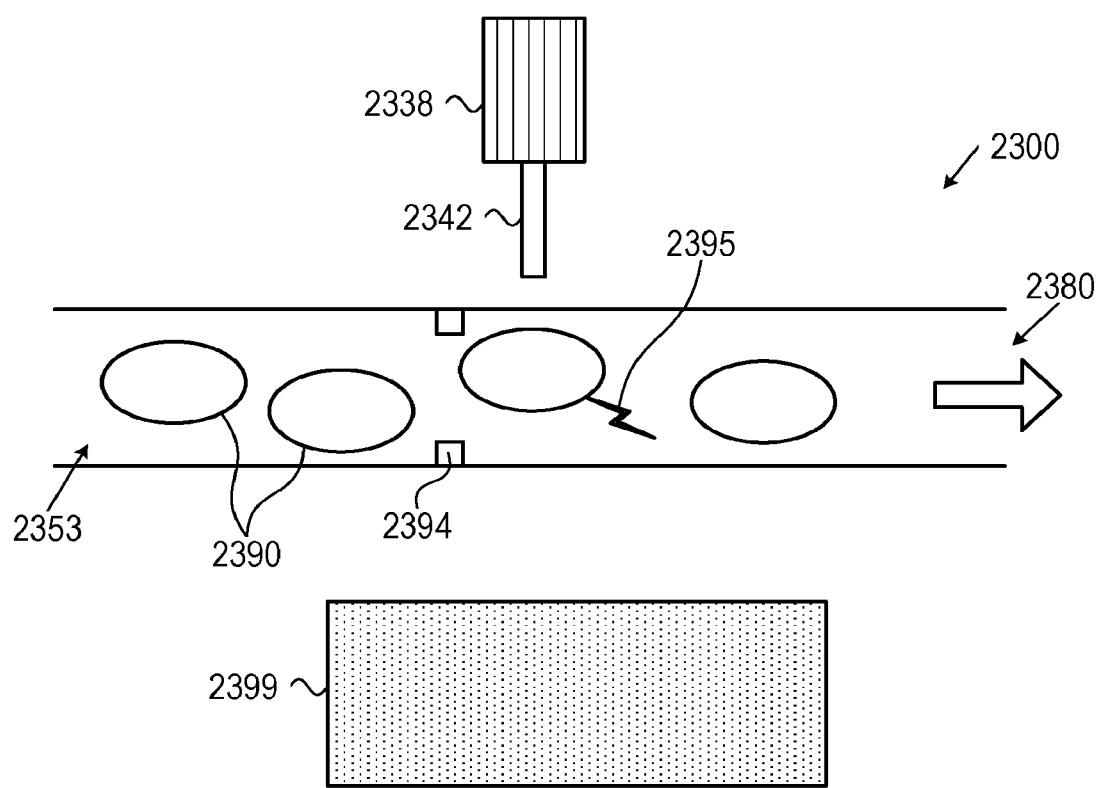
Figure 24:
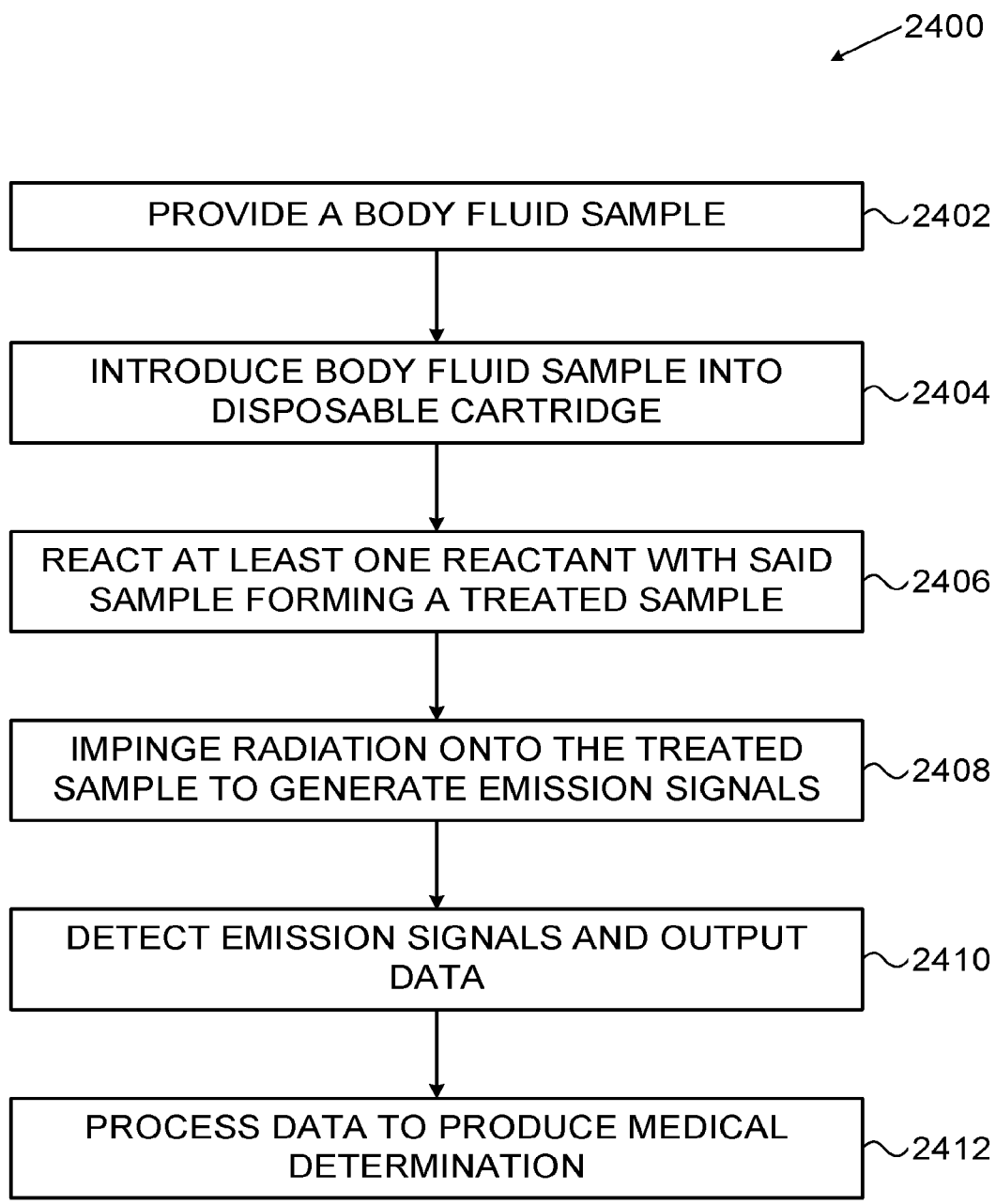
Figure 25:
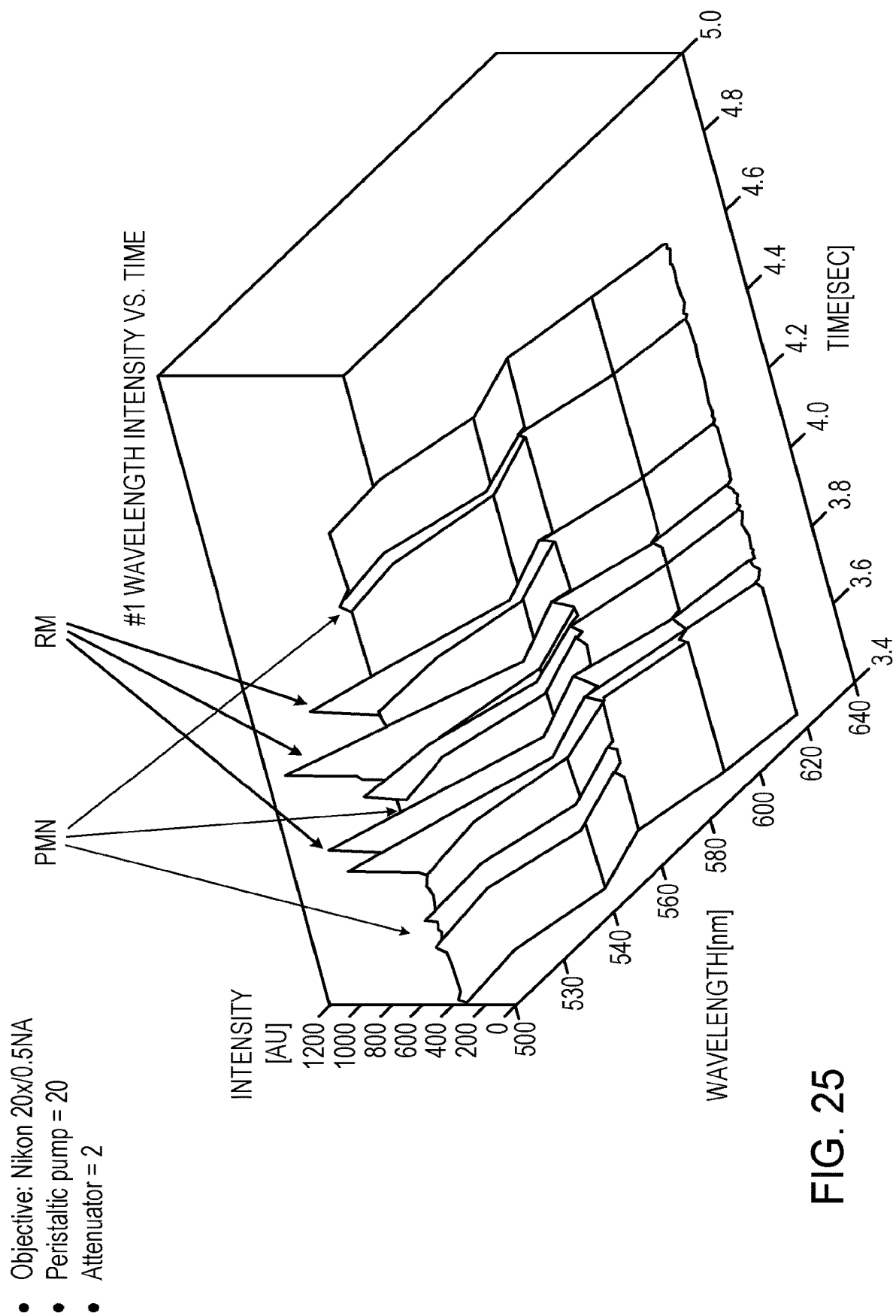
Figure 26A:
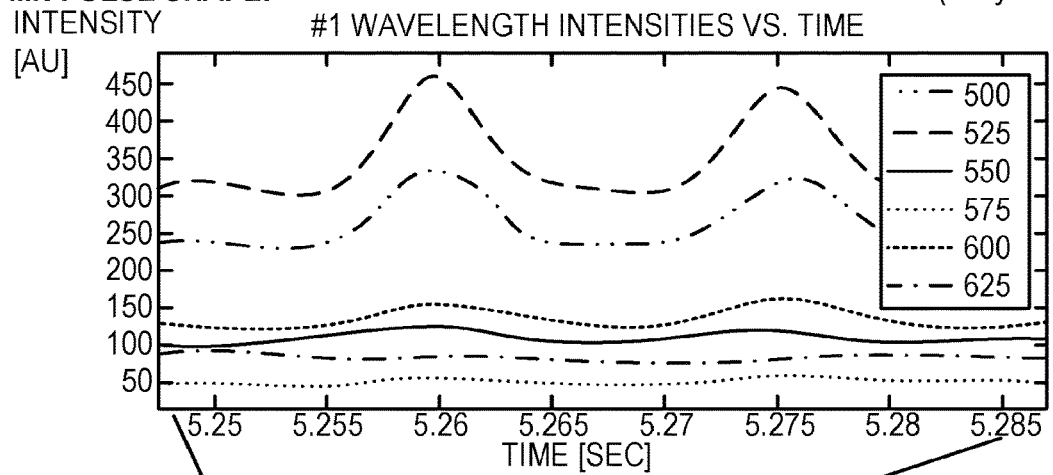
Figure 26B:
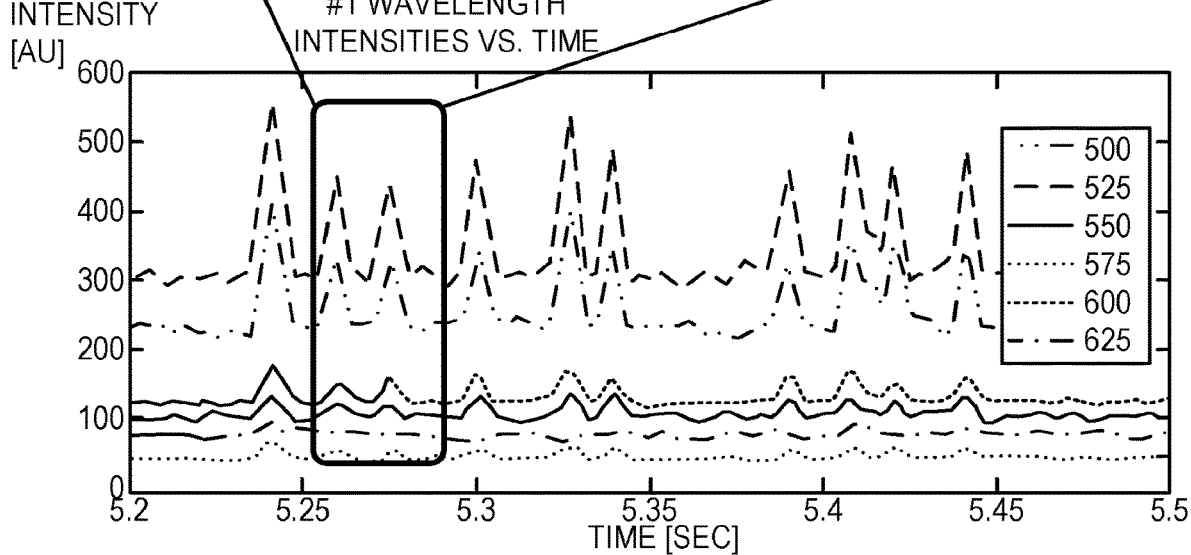
Figure 26C:
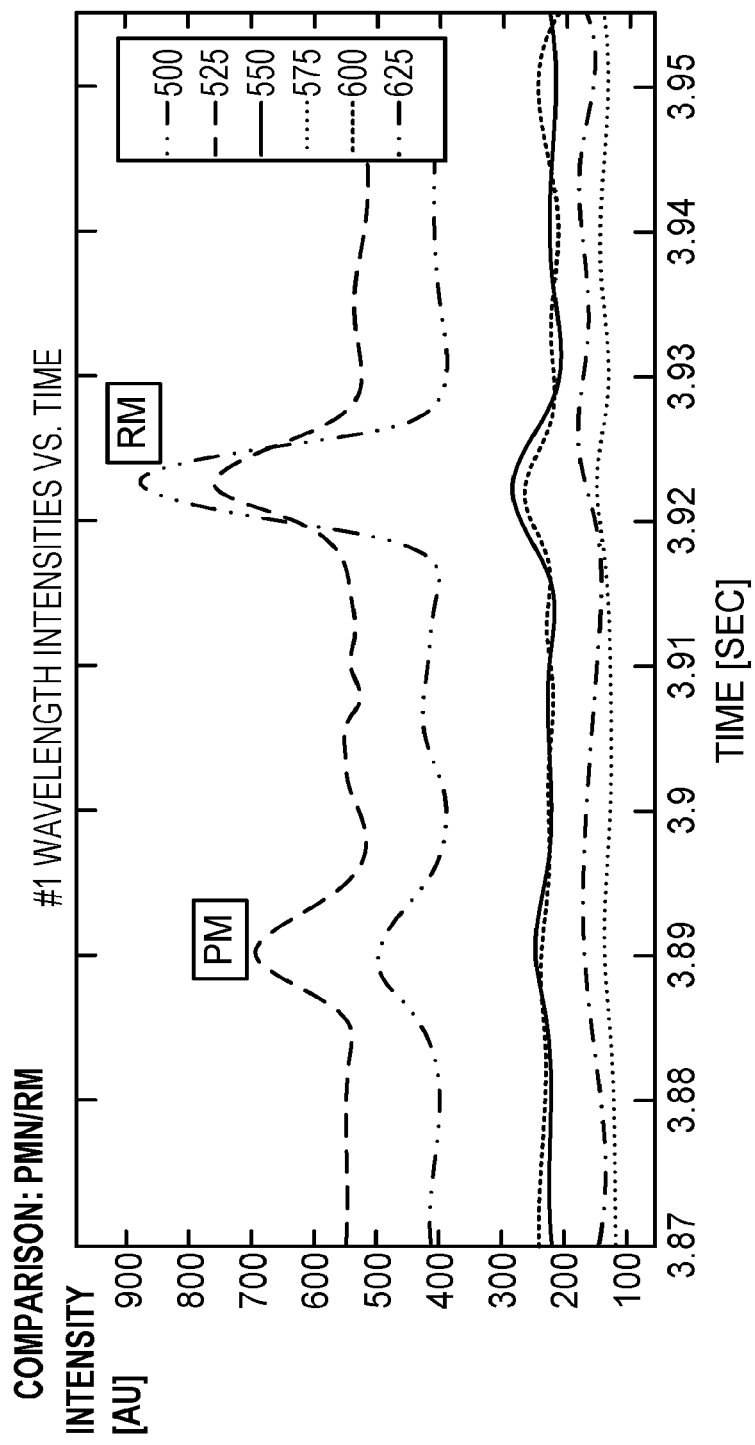

FIG. 23A is a schematic view of a sampling cartridge of the system of FIG. 1, in accordance with an embodiment of the present invention;

FIG. 23B shows a schematic view of disposable cartridge in flow-cytometer device, in accordance with an embodiment of the present invention;

FIG. 24 is a simplified flowchart of a method for rapid determination of a medical condition, in accordance with an embodiment of the present invention;

FIG. 25 is a three-dimensional graph showing the optical output over time of reference beads (RM) relative to a sample from a human patient (PMN), in accordance with an embodiment of the present invention; and FIGS. 26A-26C show graphs of optical outputs over time of the reference beads and the sample from a human patient, in accordance with an embodiment of the present invention.

In all the figures similar reference numerals identify similar parts.

DETAILED DESCRIPTION OF PREFERRED EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

International patent application publication no. WO2011/128893 to Kasdan et al., describes a device, system and method for rapid determination of a medical condition and is incorporated herein by reference.

The microfluidic cartridges of the present invention may be any suitable cartridge as shown in the figures or any of the prior art cartridges described or cited herein, such as, but not limited to, those described in USD669191 S1, US20120266986 A1, EP1846159 A2, US2012275972, WO11094577A, US2007292941A and EP1263533 B1.

Reference is now made to FIG. 1, which is a simplified schematic illustration showing an apparatus 100 for detecting a biological condition, in accordance with an embodiment of the present invention.

Apparatus 100 is a kit comprising a cartridge 102 and a number of chemical/biochemical reactants termed herein, treatment compositions. The treatment compositions are adapted to react, at least in part, with biological specimen, such as a body specimen, to be introduced to the apparatus. The body specimen may be a bodily fluid such as, but not limited to, blood, serum, plasma, urine, saliva, cerebrospinal fluid (CSF), serous fluid, peritoneal fluid and synovial fluid. Additionally or alternatively, the body specimen may be a solid such as a hair, a tooth part, a bone part or a piece of cartilage.

Apparatus 100 comprises a specimen receiving element 118, adapted to transfer the specimen to a sample composition chamber 104. The sample composition chamber comprises on or more transfer elements 105, adapted to transfer the specimen from the sample composition chamber to one or more other locations in the cartridge. In the non-limiting example shown in FIG. 1, transfer element 105 is a conduit in fluid connection with a treatment chamber 112. These conduits may appear in other figures herein, and are, in some cases, microfluidic channels. Hie microfluidic channels may have, in some embodiments, a cross-section of 0.1 to 2 $mm^2$.

Additionally, the cartridge comprises a number of treatment composition chambers 106, 108, 110, adapted to respectively house a corresponding number of treatment compositions 120, 122, 124. These chambers are also termed "blisters" herein. These treatment compositions may be liquid, solid or combinations thereof. Apparatus 100 is typically sold commercially as a kit with the treatment compositions disposed therein. In some cases, the kit may be adapted for a one-off test and may be a disposable kit. In other cases, the kit may be re-used. A re-usable kit may be adapted to receive additional external compositions (not shown) or may have a plurality of treatment compositions, wherein only a portion is used for each test.

The apparatus may be constructed and configured such that the treatment composition comprises proteins attached to a surface, such as to beads. A plurality of beads or other structural elements with proteins attached to their surfaces by any one or more of the following methodologies:—

- simple attachment such as by adsorption via electrostatic or hydrophobic interactions with the surface, entrapment in immobilized polymers, etc.
- covalent bonding of the protein to the bead surface
- biological recognition (e. g., biotin/streptavidin).
- requires two steps: a first layer is formed by silane chemistry such that the surface presents a reactive group (e. g., epoxy, amino, thiol, etc.), and a second layer (e. g., the protein to be immobilized or a linker molecule) is covalently attached via the immobilized reactive groups.
- covalent attachment to functionalized polymer coatings on the interior of the device or linkage to the free end of a self-assembled monolayer (SAM) on a gold surface.

The reaction type may include any one or more of antigen-antibody binding, sandwich (such as antibody-antigen-antibody), physical entrapment, receptor-ligand, enzyme-substrate, protein-protein, aptamers, covalent bonding or biorecognition.

Cartridge 102 further comprises at least one transfer element 107, 109, 111 in fluid communication with each respective of treatment composition chamber, each transfer element also being in fluid communication with treatment chamber 112.

Various methodologies for transferring the contents of the treatment composition chambers and the sample composition chamber via the transfer elements to the treatment chamber may be employed, some of which are known in microfluidics technologies. These include air blowing, suction, vacuuming, mechanical transfer, pumping and the like.

Cartridge 102 further comprises at least one transfer element 113 in fluid communication with treatment chamber 112 and with an evaluation chamber 114.

Optionally, evaluation chamber 114 is further in fluid communication with a transfer element 115, adapted to remove the contents of the evaluation chamber for disposal outside the cartridge. Alternatively, the evaluation chamber may have no external disposal means.

Table 1 shows some representative applications of apparatus 100 and methods of the present invention.

TABLE 1

Some Biological Applications of the apparatus and methods of this invention.

| Application | Type of Test | Relevent Figures in this invention | Typical Prior Art Laboratory Turnaround time (TAT)-see references | This Invention Turn around time (TAT) | References |
|---|---|---|---|---|---|
| Application #1 - CD64 Infection & Sepsis | Surface Marker | Figs. 1-2 and 3-5D | 4 hours | 10 minutes | U.S. Pat. No. 8,116,984, Davis, BH et al., (2006) |
| 1 - Fetal Hemoglobin Test | Plasma Protein | Figs. 1-2 and 6-8D | 4 hours | 10 minutes | Dziegiel et al. (2006) |
| 2 - Low Platelet Count | Surface Marker | Figs. 1-2 and 3-5D | 4 hours | 10 minutes | Segal, H.C., et al. (2005): |
| 3 - Resolving BLAST Hag for hematology Lab | Surface Marker | Figs. 1-2 and 3-5D | 4 hours | 10 minutes | Guerti, K., et al. |
| 4 - CD34 Stem Cell Enumeration Assay | Surface Marker | Figs. 1-2 and 3-5D | 4 hours | 10 minutes | Sutherland et al. (1996) |
| 5 - Platelets Activation Assay CD62 | Surface Marker | Figs. 1-2 and 3-5D | 4 hours | 10 minutes | Graff et al. (2002) Divers, S. G., et al. (2003) |
| 6 - D - dimer (Bead based protein) | Plasma Protein | Figs. 1-2 and 6-8D | 4 hours | 10 minutes | Stein et al. (2004) Rylatt, D.B., et al. (1983): |
| 7 - Chorioamnioitis CD64 | Surface Marker | Figs. 1-2 and 3-5D | 4 hours | 10 minutes | Hillier et al. (1988) |
| 8 - CD20 Cell Quantitation (Therapy Monitoring) | Surface Marker | Figs. 1-2 and 3-5D | 4 hours | 10 minutes | Rawstron et al. (2001) Cheson et al. (1996) |
| 9 - CD52 Cell quantitation (Therapy Monitoring) | Surface Marker | Figs. 1-2 and 3-5D | 4 hours | 10 minutes | Rawstron et al. (2001) |
| 10 - Circulating Tumor Cells | Surface Marker | Figs. 1-2 and 3-5D | 4 hours | 10 minutes | Cristofanilliet al. (2004 |
| 11 - Reticulated Platelet Assay | Surface Marker | Figs. 1-2 and 3-5D | 4 hours | 10 minutes | Matic et al. (1998) Ault et all (1993) Wang et al. (2002) |
| 12 - Bacteria Detection in platelet packs | | | 4 hours | 10 minutes | Blajchman et al (2005) McDonald et al. (2005) |
| 13 - Platelet Associated Antibodies | Surface Marker | Figs. 1-2 and 3-5D | 4 hours | 10 minutes | Michelson (1996) |
| 14 - Residual Leukocyte Count in blood products | Surface Marker | Figs. 1-2 and 3-5D | 4 hours | 10 minutes | Bodensteiner, (2003) |
| 15 - CD4 HIV AIDS | Surface Marker | Figs. 1-2 and 3-5D | 4 hours | 10 minutes | Rodriguez (2005). Dieye et al. (2005) |
| 16 - Leukemia Panels - Very complex | Surface Marker | Figs. 1-2 and 3-5D | 4 hours | 10 minutes | Drexler et al (1986) |
| 17 - Bladder Cancer Screening in Urine - Urine sample | Surface Marker | Figs. 1-2 and 3-5D | 4 hours | 10 minutes | Ramakumar et al (1999) Lotan et al. (2009) |
| 18 - HLA DR Sepsis and Immuno-suppression | Surface Marker | Figs. 1-2 and 3-5D | 4 hours | 10 minutes | Hershman et al. (2005) Perry et al (2003) |

TABLE 1-continued

Some Biological Applications of the apparatus and methods of this invention.

| Application | Type of Test | Relevent Figures in this invention | Typical Prior Art Laboratory Turnaround time (TAT)-see references | This Invention Turn around time (TAT) | References |
|---|---|---|---|---|---|
| 19 - RECAF Protein for Canine and other Cancers | Plasma Protein | Figs. 1-2 and 6-8D | 4 hours | 10 minutes | Moro et al. (2005). |
| 20 - CytoImmun Cervical Screening | | | 4 hours | 10 minutes | Hilfrich et al. (2008) |
| 21 - Procalcitonin (Bead Based Protein) + Feasibility | Plasma Protein | Figs. 1-2 and 6-8D | 4 hours | 10 minutes | Assicot et al. (1993) Christ-Crain et al. (2004) |

Figure 2:
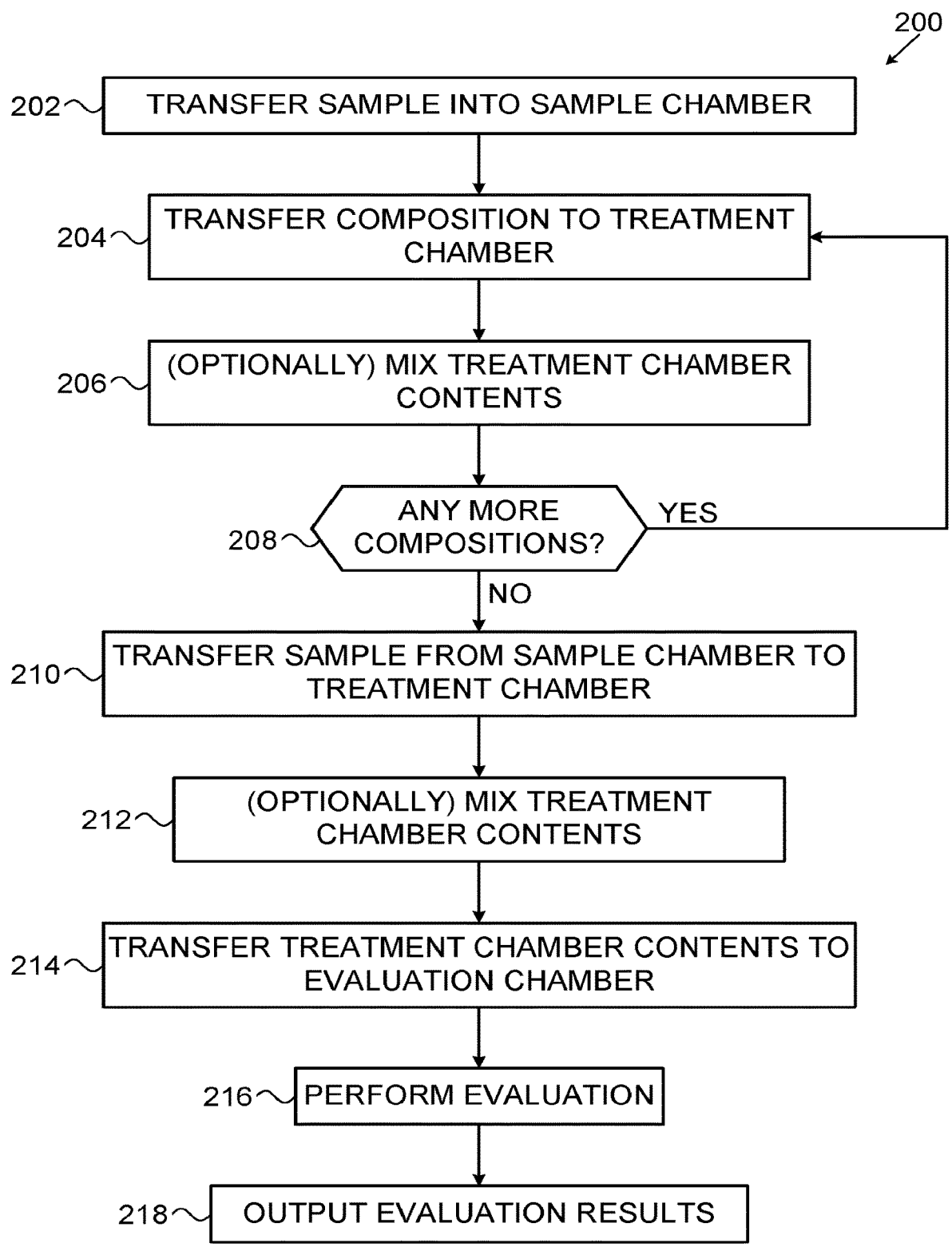

Reference is now made to FIG. 2, which is a simplified flow chart 200 of a method for detecting a biological condition, in accordance with an embodiment of the present invention.

It should be understood that each of the steps of the method may take a predetermined period of time to perform, and in between these steps there may be incubation and/or waiting steps, which are not shown for the sake of simplicity.

In a sample transferring step 202, a sample, such as a bodily specimen is transferred from outside apparatus 100 via receiving element 118 into sample composition chamber 104. According to some embodiments, the volume of the specimen or sample is less than 200 µL, less than 100 µL, less than 50 µL, less than 25 µL or less than 11 µL.

Thereafter, treatment composition 120 is transferred via transfer element 107 to the treatment chamber in a composition transfer step 204. In some cases, there may be a treatment composition or liquid (not shown) disposed in the treatment chamber.

Depending on the nature of the treatment composition and sample/specimen type, there may be a requirement to mix or agitate the treatment chamber contents in an optional mixing step 206. This may be performed by using a small stir-bar (not shown) disposed in the chamber. Additionally or alternatively, this may be effected by the fluid dynamics of kit. Additionally or alternatively, stirbars may be disposed in any of the other chambers in the apparatus.

Hie sequence of transfer of the various treatment compositions may be important to the reaction sequence and is typically predefined. Steps 204-206 may be performed, for example on treatment composition chamber 106, thereafter on treatment composition chamber 108 and thereafter on treatment composition chamber 110. In some cases, some of these steps may be performed concurrently.

In a checking step 208, it is ascertained whether all the compositions required for the sample treatment have been transferred to the treatment chamber. If any compositions remain, then steps 204-206 are performed on the subsequent treatment composition chamber(s). If no further treatment compositions require transfer, then the sample/specimen is transferred from chamber 104 into the treatment chamber.

Thereafter, in a second sample transfer step 210, the sample is transferred from the sample composition chamber into the treatment chamber.

According to some embodiments, step 210 may be performed before steps 204-208.

If required, an optional mixing step 212 to the contents of the treatment chamber may be performed.

In a transferring step 214, the contents of the treatment chamber are transferred to the evaluation chamber.

Hie evaluation chamber 114 is configured and constructed for one or more evaluation steps 216. These may include any combination or permutation of the following:
 a) transfer of radiation there-through,
 b) impinging radiation thereupon;
 c) detecting reflected and/or refracted radiation,
 d) detecting emitted radiation;
 e) capturing one or more images thereof;
 performing image analysis on the captured images;
 g) measuring electrical characteristics of the treated specimen;
 h) impinging sonic energy thereon;
 i) detecting sonic energy therefrom; and
 j) analyzing the outputs of any one or more of the above steps.

According to some embodiments, the cartridge is introduced into a system as described in International patent application publication no. WO2011/128893, to Kasdan et al., incorporated herein by reference.

The results of the evaluation step are then outputted in a results outputting step 218.

According to some embodiments; the apparatus may have on-board means for showing a result, such as a colorimetric strip (not shown). Additionally or alternatively, the results are displayed in a display unit, separate and remote from apparatus 100.

The time required to complete an assay using apparatus 100 varies depending on a number of factors, with non-limiting examples that include described herein. In some embodiments, the time required to complete an assay is from about 0.5 to 100 minutes. In other embodiments, the time required to complete an assay is from about 1 to 20 minutes. In still other embodiments, the time required to complete an assay is from about 1 to 10 minutes. In some examples, the time required to complete an assay is from about 1, 2, 3, 4, 5, 6, 7, 8, 9, 10, 15, 20, 25, 30, 35, 40, 50, 60, 80, or 100 minutes.

Figure 3:
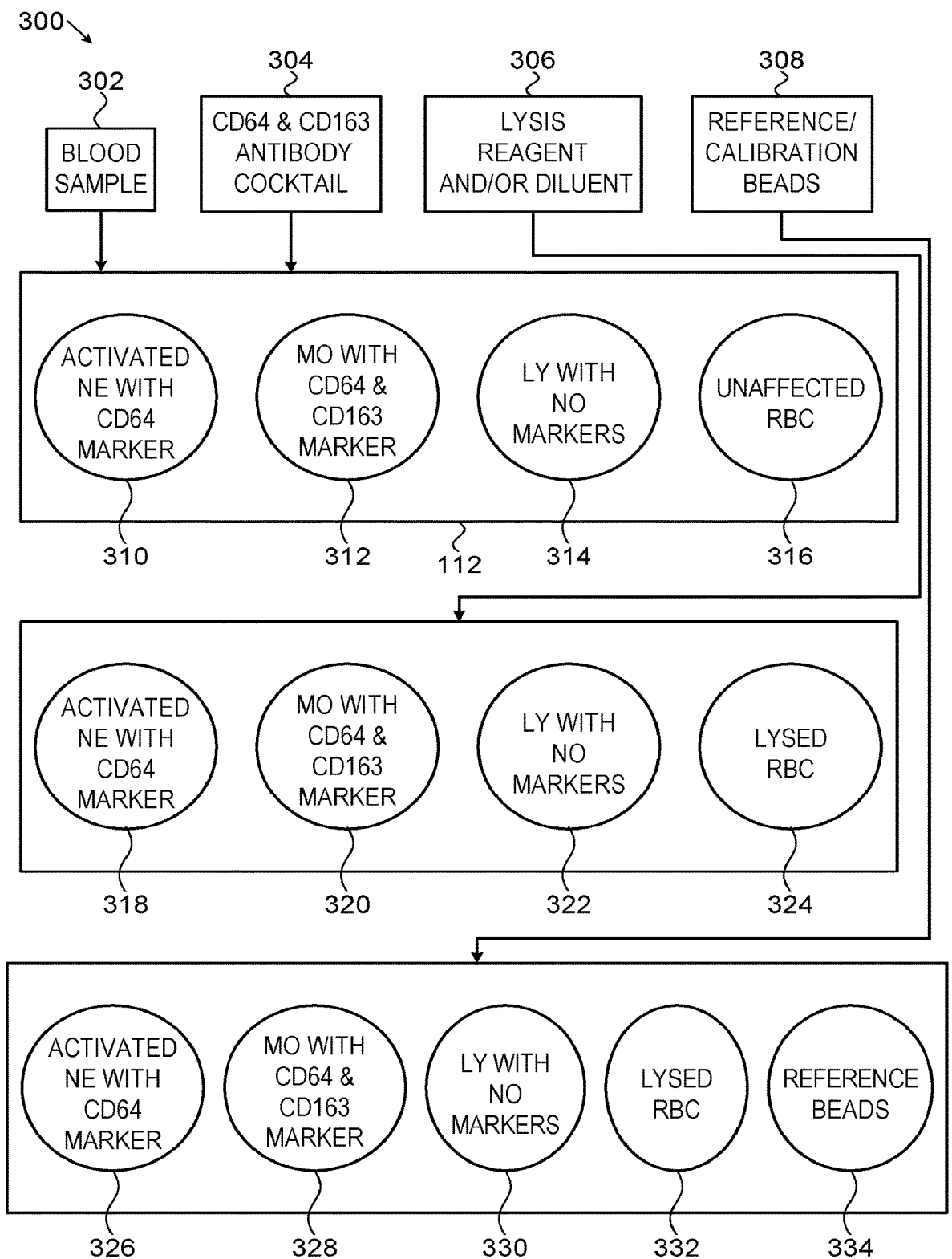

Reference is now made to FIG. 3, which is a simplified schematic illustration showing a methodology 300 for detecting a biological condition associated with a CD64 cell surface antigen, in accordance with an embodiment of the present invention.

According to some embodiments, the method is carried out in the apparatus shown in FIG. 1 and as described herein. A biological specimen, such as a blood sample, is aspirated via specimen receiving element 118 to sample composition chamber 104, and then to treatment chamber 112. The sample is typically of a volume in the range of 10-200 µL.

The blood sample is typically whole blood recently removed from a patient. The whole blood comprises mainly red blood cells (also called RBCs or erythrocytes), platelets and white blood cells (also called leukocytes), including lymphocytes and neutrophils. Increased number of neutrophils, especially activated neutrophils are normally found in the blood stream during the beginning (acute) phase of inflammation, particularly as a result of bacterial infection, environmental exposure and some cancers.

A cocktail 304 comprising antibodies to CD64 and antibodies to CD163 is introduced to the treatment chamber (see Davis et al. (2006)). Each antibody type is typically tagged by a specific fluorescent tag. The fluorescent tag is designed, in some cases, to be activated when the antibody binds to its antigen. In other cases, it is always active.

The contents of the chamber are incubated and/or mixed as is required to bind the activated blood neutrophils with the CD64 tagged antibody (also called a marker) to form activated neutrophils with CD64 marker 310, and/or monocyte with a CD64 tagged antibody and a CD163 tagged antibody 312. Lymphocytes with no markers 314 are present in the contents, as well as unaffected RBCs 316.

Thereafter, a lysis reagent or diluent 306 is introduced into treatment chamber 112. In the case of a lysis reagent, it is adapted to lyse red blood cells to form lysed red blood cells 324. Additionally, reference/calibration beads 308 are added to the treatment chamber. These are used to calibrate the outputs, as is explained with reference to FIGS. 5A-5D hereinbelow.

CD64 (Cluster of Differentiation 64) is a type of integral membrane glycoprotein known as an Fc receptor that binds monomeric IgG-type antibodies with high affinity. Neutrophil CD64 expression quantification provides improved diagnostic detection of infection/sepsis compared with the standard diagnostic tests used in current medical practice.

CD 163 (Cluster of Differentiation 163) is a human protein encoded by the CD 163 gene. It has also been shown to mark cells of monocyte/macrophage lineage.

Figure 4:
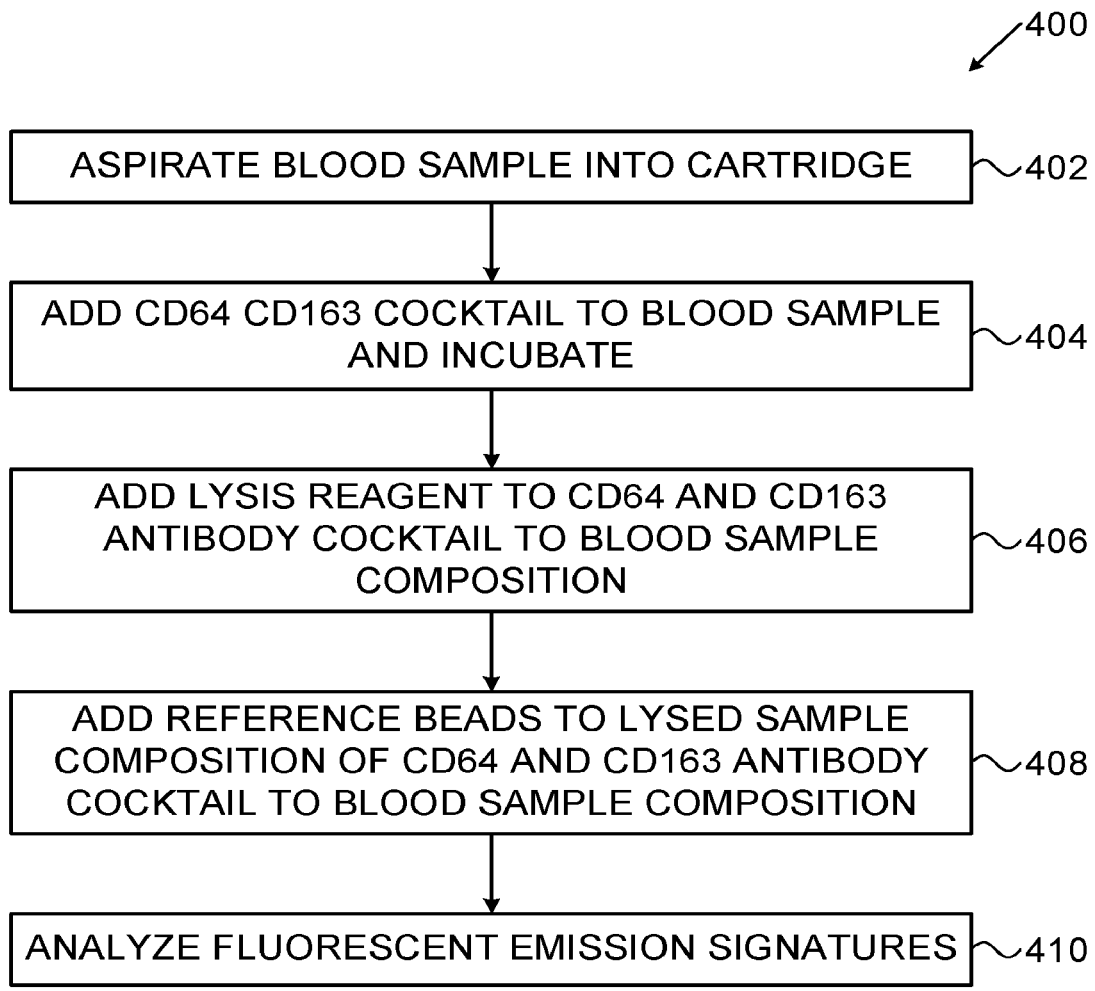

Reference is now made to FIG. 4, which is a simplified flow chart 400 of a method for detecting a biological condition associated with a CD64 cell surface antigen, in accordance with an embodiment of the present invention.

According to some embodiments, the method is carried out in the apparatus shown in FIG. 1 and as described herein. In a first transferring step 402, a biological specimen, such as a blood sample is aspirated via specimen receiving element 118 to sample composition chamber 104 and then to the treatment chamber 112. The sample is typically of a volume in the range of 10-200 µL.

In an addition step 404, a cocktail of tagged antibodies to CD64 and to CD163 is added to the treatment chamber 112 and is mixed and incubated with the blood sample. In the incubation phase of this step, the antibodies bind activated neutrophils with CD64 marker 310, and/or monocytes activated with a CD64 tagged antibody and a CD163 tagged antibody 312.

In a lysis reagent addition step 406, the lysis reagent is added to the treatment chamber and thereby lyses at least some of the RBCs in the chamber.

At any suitable time, typically following lysis step 406, reference beads are added to the contents of the treatment chamber in a reference bead adding step 408.

After a predefined period of time, an analysis step 410 is performed to analyze the fluorescent emission signatures from the contents. This is described in further detail with reference to FIGS. 5A-5D. According to some examples, the evaluation chamber 114 is constructed and configured to allow cells to pass through a reading zone 130 such that each cell passing therethrough is analyzed individually.

Figure 5A:
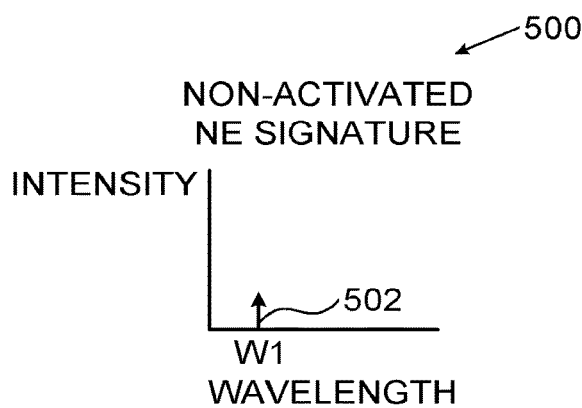

Reference is now made to FIG. 5A, which is a graphical output of a fluorescent detection assay of a non-activated neutrophil signature 500 associated with the method of FIGS. 3-4, in accordance with an embodiment of the present invention. The non-activated tagged neutrophils each emit a signal 502 at wavelength W1 of an intensity $I_1$.

Figure 5B:
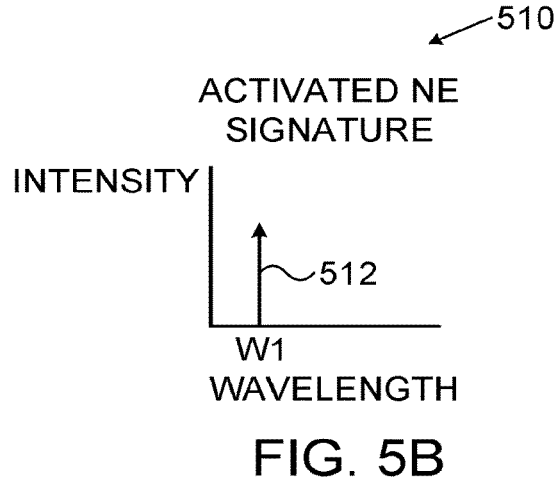

FIG. 5B shows a graphical output of a fluorescent detection assay of an activated neutrophil signature 510, associated with the method of FIGS. 3-4, in accordance with an embodiment of the present invention. Each activated tagged neutrophil emits an activated neutrophil signature 512 at wavelength W1 of an intensity $I_2$. Typically $I_2$ is greater than $I_1$. In some cases the difference in signatures 512 and 510 may be detected by an image analysis, a fluorescent emission radiation count or by other qualitative or quantitative methods known in the art. The current example is not meant to be limiting.

Figure 5C:
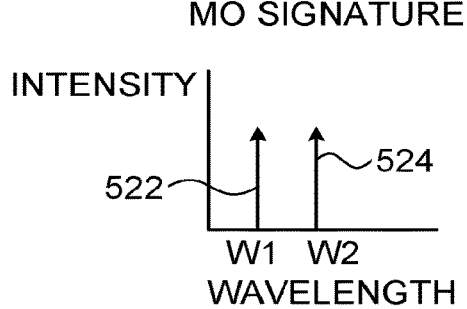

Turning to FIG. 5C, there can be seen a graphical output of a fluorescent detection assay of a monocyte signature 520, associated with the method of FIGS. 3-4, in accordance with an embodiment of the present invention. The monocyte signature comprises a first signal 522 at a first wavelength W1 of an intensity $I_3$ and a second signal 524 at a second wavelength W2 of an intensity $I_4$.

Figure 5D:
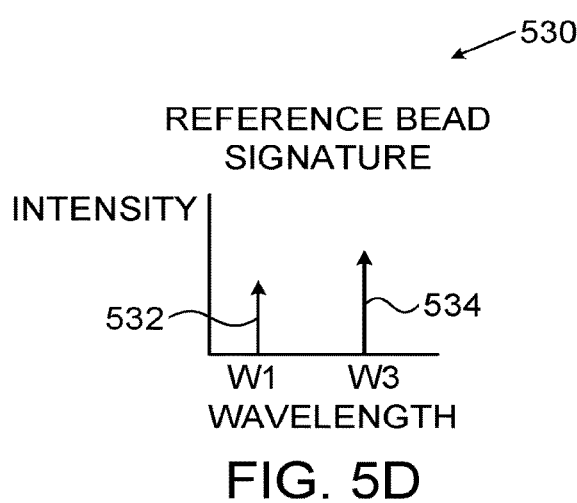

FIG. 5D shows a graphical output of a fluorescent detection assay of a reference bead signature 530, associated with the method of FIGS. 3-4, in accordance with an embodiment of the present invention. The reference bead signature comprises a first signal 532 at a first wavelength W1 of an intensity $I_1$ (similar or equal to non-activated tagged neutrophils' signal 502) and a second signal 534 at a second wavelength W3 of an intensity $I_5$.

This methodology enables the identification and quantification of activated neutrophils by intensity of signature 512 of the CD64 tag. Monocytes are identified by the double signal signature 522, 524, acting as a positive control. Reference beads are identified by the unique signal 534 at wavelength W3. The intensity of signal 532 at wavelength W1 provides a reference level of the CD64 tag for the comparison of intensity of 512 of the neutrophils.

Lymphocytes with no markers 330 (FIG. 3) act as a negative control and should provide no fluor signature, but may be detected by their scattering or other characteristics. Further details of some embodiment of this assay procedure are described in U.S. Pat. No. 8,116,984 and in Davis, B H et al., (2006).

Reference is now made to FIG. 6, which is a simplified schematic illustration showing a methodology 600 for detecting a biological condition associated with a plasma protein, in accordance with an embodiment of the present invention;

According to some embodiments, the method is carried out in the apparatus shown in FIG. 1 and as described herein. A biological specimen, such as a blood sample 602, is aspirated via specimen receiving element 118 to sample composition chamber 104, and then to treatment chamber 112. The sample is typically of a volume in the range of 10-200 μL.

The blood sample is typically whole blood recently removed from a patient. Hie whole blood comprises mainly red blood cells (also called RBCs or erythrocytes), platelets and white blood cells, including lymphocytes and neutrophils. Hie blood sample contains at least one protein target antigen. Beads covered in protein antibodies 604 are prepared, for example in accordance with Bangs Laboratories Product Data Sheet 854 procedure for Flow Cytometry Protein G Antibody Binding Beads catalog number 554.

Beads 604 are introduced to treatment chamber 112 and the blood sample 602 is also introduced. Thus at this stage of the treatment, there are some beads which have bound the (plasma) protein target 612, some beads which remain without any bound protein target antigen 610, unaffected white blood cells 614, unaffected platelets 616 and unaffected RBCs 618.

Each antibody type is typically tagged by a specific fluorescent tag. The fluorescent tag is designed, in some cases, to be activated when the antibody binds to its antigen. The contents of the chamber are incubated and/or mixed as is required to induce the antigen-antibody binding.

Thereafter, a plasma protein fluor tagged antibody composition 606 is added to the chamber and mixed/incubated, thereby forming plasma protein captured on antibody beads with fluor marker 620, as well as unbound beads 619, similar or identical to unbound beads 610. Additionally, unaffected white blood cells 622 similar or identical to 614, unaffected platelets 624, similar or identical to 616 and unaffected RBCs 626, similar or identical to 618.

Additionally, reference/calibration beads 608 are added to the treatment chamber. These are used to calibrate the outputs, as is explained with reference to FIGS. 8A-8D hereinbelow. The plasma protein captured on antibody beads with fluor marker 628 (similar or identical to 620), and the other components unbound beads 629 (similar or identical to 619), unaffected white blood cells 630 (similar or identical to 622), unaffected platelets 624 (similar or identical to 624) and reference beads 636 (similar or identical to 608) are now ready for evaluation in accordance with the method of FIG. 7 described in further detail hereinbelow.

FIG. 7 shows a simplified flow chart of a method 700 for detecting a biological condition associated with a plasma protein, in accordance with an embodiment of the present invention.

According to some embodiments, the method is carried out in the apparatus shown in FIG. 1 and as described herein. In a first transferring step 702, a biological specimen, such as a blood sample is aspirated via specimen receiving element 118 to sample composition chamber 104 and then on to treatment chamber 112. The sample is typically of a volume in the range of 10-200 μL.

In an addition step 704, a beads covered in plasma protein antibody 604 are added to the treatment chamber 112 and is incubated with the blood sample. In the incubation phase of this step, the antibodies on the beads bind some or all of the protein target antigen forming bound plasma protein on antibody beads 612.

In a plasma protein fluor tagged antibody addition step 708, plasma protein fluor tagged antibody 606 is added to the treatment chamber.

At any suitable time, typically following addition step 706, reference beads are added to the contents of the treatment chamber in a reference bead adding step 708.

After a predefined period of time, an analysis step 710 is performed to analyze the fluorescent emission signatures from the contents. This is described in further detail with reference to FIGS. 8A-8D. According to some examples, the evaluation chamber 114 is constructed and configured to allow cells to pass through a reading zone 130 such that each cell passing therethrough is analyzed individually.

Reference is now made to FIG. 8A, which is a graphical output of a fluorescent detection assay of plasma protein beads with a no target binding signature 800, associated with the method of FIGS. 6-7, in accordance with an embodiment of the present invention. The plasma protein target beads with no binding of target antigen 604 each emit a signal 802 at wavelength W1 of an intensity $I_1$.

Reference is now made to FIG. 8B, which is a graphical output of a fluorescent detection assay of an unbound tagged antibody signature 810, associated with the method of FIGS. 6-7, in accordance with an embodiment of the present invention.

Each unbound tagged target antibody 606 emits an unbound tagged target antibody signature 810 at wavelength W2 of an intensity $I_2$.

FIG. 8C is a graphical output of a fluorescent detection assay of plasma protein target beads with target binding signature 820, associated with the method of FIGS. 6-7, in accordance with an embodiment of the present invention.

Signature 820 comprises a first signal 822 at a first wavelength W1 of an intensity $I_3$ and a second signal 824 at a second wavelength W2 of an intensity $I_4$. Typically $I_4$ is greater than $I_2$. In some cases the difference in signatures 812 and 810 may be detected by an image analysis, a fluorescent emission radiation count or by other qualitative or quantitative methods known in the art. The current example is not meant to be limiting.

FIG. 8D is a graphical output of a fluorescent detection assay of a reference bead signature 830, associated with the method of FIGS. 6-7, in accordance with an embodiment of the present invention.

The reference bead signature comprises a first signal 832 at a first wavelength W2 of an intensity $I_5$ (similar to unbound tagged target antibody 606 that emits an unbound tagged target antibody signature 810 at wavelength W2) and a second signal 834 at a second wavelength W3 of an intensity $I_6$.

In summary of analysis step 710 (FIG. 7), the cells may be passed through reading zone 710 individually. Beads 604 without bound target protein are identified by the presence of target bead fluor signal 802 at W1. The overall level of fluorescence determines the level of protein in the sample. Beads with bound target protein emit signature 820 both the bead fluor signal W1, 822 (similar or identical to 802) and sandwich fluor tag W2, 824, as is shown in FIG. 8C.

Reference beads 608 are identified by a unique fluor W3 signal 834. The level/intensity of W2 in the plasma protein target beads with target binding signature 820 is compared to that of first signal 832 at a first wavelength W2 of an intensity Is of the reference beads to determine the overall level of target protein concentration in the sample.

EXAMPLES

Example 1

Application No. 1—CD64 Infection & Sepsis

A cartridge 102 (FIG. 1) is prepared for receiving a blood sample. The cartridge comprises a number of treatment composition chambers 106, 108, 110, adapted to respectively house a corresponding number of treatment compositions 120, 122, 124. These compositions are described in further detail in U.S. Pat. No. 8,116,984 and in Davis, B H et al., (2006)), incorporated herein by reference. In brief, Reagent A comprises a mixture of murine monoclonal antibodies (contains buffered saline), Reagent B—10× Concentrated Trillium Lyse solution (contains ammonium chloride), Reagent C—suspension of 5.2 µm polystyrene beads labeled with Starfire Red and fluorescein isothiocyanate (FITC), (contains <0.1% sodium azide and 0.01% Tween 20).

In a sample transferring step 202 (FIG. 2), a 104, blood sample, is transferred from outside apparatus 100 via receiving element 118 into sample composition chamber 104, and then on to treatment chamber 112 in a transferring step 214.

An antibody composition (Reagent A) 120 comprising CD64 antibodies is transferred via transfer element 107 to the treatment chamber in a composition transfer step 204.

These two steps combined with mixing step 206 take around four minutes using cartridge 102 of the present invention.

A lysis buffer (Reagent B) 122 is also added and mixed with the resultant mixed composition. This step and mixing all the compositions takes around three minutes using cartridge 102 of the present invention. Reference beads (Reagent C) 308 are added to the treatment chamber.

The evaluation chamber 114 is configured and constructed for one or more evaluation steps 216.

According to some embodiments, the cartridge is introduced into a system as described in International patent application publication no. WO2011/128893 to Kasdan et al., incorporated herein by reference. This system has software associated therewith for computing the CD64 and CD163 indices on leukocytes.

The results of the evaluation step are then outputted in a results outputting step 218. According to this example, the time taken from the introduction of the small blood sample to obtaining an indication of sepsis is less than 15 minutes, typically around 10 minutes (see comparison of prior art and the present invention methodologies in Table 2).

From a user point of view, the following steps are performed:

1) The user adds drop of blood to the cartridge 102 and seals it. (10 µL are metered out by microfluidics)
2) Blister A (106) is pressed, releasing 100 µL of Reagent A. Mixing in the cartridge is controlled by the cartridge handling unit (CHU), followed by a 4-minutes incubation.
3) Blister B (108) is pressed, releasing ~250 µL of Reagent B. Mixing in the cartridge is controlled by the CHU, followed by a 3-5-minutes incubation.
4) Magnetic stirbar is activated, stirring the bead suspension (Reagent C)
5) Blister C (110) is pressed, releasing 100 µL of Reagent C. Mixing in the cartridge is controlled by the CHU. According to one example, Reagent A is a mixture of murine monoclonal antibodies—diluted 1:5 in buffered saline (PBS+0.5% BSA); Reagent B is a *Trillium* Lyse solution (at working concentration); Reagent C is a suspension of 5.2 µm polystyrene beads labeled with Starfire Red and FITC, diluted 1:100 in PBS+0.01% Tween 20.
6) The sample is read by the optoelectronics core, and the data is collected.
7) Data is analyzed automatically and result is presented.
8) The cartridge is disposed as biohazard.

TABLE 2

Comparison of Prior art methodology with the methodology of the present invention for detecting sepsis using CD64 and CD163 antibodies.

| | | Trillium kit (FACS)- (prior art U.S. Pat. No. 8,116,984, Davis, BH et al., (2006)) | | LeukoDx device- present invention | | |
| --- | --- | --- | --- | --- | --- | --- |
| Step | Description | Volume (uL) | Duration (min) | Volume (uL) | Duration (min) | comments |
| 1 | Mixing blood and antibodies | Blood-50 Abs-50 | 10 | Blood-10 Abs-50 | 4 | |
| 2 | Adding RBC lysis buffer | 900 | | 250 | 3 | Might require heating the buffer to 37 C. |
| 3 | Incubating, Vortexing | | 15 | | 3 | |
| 4 | Adding normalization beads | 5 | Less than 1 | 2 | Less than 1 | |
| 5 | Reading | | 1 | | Less than 1 | |
| | Total | 1005 | 26-30 min. | 312 | 10 min. | |

Example 2

Application No. 2—Fetal Hemoglobin Test

A fetal hemoglobin test is performed using a cartridge comprising compositions as described in Dziegiel et al. (2006). The test is performed using the methodology described in FIGS. 1-2 and 6-8D.

According to some embodiments, the cartridge is introduced into a system as described in International patent application publication no. WO2011/128893 to Kasdan et al., incorporated herein by reference. This system uses LeukoDx Software—to analyze data collected and stored in a format similar to flow cytometric listmode files. The test takes around 10-15 minutes from the introduction of the sample to receiving a result from the system.

It should be understood that all of the examples listed in Table 1 can be performed using the cartridge of the present invention in combination with the system of WO2011/128893. For each application, a different cartridge is prefabricated using the compositions for the assays, as described in the relevant references (Table 1). The quantities and dilutions thereof are optimized. Typically, the total sample volumes are in the range of 10 to 1000 µL, 100 to 900 µL, 200 to 800 µL, 300 to 700 µL, 400 to 600 µL, or 420 to 500 µL.

According to some embodiments, the volume of the treatment composition chambers 106, 108, 110 (also called blisters) is from about 1 µL to 1000 µL. According to other embodiments, the volume of the specimen is from about 10 µL to 200 µL. According to other embodiments, the volume of the specimen is about 1, 10, 20, 30, 40, 50, 60, 70, 80, 90, 100, 120, 140, 160, 180, 200, 250, 300, 350, 400, 450, or 500 µL.

According to some embodiments, the volume of the treatment compositions 120, 122, 124 is at most about 500 µL. According to other embodiments, the volume of the specimen is at most about 200 µL. According to other embodiments, the volume of the specimen at most about 500, 450, 400, 350, 300, 250, 200, 180, 160, 140, 120, 100, 90, 80, 70, 60, 50, 40, 30, 20, 10, or 1 µL.

According to some embodiments, the volume of a reactant is at least about 1 µL. According to other embodiments, the volume of the specimen is from about 10 µL. According to other embodiments, the volume of the specimen is at least about 1, 10, 20, 30, 40, 50, 60, 70, 80, 90, 100, 120, 140, 160, 180, 200, 250, 300, 350, 400, 450, or 500 µL.

Cartridge 102 may be constructed and configured to enable running multiplex tests on parallel microchannels.

One embodiment of the current design as is suitable for three blisters, representing three different treatments. These treatments could be, for example: a) Direct staining by a fluorescent antibody (or antibody fragments, Fabs); b) Lysis of RBCs and C) Adding internal controls.

Other embodiments disclose two-stage staining, by primary and secondary antibodies, resulting in stronger signals, adding beads (for example magnetic, metallic, polymeric, and antigen-bound beads) for selection or detection of specific cells, proteins, antibodies, auto-antibodies and other biological molecules; tissue sample disintegration cell permeabilization (allowing detection of intracellular proteins); DNA-staining (enables cell counting); RNA-staining (using thiazole orange, enables reticulocyte counts since reticulocytes can be distinguished from erythrocytes by their high content of RNA.); fluorescent staining and/or tagging by aptamers (single-stranded DNA or RNA molecules that can bind to selected targets including proteins and peptides with high affinity); adding substances for enzyme-coupled reactions (stored in separate blisters and mixed upon adding the reagent, for example HRP-conjugated antibodies for chemiluminescent reactions); and adding buffers for washes (note that washing steps will require further design of the cartridge).

Additionally, the present invention includes treatments on the cartridge itself, such as, but not limited to immobilized selective beads can be utilized by passing the solution back and forth on the bed to increase the capture efficiency; filters for cell size, molecule size, and ligand-bound filters (enabling washing steps and/or population selection.

The sample may also include biological tissues, which will require a further step of mechanically disintegrating the tissue sample. For example a skin biopsy: the sample is added to a dedicated port. The port is sealed, and a blister adds a liquid buffer. A dedicated bellow pushes this mixture and disintegrates the tissue either by several push-pull circles, or by pressing it through a mesh.

The cartridge of the present invention may also be used for food/environment safety evaluations: Food/beverage samples for bacteria detection (possibly also allergens detection) and measuring viable bacteria in an environmental sample.

According to some embodiments, the readout may comprise an optoelectronics core, which enables identification and detection of fluorescent signals.

The CCD in the core, used for focusing, can also be used to read chemiluminescent signals. The readout to user may also indicate where the result falls relative to reference ranges.

As can be seen in the Tables herein, there are a large number of applications to the systems, apparatus, cartridges and methods of the present invention and the examples described herein should not be deemed limiting.

Reference is now made to FIG. 9, which is a simplified schematic illustration showing a microfluidics apparatus 900 for detecting a chemical or biochemical entity, in accordance with an embodiment of the present invention.

Apparatus 900 is a kit comprising a cartridge 902 and a number of chemical/biochemical reactants termed herein, treatment compositions. The treatment compositions are adapted to react, at least in part, with a chemical or biological specimen 970, such as a body specimen, to be introduced to the apparatus. The body specimen may be a bodily fluid such as, but not limited to, blood, serum, plasma, urine, saliva, cerebrospinal fluid (CSF), serous fluid, peritoneal fluid and synovial fluid. Additionally or alternatively, the body specimen may be a solid such as a hair, a tooth part, a bone part or a piece of cartilage.

The chemical specimen may be selected, for example, from a liquid sample, a solid sample, a suspension, a colloid, a composition, an ionic solution or any other suitable sample, known in the art.

Apparatus 900 comprises a specimen receiving element 918, adapted to transfer the specimen to a sample composition chamber 904. The sample composition chamber comprises on or more transfer elements 905, adapted to transfer the specimen from the sample composition chamber to one or more other locations in the cartridge. In the non-limiting example shown in FIG. 9, transfer element 905 is a conduit in fluid connection with a treatment chamber 912 at a first end 913 thereof.

Additionally, the cartridge comprises a number of treatment composition chambers 906, 908, 919, adapted to respectively house a corresponding number of treatment compositions 920, 922, 924. These treatment compositions may be liquid, solid or combinations thereof. Apparatus 900 is typically sold commercially as a kit with the treatment compositions disposed therein. In some cases, the kit may be adapted for a one-off test and may be a disposable kit. In other cases, the kit may be re-used. A re-usable kit may be adapted to receive additional external compositions (not shown) or may have a plurality of treatment compositions, wherein only a portion is used for each test.

Cartridge 902 further comprises a gas holding compartment 901, adapted to contain air 950 and/or other gases. In some cases, the gas may be inert, such as nitrogen.

Each treatment composition chamber 906, 908 and 919 has at least one respective conduit 907, 909, 910 in fluid communication with treatment chamber 912.

According to one embodiment, conduits 907, 909 and 910 are disposed in parallel at fixed equal intervals to the treatment chamber.

According to another embodiment, conduits 907, 909 and 910 are disposed in parallel at fixed unequal intervals to the treatment chamber.

Various methodologies for transferring the contents of the treatment composition chambers and the sample composition chamber via the transfer elements to the treatment chamber may be employed, some of which are known in microfluidics technologies. These include air blowing, suction, vacuuming, mechanical transfer, pumping and the like.

Cartridge 902 further comprises at least one transfer element 913 in fluid communication with treatment chamber 912 and with an evaluation chamber 914.

Optionally, evaluation chamber 914 is further in fluid communication with a transfer element 915, adapted to remove the contents of the evaluation chamber for disposal outside the cartridge. Alternatively, the evaluation chamber may have no external disposal means.

According to some examples, the evaluation chamber 914 is constructed and configured to allow some or all of the treated samples to pass through a reading zone 930.

According to some embodiments, fluid transfer element 915 is fluidly connected to at least one vacuum pump or bellows 940.

Apparatus 900 is constructed and configured to introduce a small volume of gas into the treatment chamber, typically by activating the pump 940. Thereafter a small volume of the sample 966 is introduced into the treatment chamber. The alternating introduction of air and further small volumes of samples 964, 962, 960 may be performed a number of times.

According to some embodiments, the treatment chamber is constructed and configured to receive a specific treatment composition for only one small volume of sample. For example, as illustrated in the figure, composition 924 is introduced into small volume of sample 966, composition 922 is introduced into small volume of sample 964, and composition 920 is introduced into small volume of sample 962. Small volume of sample 960 remains untreated and may serve as a control.

According to some additional embodiments, the treatment chamber is constructed and configured to receive a specific treatment composition for all of the small volume of samples sequentially. For example, small volume of sample 966 enters the treatment chamber at first end 913 and is pulled by pump 940 to a position in fluid connectivity with conduit 907 and receives a small amount of treatment composition 920. It is then moved to a position in fluid connectivity with conduit 909 and composition 922 is introduced thereto. Thereafter, sample 966 is moved to another position in fluid connectivity with conduit 910 and composition 924 is introduced into small volume of sample 966. Thereafter small volume of sample 966 is brought via conduit 913 to reading zone 930 in the evaluation chamber.

The reading zone is constructed and configured to enable a number of different detection mechanisms to be effected. Some non-limiting examples of detection mechanisms include:
- image capture
- image analysis
- optical detection
- kinetic study detection
- sound detection
- volume detection
- gas detection
- chromatography The optical detection may be human visual detection, human microscopic examination, or automated machine optical detection. Hie optical detection may involve one or more of detecting at least optical output signal. The output signal may be selected from a transmitted signal, an absorbed signal, a reflected signal, a refracted signal or combinations thereof.

The optical detection may use optical elements and systems external to the cartridge. These may include, for example, optical microscopes, image analyzers, electron microscopes or any other systems known in the art.

After the evaluation has been performed, the small volume of sample may be retained in the chamber or discarded via conduit 915.

Reference is now made to FIG. 10, which is a simplified flow chart 1000 of a method for detecting a chemical or biochemical entity, in accordance with an embodiment of the present invention.

It should be understood that each of the steps of the method may take a predetermined period of time to perform, and in between these steps there may be incubation and/or waiting steps, which are not shown for the sake of simplicity.

In a sample transferring step 1002, a sample, such as a chemical sample specimen 970 is transferred from outside apparatus 900 via receiving element 918 into sample composition chamber 904. According to some embodiments, the volume of the specimen or sample is less than 200 μL, less than 100 μL, less than 50 μL, less than 25 μL or less than 11 μL.

In a pump activating step, pump 940 is activated for a period of time.

In a sample introduction step 906, a first small volume of sample 966 is introduced to the treatment chamber. The volume of the sample 966 may be, for example, less than in the range of 50-100 μL, 25-50 μL, 10-25 μL, or 0-10 μL.

Apparatus may comprise hardware and software elements (not shown), which enable the pre-programming of pump 940, as is known in the art. For example, the pump may be switched on and off at regular predetermined time intervals such that only a small volume of sample 970 can be introduced at any time into the treatment chamber, such as small volume 960. Hie pump may be further actuated to introduce air 380 into the chamber in small volume samples 950 to clean and separate between different small volumes of samples 960, 962, 964 and 966.

In an air introduction step 1008, a small volume of air 950 is transferred from container 901 via an air line 903 into the treatment chamber. The volume of the small volume of air sample 950 may be, for example, less than in the range of 50-100 μL, 25-50 μL, 10-25 μL, or 0-10 μL. The air separates the treated aliquots and cleans the channel to prevent carryover as is known in the art, Skeggs, 1964, 1966.

Steps 1006, 1008 may be repeated a number of times. There may be a decision step 1010 to decide on whether to repeat these steps.

In a treatment composition transfer step 1012, one or more treatment compositions is transferred to a specific region of the treatment chamber via transfer elements/lines 907, 909, 910. The number of treatment compositions introduced into each small volume of sample depends on the nature of the assay/test being performed. As was mentioned hereinabove, each small volume of sample may be treated with one specific composition or a combination of compositions in sequence. Moreover, each treatment composition 920, 922, 924 may each comprises a number of different reagents, markers, cofactors, catalysts, enzymes and combinations thereof.

In some cases, there may be at least one other treatment composition or liquid (not shown) disposed in the treatment chamber.

Depending on the nature of the treatment composition and sample/specimen type, there may be a requirement to mix or agitate the treatment chamber contents in an optional mixing step 413 (not shown).

In some cases, some of these steps 1006, 1008, 1010, 1012 may be performed concurrently.

In a first transferring step 1014, the first small sample 966 after treatment with composition 924 is transferred to the evaluation chamber.

The evaluation chamber 914 is configured and constructed for one or more evaluation steps 1016. These may include any combination or permutation of the following:
- transfer of radiation there-through,
- impinging radiation thereupon;
- detecting reflected and/or refracted radiation,
- detecting emitted radiation;
- capturing one or more images thereof;
- performing image analysis on the captured images;
- measuring electrical characteristics of the treated specimen;
- impinging sonic energy thereon;
- detecting sonic energy therefrom; and
- analyzing the outputs of any one or more of the above steps.

According to some embodiments, the cartridge is introduced into a system as described in International patent application publication no. WO2011/128893 to Kasdan et al., incorporated herein by reference.

Steps 1014, 1016 may be repeated a number of times. There may be a decision step 1018 to decide on whether to repeat these steps. For example, the evaluation step 1016 may be performed on each small volume of sample 966, 964, 962 and 960 sequentially. Additionally or alternatively, evaluation step may be performed a number of times of the same sample, so as to determine kinetic data and the like.

Additionally or alternatively, the evaluation step may be performed at one location in the reading zone or may be performed at a number of sequential locations in the reading zone.

The results of the evaluation step are then outputted in a results outputting step 1020.

According to some embodiments; the apparatus may have on-board means for showing a result, such as a colorimetric strip (not shown). Additionally or alternatively, the results are displayed in a display unit, separate and remote from apparatus 900.

The time required to complete an assay using apparatus 100 or apparatus 900 varies depending on a number of factors, with non-limiting examples that include described herein. In some embodiments, the time required to complete an assay is from about 0.5 to 100 minutes. In other embodiments, the time required to complete an assay is from about 1 to 20 minutes. In still other embodiments, the time required to complete an assay is from about 1 to 10 minutes. In some examples, the time required to complete an assay is from about 1, 2, 3, 4, 5, 6, 7, 8, 9, 10, 15, 20, 25, 30, 35, 40, 50, 60, 80, or 100 minutes.

Reference is now made to FIG. 11, which is a simplified schematic illustration showing a methodology 1100 for detecting and quantifying glucose, protein and albumin in a serum sample, in accordance with an embodiment of the present invention. These tests are for exemplification and should not be deemed as limiting. Details of these tests are found in Schwartz et al., 1974.

According to some embodiments, the method is carried out in the apparatus 900 shown in FIG. 9 and as described herein. A specimen, such as a serum sample, is aspirated via specimen receiving element 918 to sample composition chamber 904, and then to treatment chamber 912. The sample is typically of a volume in the range of 10-200 µL.

The serum sample is typically prepared from a whole blood sample, recently removed from a patient. Air 901 is also introduced into the treatment chamber.

As is seen in FIG. 9, a first small volume of sample (serum 966) appears near to a second end 917 of the treatment chamber. At time zero ($T_0$), no treatment compositions have been mixed with sample 966.

At time $T_1$ after time zero ($T_0$), a first composition (glucose color producing reagent GCPR 1124) is reacted in the sample 1166, (possibly) with glucose therein to form glucose reacted with the GCPR 1166. Any protein 1164, albumin 1162 and other analytes 1160 remain untreated and hence unaffected.

At a time later than $T_1$, such as $T_2$, a protein color producing reagent PCPR 1122) is reacted with another sample 1164, (possibly) with protein therein to form protein reacted with the PCPR 1104. Any glucose 1102, albumin 1106 and other analytes 1108 remain untreated and hence unaffected.

At a time later than $T_2$, such as $T_3$, an albumin color producing reagent ACPR 1120) is reacted with another sample 1162, (possibly) with albumin therein, to form albumin reacted with the ACPR 1116. Any glucose 1112, protein 1114 and other analytes 1118 remain untreated and hence unaffected.

Detection of glucose reacted with the GCPR 1166 in sample 1166, protein reacted with the PCPR 1104 in sample 1164 and albumin reacted with the ACPR 1116 in sample 1162 are then detected using the colorimetric methods described in Schwartz, et al., 1974, for example, in the detection zone 930 of the evaluation chamber 914. The detection may be performed using the systems described in International patent application publication no. WO2011/128893 to Kasdan et al.

Table 3 shows some representative chemical applications of apparatus 100 and methods of the present invention.

TABLE 3

Chemical Applications of the apparatus and methods of this invention.

| Application | Type of Test | Relevant Figs. | Literature References |
|---|---|---|---|
| Blood chemistry parameters, such as albumin, total protein, chloride, carbon dioxide, sodium, potassium, glucose, and urea and nitrogen | Blood chemistry | 1-5 | Skegg et al. 1964 |
| Blood chemistry parameters such as glucose, urea nitrogen, creatinine, carbon dioxide content, total bilirubin, calcium, phosphorus, cholesterol, iron, uric acid, chloride, sodium, potassium, total protein, albumin, creatine kinase, alkaline phosphatase, lactate dehydrogenase, and aspartate and alanine aminotransferases | Blood chemistry | 1-5 | Schwartz et al. (1974) |
| Blood chemistry parameters such as glucose, urea nitrogen, creatinine, carbon dioxide content, total bilirubin, calcium, phosphorus, cholesterol, iron, uric acid, chloride, sodium, potassium, total protein, albumin, creatine kinase, alkaline phosphatase, lactate dehydrogenase, and aspartate and alanine aminotransferases) | Blood chemistry | 1-5 | Westgard et al. (1976) |
| pH, protein, glucose, ketone, bilirubin, blood, Urobilinogen, nitrite, leukocytes, specific gravity | Urinalysis | 1-5 | Free et al., (1972) |

Reference is now made to FIG. 12A, which is a simplified three dimensional front view 1201 of a reader assembly 1200 and cartridge 1210 for detecting a biological condition, in accordance with an embodiment of the present invention;

Shown in FIG. 12A are the reader assembly 1200 and the cartridge 1210. The cartridge is inserted in the reader assembly as shown. Once the cartridge is inserted in the reader assembly all assay pre-analytical processing and analysis are performed automatically. Results of the analysis are displayed on a user interface touchscreen 1215, which is also used to control operation of the reader.

FIG. 12B shows a simplified three dimensional inner front view 1203 of reader assembly 1200 for detecting a biological condition, in accordance with an embodiment of the present invention.

The internal components of the reader assembly are shown in FIG. 12B. There is seen left side view 1220, showing an ITX computer, 1222, a Galil motor controller, 1224, an electronics power supply 1226, cartridge, 110, inserted into a cartridge handling unit (CHU) 128 and a forward scatter detector 1230. Also seen is a right side view 1240 showing reader optics 1242, a data acquisition board 1244 and a general electronics printed circuit board 1246.

FIG. 13A is an outer side view of a cartridge assembly 1300, in accordance with an embodiment of the present invention and FIG. 13B shows an inner side view 1350 of a cartridge assembly 1300, in accordance with an embodiment of the present invention.

FIGS. 14A-14O show a sequence of process events in a cartridge assembly 1400, of the operation of an apparatus 100 (FIG. 1), for detecting a biological condition, in accordance with an embodiment of the present invention.

In FIG. 14A, a blood sample 1401 enters a specimen receiving element 1418 and fills a chamber 1404.

In FIG. 14B, a blister 1420 comprising a treatment composition 120 (FIG. 1) is pressed an antibody cocktail is mixed with 10 micro-liters (μL) of the blood sample.

In FIG. 14C, a mixing bellows 1415 is pressed and this effects mixing of the antibody cocktail and the 10 microliters of the blood sample in a first mixing chamber 1412 to form a first mixture 1403.

In FIG. 14D, the bellows is released and mixture 1403 is siphoned along a tortuous channel 1413 and into a second mixing chamber 1411. Upon release of the bellows, the first mixture returns from the second mixing chamber, back along the tortuous channel to the first mixing chamber. Every time the bellows is pressed the mixture moves towards the second chamber and every time it is released, it returns, wholly or in part to the first chamber. This mixing may be performed multiple times.

In FIGS. 14E-14G, a second composition blister 1422 is pressed, releasing a second composition 122 (FIG. 1), such as a lysis composition thereby forming a second mixture 1405. The second mixture is mixed by pressing of bellows 1415, the second mixture returns from the second mixing chamber, back along tortuous channel 1413 to the first mixing chamber. Every time the bellows is pressed the mixture moves towards the second chamber 1411 and every time it is released, it returns, wholly or in part to the first chamber 1412. This mixing may be performed multiple times.

In FIGS. 14H-14J, a third blister 1424 is released comprising a third composition 124 (FIG. 1), such as a control reference, into the second mixing chamber, thereby forming a third composition 1407. The third mixture is mixed by pressing of bellows 1415, the third mixture returns from the second mixing chamber, back along a tortuous channel 1413 to the first mixing chamber. Every time the bellows is pressed the mixture moves towards the second chamber 1411 and every time it is released, it returns, wholly or in part to the first chamber 1412. This mixing may be performed multiple times.

In FIGS. 14J-14M, a reading bellows 1417 is pressed, which forces some of the third composition towards a reading cuvette 1430.

In FIGS. 14N-14O, particles 1460 from the third composition flow from the cuvette 1430 along a channel 1452 to a reading region 1450. The cells pass through the reading region and are excited by one or more lasers 1462, 1463. At least one excitation laser beam 1464 impinges on cell 1460 and an emission beam 1466 is detected by a detector 1470. In one example, this is cell emission fluorescence and detector 1470 is a spectrometer.

FIG. 15 is a schematic illustration of a micro flow spectrometer reading, in accordance with an embodiment of the present invention;

An individual cell 1505 flows through a detection region 1510 in a microfluidic channel. Additionally, tagged cells 1520 labeled with antibodies conjugated with multiple wavelength fluorescent tags flow through the detection region. A diode laser 1530 impinges a ray/beam 1510 onto the cells and tagged cells. The cells and tagged cells emit different emission spectra (not shown). An optical grating 1540 disperses emission spectra via a grating 1540 into its constituent wavelengths 1550.

A photomultiplier tube (PMT) array 1560 or avalanche diode array detects fluorescence at 8 different spatial locations corresponding to 8 spectral regions.

FIG. 16 shows the main modular components of the reader optics assembly. A complete side view 1620 of the optical assembly is seen, in addition to a top view 1622. A laser unit 1603 includes a laser and beam expander in its heatsink assembly. An excitation and emission collection optics 1604. A photomultiplier (PMT)

FIG. 17 shows details of the photomultiplier (PMT) assembly. A side view and an end view of the PMT assembly are shown as side view 1770 and end view 1772 respectively. The major elements of the PMT assembly include a PMT box 1751, a PMT grating assembly 1752, a PMT bridge assembly 1755, a PMT cover 1758, a PMT unit 1759, a PMT lens assembly 1760, a PMT pinhole nut 1761, a pinhole 1762, a pinhole hood 1763 and an adjustment bar 1765.

FIG. 18A shows a reader optics assembly 1810, a cartridge handling unit 1812 and a forward scatter detection unit 1814, in accordance with an embodiment of the present invention.

FIG. 18B shows a right side view of a complete reader optics assembly 1842, in accordance with an embodiment of the present invention.

FIG. 18C shows a left side view of the reader optics assembly, in accordance with an embodiment of the present invention.

FIG. 18D is a forward scatter detection assembly 1830, in accordance with an embodiment of the present invention. This assembly contains LEDs, 1852, to illuminate a reading channel (reading zone 130, FIG. 1) during an autofocus process, a stop 1858, to block low angle scatter and a lens 1856 to collect the desired forward scatter for the detection photodiode (such as (PMT) array 1560, FIG. 15).

FIG. 18E is a side view of forward scatter detection assembly 1830, in accordance with an embodiment of the present invention. Shown in this view are an illumination lens 1850, an collection lenses 1856, 1857, and 1858, as well as a detection photodiode 1860.

FIG. 19A shows a cutaway view of reader assembly 1930, in accordance with an embodiment of the present invention. This cutaway view of the reader assembly showing its components in its front and on a left side. These components include an ITX board 1922, a cartridge handling unit 1928, and the forward scatter detection assembly, 1930.

FIG. 19B shows an exploded right side view of a reader assembly 1905, in accordance with an embodiment of the present invention. The three major components in this view are a reader optics assembly 1942, a cartridge handling unit 1928, and a forward scatter detection module 1930.

FIG. 19C shows a left side blown up view of the reader assembly, in accordance with an embodiment of the present invention. Shown in this view are ITX computer board 1922, cartridge handling unit 1928, forward scatter detection assembly 1930, and the other side of the reader optics assembly 1942.

FIG. 19D shows a rear view of cartridge handling unit (CHU) 1928, in accordance with an embodiment of the present invention. In this view, a handle 1901 of the inserted cartridge, 1910, can be seen. Sensors 1912 are configured therein to detect the position of motors 1910, and actuators 1914, which are adapted to crush the blisters, 106, 108, 110 (FIG. 1) or 1420, 1422, 1424 (FIGS. 14A-14L) as well as an actuator 1916 to operate the bellows (940, FIG. 9, 1415, 1417 FIGS. 14A-L), can be seen on the shafts of the motor. An opening 1918 is provided for the microscope objective 2138 (FIG. 21A) to view the reading channel on the cartridge.

FIG. 19E shows a front view of a cartridge handling unit (CHU), in accordance with an embodiment of the present invention. This figure shows the front view of the cartridge handling unit (CHU) 1928. In this view, the handle in the upper portion of cartridge 1910 can be seen. A port 1920 to view the microfluidic path is provided. This port is viewed by a camera 1930, in order to ensure that the correct operation occurs within the cartridge. Another opening 1940 is provided for the forward scatter to exit the cartridge handling unit and be observed by the forward scatter detection assembly 1930.

FIG. 19F shows an exploded view of a reader optics assembly 1999, in accordance with an embodiment of the present invention.

FIG. 20 is a simplified illustration of a disposable cartridge 2050 for rapid determination of a medical condition, in accordance with an embodiment of the present invention;

Disposable cartridge 2050 is adapted to receive a bodily fluid, such as, but not limited to, blood, urine, serum or plasma. The disposable cartridge is constructed and configured to have several different sections 2052, 2054, 2056 and 2058. Section 2052 is a body fluid aspiration section, which is adapted to receive the body fluid directly or indirectly from the patient (or animal) and this section acts as a reservoir of the body fluid.

Disposable cartridge 2050 comprises fluid conveying means between the sections, such as, but not limited to, air pressure, liquid pressure, mechanical means and combinations thereof. Body fluid aspiration section 2052 is adapted to convey a predetermined quantity of the body fluid (a body fluid sample 2051) to a pre-analytical sample processing section 2054.

In pre-analytical sample processing section 2054, at least one preparatory step is performed on the body fluid such as, but not limited to:

a) incubation with at least one antibody;
b) incubation with at least one antigen;
c) staining of at least one cell type in the body fluid;
d) enzymatic lysing of at least one cell type of the body fluid;
e) osmotic lysing of at least one cell type of the body fluid;
f) heat or cool at least part of the bodily fluid;
g) addition of reference material to the bodily fluid; and
h) chemical reaction with at least one element of the body fluid.

The pre-treated sample of bodily fluid is then conveyed from pre-analytical sample processing section 2054 to a sample excitation/interaction zone or section 2056. This pre-treated sample may be conveyed continuously or in a batch mode to sample excitation/interaction section 2056.

FIG. 21A is a simplified schematic illustration of an optical arrangement of a reader optics assembly 2100, in accordance with an embodiment of the present invention;

A laser 2140 or other appropriate light source provides a light beam 2142, which may be directed towards a plurality of optical elements, including a dichroic filter 2143, a beam splitter 2144, a focusing lens 2145, a pinhole 2146 and a silicon reader unit 2147, for recording a signal from a beam 2142 directed through the objective 2138 towards a sample 2150 and returned to the optical unit. Additional optical elements may include an optional attenuator 2148, a high-pass filter 2149, a focusing lens 2151, a slit 2152, a concave grating 2153, and a PMT array 2154.

This arrangement of elements, representing an embodiment of the present invention, allows for generation of excitation light, focusing it on a sample, collecting reflected and emitted light signal resulting from the interaction of the excitation light and fluorophores in the sample and recording said returned light so as to determine fluorescence of sample in response to light illumination from laser 2140.

With respect to FIG. 21A, the laser illumination 2142 is reflected by the dichroic filter 2143 through the objective 2138 and focused on the channel containing the flowing particles 2158. This illumination excites the fluorophores attached to the protein markers that are bound to the cells. The resulting fluorescent illumination is collected by the objective 2138 and because of the longer wavelength of this emission passes through the dichroic filter 2143 and is reflected by the beam splitter 2144 through the high pass filter 2149. The high pass filter blocks any reflected laser illumination. The focusing lens 2151 focuses the multi-wavelength emission illumination on the slit 2152. The concave grating 2153 images the slit at multiple wavelengths on the elements of the PMT array 2154. This completes the process of creating a multispectral detection of the fluorescent emission. While most of the illumination collected by the objective is reflected by the beam splitter 2144 a small fraction is allowed to pass through and is focused by focusing lens 2145 through a pinhole 2146 on the silicon reader unit 2147, which may be a single photodiode or a focal plane array such as CCD sensor.

During the focusing operation, best focus is achieved when the signal on this reader unit 2147 is maximized. When this signal is maximized, the intensity of the signal on the PMT array 2154 is also maximized.

Reference is now made to FIG. 22A, which is a schematic representation 2200 of one example of multi-wavelength excitation in the optical unit of FIG. 21A or 21B, in accordance with an embodiment of the present invention. FIGS. 22A-22C show an extension of the optical configuration in FIGS. 21A and 21B, to allow multiple excitation wavelengths.

FIG. 22A shows the configuration for combining multiple lasers of different wavelengths to yield a single coaxial beam 2214 (see fig) containing all of the wavelengths. Two different wavelengths, such as green 2202 and red 2206, may be combined using a dichroic mirror 2204. One of the beams, red 2206 is reflected by the dichroic mirror, while the second beam, green 2202 passes through the dichroic mirror to yield a single beam 2208, yellow, containing both wavelengths. This combined wavelength beam is now used as one of the inputs to a second dichroic mirror 2210 with the third wavelength 2212 being reflected by the second dichroic mirror to yield a single coaxial beam 2216 containing all three wavelengths.

Reference is now made to FIG. 22B, which shows a graphical output 2220 of transmission as a function of wavelength for a dichroic filter 2200 of FIG. 7B, employing the multi-wavelength excitation of FIG. 22A, in accordance with an embodiment of the present invention. A multiband dichroic mirror (not shown) similar, or identical to, mirror 2252 of FIG. 22C is used to illuminate the sample through an objective 2254 (FIG. 8C), while allowing the resulting emission to pass through dichroic mirror 2252 at all wavelengths, except those of multibeam excitation 2214 (FIG. 8A). In this way the same epi-configuration used with a single wavelength can, in fact, be used with appropriate changes to dichroic mirror 2252 and the addition of multiple lasers 2202, 2206, 2212 to provide multi-wavelength excitation, while maintaining virtually all of the detection wavelengths of a single excitation system.

Turning to FIG. 22C, a schematic representation of part 2250 of the optical unit is seen, employing multi-wavelength excitation of FIG. 22A and the dichroic filter of FIG. 22B, in accordance with an embodiment of the present invention. Part 2250 may, in some cases, replace subsystem 2175 (FIG. 21B).

TABLE 4

Representative values for representative components for use in the present invention.

| Laser Wavelength | 405 nm | 488 nm |
|---|---|---|
| Laser Power | 50 mW | 20 mW |
| Sensing Spectral Range | 200 nm | 200 nm |
| Spectral Resolution | 25 nm | 25 nm |
| Number of Detectors | 8 | 8 |
| Collecting Optics | Microscope Objective N.A. > 0.4, W.D.~6 mm | Microscope Objective N.A. > 0.4, W.D.~6 mm |
| Detector Type | S.S. PMT 8 ch | S.S. PMT 8 ch |

While much of the previous discussion has focused on the optical elements of some embodiments of the present invention, one of the key components of the diagnostic system herewith presented is a disposable sample cartridge.

Reference is now made to FIG. 23A, which is a schematic view of a sampling cartridge 110 of FIG. 19A, or 102 (FIG. 1) in accordance with an embodiment of the present invention. The cartridge 2350 includes a pre-analytical component 2352 into which a sample (not shown) may be introduced.

The sample will generally be blood, either whole or a component (serum, etc.) thereof. Other liquid samples may additionally or alternatively be employed. In the pre-analytical component 2352, the sample is allowed to interact with chemicals pre-packaged into component 2352. The interaction may be either passive or include active mixing.

The chemicals included in the analytical component 2352 may be either wet or dry, and generally include antibodies associated with fluorescent probes. Antibodies are pre-selected for their ability to bind with predetermined biological markers or the like. In a typical experiment, a predetermined volume (generally less than 50 microliters) of blood is introduced into the pre-analytical component 2352 of a disposable cartridge 2350.

The sample is actively mixed with chemical reagents present in the pre-analytical component 2352 for a predetermined period of time, generally less than ten minutes. The sample is then moved through a capillary region 2353 by means to be discussed, where it is exposed to a light beam 2342 delivered from an objective 2338. Direction of sample flow is as shown by the arrow in the capillary region 2353.

The capillary region 2353 is designed to allow flow of particles in a single-file past the light beam 2342. Such an arrangement allows both for counting the number of particles as well as individual interrogation of particles to determine the presence of biological markers (via their associated fluorescent tags) on each particle. Such a physical arrangement allows for detection of one or more biological markers (independent of particle-specific properties such as size, shape, and number) on each particle.

Finally, there is a collection component 2354 which receives sample after exposure to light beam 2342. This is a waste region and allows for a completely self-contained disposable for sample preparation, analysis and waste collection. It is noted that the disposable cartridge may be of any relevant shape and is shown as it is in FIG. 20 for ease of understanding of its components and functionality.

As mentioned above, the sample, after pre-analytical treatment to allow for binding of fluorescent tag to cells/particles, must flow under a light beam 2342, produced by an optical unit (not shown). The flow is generally "single file" so as to allow for accurate determination of cell-specific markers on each analyzed cell. Methods to induce flow include but are not limited to electrical stimulation, chemical induction, and vacuum pull. In an electrical stimulation system, charge is applied across the capillary region 2353 so as to induce charged particles to move from the pre-analytical component 2352 towards the collection component 2354. The charge could be supplied by the cytometer in which the disposable cartridge 2350 is placed or from an external source.

Alternatively, the capillary region may include chemical features (hydrophilic/hydrophobic; positive/negative charge) to encourage sample to move from left to right as shown in FIG. 23A. Alternatively, a vacuum from the collection component 2354 could be applied to pull sample from the pre-analytical component through the capillary region 2353. Other methods may be employed to get liquid sample to move underneath the light beam 2342 for analysis.

As described herein, the optics and sample handling have been handled separately. Such an arrangement is not mandatory, as some of the optical features needed for proper sample analysis may be included in a disposable cartridge.

Reference is now made to FIG. 23B, which shows a schematic view of disposable cartridge 2300 in flow-cytometer device, such as system 100 in accordance with an embodiment of the present invention. Attention is currently turned to FIG. 23B which shows an expanded view of a capillary region 2353. In the capillary region 2353, particles 2390 flow in the direction as suggested by the arrow 2380.

Particles 2390 flow past an objective 2338 that shines light 2342 through the capillary 2353. Flow restriction elements 2394 may be present in the capillary region so as to encourage particles 2390 to move past the light 2342 in a nearly single file manner. Passage of multiple particles together may be resolved through processing software.

A molecular marker 2395 on a particle 2390 may be illuminated by light 2342 and its fluorescence will be captured by a proximate photomultiplier tube 2399. The photomultiplier tube 2399 may distinguish the wavelength of the fluorescence and thus which biological marker 2395 is present on particle 2390. Thus, the systems of the present invention may determine which biological markers are present on particles 2390, which are detected in the systems of the present invention. A photomultiplier tube 2399 may have a plurality of tubes or an array of elements for fine wavelength discrimination and alternatively may be replaced with film, CCD or other appropriate light-receiving reader unit. It should be understood that FIG. 23B shows one embodiment of the configuration of system 1200 (FIG. 12) in a transmissive configuration, wherein detector (photomultiplier tube 2399) is disposed on an opposing side of the cartridge 2300 to objective 2338.

The systems of the present invention comprise controller software which are adapted to run a diagnostic process. It is understood that the controller software may be an integral part of the flow-cytometer or alternatively be installed on an associated computing device (see FIGS. 1 & 12A), which may include, but not be limited to, a laptop computer, iPod, iPad, cell phone or mainframe computer.

Reference is now made to FIG. 24, which is a simplified flowchart 2400 of a method for rapid determination of a medical condition, in accordance with an embodiment of the present invention. It is to be understood that the method described herein depicts one non-limiting embodiment of the present invention for determining the health state of a patient. Further embodiments are also construed to be part of the present invention.

In a body fluid provision step 2402, a body fluid, such as blood, urine, serum or plasma is provided from a human or animal patient. Typically, the sample is fresh, but may also be a stored, refrigerated or frozen-thawed sample. The fluid is typically liquid and at a temperature of 4-37° C.

In a body fluid introduction step 2404, part or all of the body fluid sample 2051 (FIG. 20) is introduced into disposable cartridge (102, FIG. 1).

In a reacting step 2406, the fluid sample is reacted with at least one reactant in the cartridge forming a treated sample. According to some embodiments, this step is performed in pre-analytic al sample processing section 2054 (FIG. 20) as described in detail hereinabove.

In an impinging step 2408, radiation is impinged on the treated sample, such as, but not limited to, in sample excitation/interaction section 2056, thereby generating a plurality of spectrally distinct signals in the direction of optics unit 1242 (FIG. 12C, see description hereinabove).

In a spectral emissions detection step 2410, a plurality of spectrally distinct signals is detected by multiple emission detector 2154 (FIG. 21A). The detector outputs data.

Thereafter, in a data processing step 2412, the outputted data is processed by signal processor 2036 (FIG. 20) and/or by computer 1222 (FIG. 12C) to provide an output indicative of a medical condition.

FIG. 25 is a three-dimensional graph showing the optical output over time of reference beads (RM) relative to a sample from a human patient (PMN), in accordance with an embodiment of the present invention.

FIG. 25 shows a three-dimensional graph showing the optical output over time of reference beads (RM) relative to a sample from a human patient (PMN), in accordance with an embodiment of the present invention. The emission amplitude in the six bands, 500-525 nm, 525-550 nm, 550-575 nm, 575-600 nm, 600-625 nm and 625 to 650 nm is displayed in the graph for each sample time. Different fluorophores have different emission spectra. It can be appreciated that both spectral content or shape and amplitude at individual wavelengths are significantly different for neutrophils stained with Acridine Orange (AO) and reference beads (RM) containing a bright broad spectrum fluorophore. The peak of the AO emission is in the 525-550 nm band, while that of RM is in the 500-525 nm band and is of a significantly greater amplitude than AO in any band.

FIGS. 26A-26C show graphs of optical outputs over time of the reference beads and the sample from a human patient, in accordance with an embodiment of the present invention.

Turning to FIGS. 26A-26C, there can be seen graphs of optical outputs over time of the reference beads and the sample from a human patient, in accordance with an embodiment of the present invention. In these two-dimensional figures, the traces from each of the bands are overlaid on the same graph. FIG. 26A shows the boxed pulses from neutrophils in FIG. 26B.

It is seen from these graphs that the amplitude in the 525-550 nm channel exceeds the amplitude in the 500-525 nm channel, which is the characteristic of AO. FIG. 26C shows a comparison of the AO stained neutrophil emission spectrum to that of the RM emission spectrum. The relative amplitude of the spectrum in the 500-525 nm band to that of the amplitude in the 525-550 nm band clearly distinguishes the two fluorophores. In addition, the maximum amplitude of the RM emission is significantly greater than that of AO.

The systems of the present invention, as described and shown herein provide uses, such as, but not limited to, at least one of the four following scenarios:
  a) When multiple pieces of information, such as biological markers and white cell state are required in order to make an accurate diagnostic determination;
  b) When multiple sequential measurements must be made in order to determine the position of a patient on an illness curve;
  c) When white cell and similar data are needed quickly and in a POC environment; and
  d) When fluorescent signals overlap in wavelength and there is need to determine relative contribution of each signal for a given wavelength range.

The systems, kits, methods, apparatus and cartridges of the present invention and priority documents provides a very useful platform for many laboratory applications. The following listing hereinbelow is meant to be exemplary and not to be deemed limiting.

The systems, kits, methods, apparatus and cartridges of the present invention can be applied to cell Surface Markers, such as a CD64 Assay (see U.S. Pat. No. 8,116,984 and Davis, Bruce H., et al. "Neutrophil CD64 is an improved indicator of infection or sepsis in emergency department patients." Archives of pathology & laboratory medicine 130.5 (2006): 654-661; Hoffmann, Johannes J M L. "Neutrophil CD64 as a sepsis biomarker." Biochemia Medica 21.3 (2011): 282-290.

The systems, kits, methods, apparatus and cartridges of the present invention can be applied to cell Surface Markers, such as a CD64 Assay cell Surface Markers, such as a CD4/CD8 Assay (see Crowe, Suzanne, et al. "Monitoring of human immunodeficiency virus infection in resource-constrained countries." Clinical infectious diseases 37. Supplement 1 (2003): S25-S35.).

The systems, kits, methods, apparatus and cartridges of the present invention can be applied to stem cell identification (see Nielsen, Julie S., and Kelly M. McNagny. "Novel functions of the CD34 family." Journal of Cell Science 121.22 (2008): 3683-3692.).

The systems, kits, methods, apparatus and cartridges of the present invention can be applied to Minimal Residual Disease Assays (see Rawstron, A. C., et al. "International standardized approach for flow cytometric residual disease monitoring in chronic lymphocytic leukaemia." Leukemia 21.5 (2007): 956-964; Rawstron, Andy C., et al. "Report of the European Myeloma Network on multiparametric flow cytometry in multiple myeloma and related disorders." haematologica 93.3 (2008): 431-438; Briiggemann, M., et al. "Standardized MRD quantification in European ALL trials: proceedings of the Second International Symposium on MRD assessment in Kiel, Germany, 18-20 Sep. 2008." Leukemia 24.3 (2009): 521-535; Rawstron, A. C., et al. "Improving efficiency and sensitivity: European Research Initiative in CLL (ERIC) update on the international harmonised approach for flow cytometric residual disease monitoring in CLL." Leukemia 27.1 (2012): 142-149; Bottcher, Sebastian, Matthias Ritgen, and Michael Kneba. "Flow cytometric MRD detection in selected mature B-cell malignancies." Lymphoma. Humana Press, 2013. 149-174; Stehlfkova, O., et al. "Detecting minimal residual disease in patients with chronic lymphocytic leukemia using 8-color flow cytometry protocol in routine hematological practice." International journal of laboratory hematology (2013); Mullier, Francois, and Bernard Chatelain. "Immunophenotyping by flow cytometry." Belgian Haematological Society: Postgraduate seminar of the on Laboratory Techniques. 2013; Wiestner, Adrian, et al. "ZAP-70 expression identifies a chronic lymphocytic leukemia subtype with unmutated immunoglobulin genes, inferior clinical outcome, and distinct gene expression profile." Blood 101.12 (2003):4944-4951.

The systems, kits, methods, apparatus and cartridges of the present invention can be applied to lymphocyte subtyping (see Blue, MARIE-LUISE, et al. "Coexpression of T4 and T8 on peripheral blood T cells demonstrated by two-color fluorescence flow cytometry." The Journal of immunology 134.4 (1985): 2281-2286; Lanier, Lewis L., and Michael R. Loken. "Human lymphocyte subpopulations identified by using three-color immunofluorescence and flow cytometry analysis: correlation of Leu-2, Leu-3, Leu-7, Leu-8, and Leu-11 cell surface antigen expression." The Journal of Immunology 132.1 (1984): 151-156; Mercolino, Thomas J., et al. "Immunologic differentiation of absolute lymphocyte count with an integrated flow cytometric system: a new concept for absolute T cell subset determinations." Cytometry 22.1 (1995): 48-59; Comans-Bitter, W. Marieke, et al. "Immunophenotyping of blood lymphocytes in childhood Reference values for lymphocyte subpopulations." The Journal of pediatrics 130.3 (1997): 388-393; Inghirami, G., et al. "Flow cytometric and immunohistochemical characterization of the gamma/delta T-lymphocyte population in normal human lymphoid tissue and peripheral blood." The American journal of pathology 136.2 (1990): 357.).

The systems, kits, methods, apparatus and cartridges of the present invention can be applied to subtyping T subtypes and natural killer (NK) subtypes.

The systems, kits, methods, apparatus and cartridges of the present invention can be applied to BO21 White Blood Cell Differential analysis (see Kass, Lawrence. "Metachromatic dye sorption and fluorescent light emissive means for differential determination of developmental stages of neutrophilic granulocytic cells and other leukocytes." U.S. Pat. No. 4,500,509. 19 Feb. 1985.).

The systems, kits, methods, apparatus and cartridges of the present invention can be applied to cell cycle analysis, cell proliferation detection, cytokine detection and the like.

The systems, kits, methods, apparatus and cartridges of the present invention can be applied to detecting apoptosis using propidium iodide and/or other stains.

The systems, kits, methods, apparatus and cartridges of the present invention can be applied to plasma protein bead assays (see Cheng, Ann-Joy, et al. "Oral cancer plasma tumor marker identified with bead-based affinity-fractionated proteomic technology." Clinical Chemistry 51.12 (2005): 2236-2244.).

The systems, kits, methods, apparatus and cartridges of the present invention can be applied to solution changes (color, turbidity etc.—see Bonini, Pierangelo, et al. "Errors in laboratory medicine." Clinical Chemistry 48.5 (2002): 691-698; Legrand, C., et al. "Lactate dehydrogenase (LDH) activity of the number of dead cells in the medium of cultured eukaryotic cells as marker." Journal of biotechnology 25.3 (1992): 231-243. LDH, LACTATE DEHYDROGENASE, and Green Top. "Lactate Dehydrogenase (LDH)." (1980); Canning, D. M., and R. G. Huntsman. "An assessment of Sickledex as an alternative to the sickling test." Journal of Clinical Pathology 23.8 (1970): 736-737.

The systems, kits, methods, apparatus and cartridges of the present invention can be applied to combination analyses, such as, but not limited to:
1. Cell Surface Markers and Cell Element Staining
2. Apoptosis with Annexin (see Bossy-Wetzel, Ella, and Douglas R. Green. "Detection of apoptosis by annexin V labeling." Methods in enzymology 322 (2000): 15-18.).
3. Cell Surface Markers and Plasma Protein Bead Assays
4. Cell Element Staining and Plasma Protein Bead Assays
5. Cell Surface Markers and Solution Changes
6. 5. Cell Element Staining and Solution Changes
7. 2. Cell Cycle Analysis The instant invention includes software and algorithms for proper data analysis and conversion of raw fluorescence data into actual concentrations of relative biological markers.

The references cited herein teach many principles that are applicable to the present invention.

Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various 5 modifications and changes can be applied to the embodiments of the invention as hereinbefore described without departing from its scope, defined in and by the appended claims.

REFERENCES

Assicot, Marcel, et al. "High serum procalcitonin concentrations in patients with sepsis and infection." *The Lancet* 341.8844 (1993): 515-518.

Aulesa, C., et al. "Validation of the Coulter LH 750 in a hospital reference laboratory." *Laboratory Hematology*

9.1 (2003): 15-28. Hawkins, Robert C. "Laboratory turnaround time." The Clinical Biochemist Reviews 28.4 (2007): 179.

Ault, Kenneth A. "Flow cytometric measurement of platelet function and reticulated platelets." *Annals of the New York Academy of Sciences* 677.1 (1993): 293-308.

Blajchman, Morris A., et al. "Bacterial detection of platelets: current problems and possible resolutions." *Transfusion medicine reviews* 19.4 (2005): 259-272.

Bodensteiner, David C. "A flow cytometric technique to accurately measure post-filtration white blood cell counts." *Transfusion* 29.7 (1989): 651-653.

Cheson, Bruce D., et al. "National Cancer Institute-sponsored Working Group guidelines for chronic lymphocytic leukemia: revised guidelines for diagnosis and treatment." *Blood* 87.12 (1996): 4990-4997.

Christ-Crain, Mirjam, et al. "Effect of procalcitonin-guided treatment on antibiotic use and outcome in lower respiratory tract infections: cluster-randomised, single-blinded intervention trial." *Lancet* 363.9409 (2004): 600-607.

Cristofanilli, Massimo, et al. "Circulating tumor cells, disease progression, and survival in metastatic breast cancer." *New England Journal of Medicine* 351.8 (2004): 781-791.

Davis, Bruce H., et al. "Neutrophil CD64 is an improved indicator of infection or sepsis in emergency department patients." Archives of pathology & laboratory medicine 130.5 (2006): 654-661.

Dieye, Tandakha Ndiaye, et al. "Absolute CD4 T-cell counting in resource-poor settings: direct volumetric measurements versus bead-based clinical flow cytometry instruments." *J AIDS Journal of Acquired Immune Deficiency Syndromes* 39.1 (2005): 32-37.

Divers, S. G., et al. "Quantitation of CD62, soluble CD62, and lysosome-associated membrane proteins 1 and 2 for evaluation of the quality of stored platelet concentrates." *Transfusion* 35.4 (2003): 292-297.

Drexler, Hans G., et al. "Diagnostic value of immunological leukemia phenotyping." *Acta haematologica* 76.1 (1986): 1-8.

Dziegiel, Morten Hanefeld, Leif Kofoed Nielsen, and Adela Berkowicz. "Detecting fetomaternal hemorrhage by flow cytometry." *Current opinion in hematology* 13.6 (2006): 490.

Fischer, Johannes C., et al. "Reducing costs in flow cytometric counting of residual white blood cells in blood products: utilization of a single platform bead free flow rate calibration method." Transfusion 51.7 (2011): 1431-1438.

Free, A. H., and H. M. Free. "Urinalysis, critical discipline of clinical science." Critical Reviews in Clinical Laboratory Sciences 3.4 (1972): 481-531.

Frengen, Jomar, et al. "Demonstration and minimization of serum interference in flow cytometric two-site immunoassays." *Clinical chemistry* 40.3 (1994): 420-425.

Frengen, J., et al. "Homogeneous immunofluorometric assays of alpha-fetoprotein with macroporous, monosized particles and flow cytometry." *Clinical chemistry* 39.10 (1993): 2174-2181.

Gosling, James P. "A decade of development in immunoassay methodology." *Clinical chemistry* 36.8 (1990): 1408-1427.

Graff, Jochen, et al. "Close relationship between the platelet activation marker CD62 and the granular release of platelet-derived growth factor." *Journal of Pharmacology and Experimental Therapeutics* 300.3 (2002): 952-957.

Guerti, K., et al. "Performance evaluation of the PENTRA 60C+ automated hematology analyzer and comparison with the AD VIA 2120." *International journal of laboratory hematology* 31.2 (2009): 132-141.

Hawkins, Robert C. "Laboratory turnaround time." The Clinical Biochemist Reviews 28.4 (2007): 179.

Hershman, M. J., et al. "Monocyte HLA-DR antigen expression characterizes clinical outcome in the trauma patient." *British Journal of Surgery* 77.2 (2005): 204-207.

Hilfrich, Ralf, and Jalil Hariri. "Prognostic relevance of human papillomavirus LI capsid protein detection within mild and moderate dysplastic lesions of the cervix uteri in combination with p16 biomarker." *Analytical and Quantitative Cytology and Histology* 30.2 (2008): 78-82.

Hillier, Sharon L., et al. "A case-control study of chorioamnionic infection and histologic chorioamnionitis in prematurity." New England Journal of Medicine 319.15 (1988): 972-978.

Kibe, Savitri, Kate Adams, and Gavin Barlow. "Diagnostic and prognostic biomarkers of sepsis in critical care." Journal of Antimicrobial Chemotherapy 66.suppl 2 (2011): ii33-ii40.

LaRosa, Steven P., and Steven M. Opal. "Biomarkers: the future." Critical care clinics 27.2 (2011): 407.

Liu, N. I. N. G., A. H. Wu, and Shan S. Wong. "Improved quantitative Apt test for detecting fetal hemoglobin in bloody stools of newborns." Clinical chemistry 39.11 (1993): 2326-2329.

Lotan, Yair, et al. "Bladder cancer screening in a high risk asymptomatic population using a point of care urine based protein tumor marker." *The Journal of urology* 182.1 (2009): 52-58.

Masse, M., et al. "Validation of a simple method to count very low white cell concentrations in filtered red cells or platelets." *Transfusion* 32.6 (2003): 565-571.

Matic, Goran B., et al. "Whole blood analysis of reticulated platelets: improvements of detection and assay stability." *Cytometry* 34.5 (1998): 229-234.

McDonald, C. P., et al. "Use of a solid-phase fluorescent cytometric technique for the detection of bacteria in platelet concentrates." *Transfusion Medicine* 15.3 (2005): 175-183.

Michelson, Alan D. "Flow cytometry: a clinical test of platelet function." *Open Access Articles* (1996): 290.

Miller, E. M.; Freire, S. L. S.; Wheeler, A. R. "Proteomics in Microfluidic Devices" In *Encyclopedia of Micro-* and *Nanofluidics-*, Li, D. Q., Ed.; Springer: Heidelberg, Germany, 2008; Vol. 3, pp 1749-1758."

Moro, Ricardo, et al. "A new broad-spectrum cancer marker." *Vitro Diagnostic Technology* (2005).

Ozanich Jr, Richard M., et al. "Rapid multiplexed flow cytometric assay for botulinum neurotoxin detection using an automated fluidic microbead-trapping flow cell for enhanced sensitivity." *Analytical chemistry* 81.14 (2009): 5783-5793.

Pal, Jozsef, et al. "Sandwich type ELISA and a fluorescent cytometric microbead assay for quantitative determination of hepatitis B virus X antigen level in human sera." *Journal of immunological methods* 306.1 (2005): 183-192.

Perry, Sara E., et al. "Is low monocyte HLA-DR expression helpful to predict outcome in severe sepsis?." *Intensive care medicine* 29.8 (2003): 1245-1252.

Ramakumar, Sanjay, et al. "Comparison of screening methods in the detection of bladder cancer." *The Journal of urology* 161.2 (1999): 388-394.

Rawstron, Andy C., et al. "Quantitation of minimal disease levels in chronic lymphocytic leukemia using a sensitive flow cytometric assay improves the prediction of outcome and can be used to optimize therapy." *Blood* 98.1 (2001): 29-35.

Rodriguez, William R., et al. "A microchip CD4 counting method for HIV monitoring in resource-poor settings." *PLoS medicine* 2.7 (2005): e182.

Rylatt, D. B., et al. "An immunoassay for human D dimer using monoclonal antibodies." *Thrombosis research* 31.6 (1983): 767-778. Sacks, David B., et al. "Guidelines and recommendations for laboratory analysis in the diagnosis and management of diabetes mellitus." Clinical Chemistry 48.3 (2002): 436-472.

Schwartz, Morton K., et al. "Chemical and Clinical Evaluation of the Continuous-flow Analyzer "SMAC"." Clinical Chemistry 20.8 (1974): 1062-1070.

Segal, H. C., et al. "Accuracy of platelet counting haematology analysers in severe thrombocytopenia and potential impact on platelet transfusion." *British Journal of Haematology* 128.4 (2005): 520-525.

Skeggs, Leonard T. "Method and apparatus for sequentially performing analyses on a plurality of fluid samples." U.S. Pat. No. 3,241,432. 22 Mar. 1966.

Skeggs, Leonard T., and Harry Hochstrasser. "Multiple automatic sequential analysis." Clinical Chemistry 10.10 (1964): 918-936.

Stein, Paul D., et al. "D-dimer for the exclusion of acute venous thrombosis and pulmonary embolism: a systematic review." *Annals of internal medicine* 140.8 (2004): 589.

Sutherland, D. Robert, et al. "The ISHAGE guidelines for CD34+ cell determination by flow cytometry." *Journal of hematotherapy* 5.3 (1996): 213-226.

Wang, Chao, et al. "Reticulated platelets predict platelet count recovery 5 following chemotherapy." *Transfusion* 42.3 (2002): 368-374.

Westgard, J. O., et al. "Performance studies on the Technicon "SMAC" analyzer: Precision and comparison of values with methods in routine laboratory service." Clinical chemistry 22.4 (1976): 489-496.

The invention claimed is:

1. A valveless, single use, microfluidic cartridge for performing an assay, the cartridge comprising:
a sealable sample chamber;
a first microfluidic blister comprising a first reagent;
optionally a second blister comprising a second reagent;
optionally a third blister comprising a third reagent;
a first mixing chamber;
a second mixing chamber;
a first bellows;
a second bellows;
a reading cuvette connected to the first mixing chamber;
wherein
the sample chamber, first blister and optionally the second blister are each connected to the first mixing chamber;
the first mixing chamber is connected to the second mixing chamber via a tortuous channel;
the first bellows is connected to the second mixing chamber;
the second bellows is adapted to force liquids from the first mixing chamber towards the reading cuvette;
and wherein the cartridge is being adapted to:
receive a sample into said sample chamber and to seal said sample chamber such that said cartridge is a closed system after sealing said sample chamber;
pass a predetermined quantity of said sample into said first mixing chamber;
transfer said first reagent from said first blister into said first mixing chamber;
operate said first bellows to transfer liquid back and forth between said first and said second mixing chambers, to mix said sample and said first reagent;
optionally transfer said second reagent from said second blister into said first mixing chamber and optionally operate said first bellows to transfer liquid back and forth between said first and said second mixing chambers;
optionally transfer said third reagent from said third blister into said second mixing chamber and optionally operate said first bellows to transfer liquid back and forth between said first and said second mixing chambers;
operate said second bellows to transfer liquid from said first mixing chamber, toward said reading cuvette.

2. The cartridge of claim 1, wherein said first mixing chamber is of a volume of 200 to 10000 microliters.

3. The cartridge of claim 1, wherein a volume of any of the blisters is from about 1 microliter to 1000 microliters.

4. The cartridge of claim 1, wherein a volume of the sample is about 10 microliters.

5. The cartridge of claim 1, wherein said cartridge has a shelf-life of 6 to 24 months.

6. The cartridge of claim 1, wherein said first bellows and/or said second bellows comprises an inflatable deformable elastic chamber adapted to apply at least one of a negative pressure and a positive pressure to said mixing chamber(s).

7. The cartridge of claim 1, wherein:
said first reagent comprises antibodies;
said second reagent or said third reagent comprises a diluent and/or a cell lysis reagent;
said second reagent or said third reagent comprise fluorescently tagged beads.

8. The cartridge of claim 7, wherein said antibodies comprise an antibody mixture comprising fluorescently tagged CD64 and fluorescently tagged CD163 antibodies.

9. The cartridge of claim 1, wherein said reagent(s) comprises at least one of:
i. at least one target antibody;
ii. at least one positive control identifying antibody; and
iii. at least one negative control identifying detection moiety.

10. The cartridge of claim 1, wherein said reagent(s) comprises at least one reference composition comprising at least one of:
i. a target signal reference composition; and
ii. a reference identifier composition.

11. The cartridge of claim 1, wherein said first reagent comprise at least one sepsis biomarker.

12. The cartridge of claim 11, wherein said at least one biomarker comprises at least one of CD64 and CD163 biomarkers.

13. The cartridge of claim 8, wherein the fluorescent tags of said beads comprising two fluorescent tags, wherein at least one of the two fluorescent tags on said beads is different from the fluorescently tagged CD64 and fluorescently tagged CD163 antibodies.

14. The cartridge of claim 7, wherein said antibodies are murine monoclonal antibodies.

15. The cartridge of claim 7, wherein the fluorescently tagged beads comprise Starfire Red.

16. The cartridge of claim 1, wherein the cell lysis reagent comprises ammonium chloride.

17. The cartridge of claim 1, wherein said sample comprises cells.

18. The cartridge of claim 1, wherein said sample is a blood sample.

19. The cartridge of claim 18, wherein said blood sample is whole blood.

20. The cartridge of claim 18, wherein the blood sample comprises erythrocytes and/or leukocytes, and wherein the leukocytes comprise lymphocytes and neutrophils.

21. The cartridge of claim 20, wherein the blood sample comprises leukocytes.

* * * * *